US011854666B2

(12) United States Patent
Muzzey et al.

(10) Patent No.: US 11,854,666 B2
(45) Date of Patent: Dec. 26, 2023

(54) NONINVASIVE PRENATAL SCREENING USING DYNAMIC ITERATIVE DEPTH OPTIMIZATION

(71) Applicant: Myriad Women's Health, Inc., South San Francisco, CA (US)

(72) Inventors: Dale Muzzey, San Francisco, CA (US); Carlo G. Artieri, San Bruno, CA (US); Eric Andrew Evans, Brisbane, CA (US); Imran Saeedul Haque, San Francisco, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 375 days.

(21) Appl. No.: 15/720,351

(22) Filed: Sep. 29, 2017

(65) Prior Publication Data

US 2018/0089364 A1 Mar. 29, 2018

Related U.S. Application Data

(60) Provisional application No. 62/554,910, filed on Sep. 6, 2017, provisional application No. 62/506,262, filed on May 15, 2017, provisional application No. 62/475,754, filed on Mar. 23, 2017, provisional application No. 62/424,303, filed on Nov. 18, 2016, provisional application No. 62/401,730, filed on Sep. 29, 2016.

(51) Int. Cl.
*G16B 20/10* (2019.01)
*G16B 20/00* (2019.01)
*G16B 30/00* (2019.01)
*G16B 40/00* (2019.01)
*G16B 30/10* (2019.01)
*G16B 40/30* (2019.01)
*G16B 20/20* (2019.01)
*C12Q 1/6869* (2018.01)
*C12Q 1/6883* (2018.01)
*C12Q 1/6809* (2018.01)

(52) U.S. Cl.
CPC .......... *G16B 20/10* (2019.02); *C12Q 1/6869* (2013.01); *C12Q 1/6883* (2013.01); *G16B 20/00* (2019.02); *G16B 30/00* (2019.02); *G16B 30/10* (2019.02); *G16B 40/00* (2019.02); *G16B 40/30* (2019.02); *C12Q 1/6809* (2013.01); *G16B 20/20* (2019.02)

(58) Field of Classification Search
None
See application file for complete search history.

(56) References Cited

U.S. PATENT DOCUMENTS

| | | |
|---|---|---|
| 5,476,930 A | 12/1995 | Letsinger et al. |
| 5,780,613 A | 7/1998 | Letsinger et al. |
| 6,251,638 B1 | 6/2001 | Umansky et al. |
| 6,258,540 B1 | 7/2001 | Lo et al. |
| 7,332,277 B2 | 2/2008 | Dhallan |
| 7,799,531 B2 | 9/2010 | Mitchell et al. |
| 7,838,647 B2 | 11/2010 | Hahn et al. |
| 8,008,018 B2 | 8/2011 | Quake et al. |
| 8,137,912 B2 | 3/2012 | Kapur et al. |
| 8,168,382 B2 | 5/2012 | Lo et al. |
| 8,383,338 B2 | 2/2013 | Kitzman et al. |
| 8,563,242 B2 | 10/2013 | Lo et al. |
| 8,603,749 B2 | 12/2013 | Gillevet |
| 8,700,338 B2 | 4/2014 | Oliphant et al. |
| 8,741,811 B2 * | 6/2014 | Lo ..................... C12Q 1/6886 506/8 |
| 9,092,401 B2 | 7/2015 | Richards et al. |
| 9,309,556 B2 | 4/2016 | Myllykangas et al. |
| 9,512,480 B2 | 12/2016 | Lo et al. |
| 2001/0051341 A1 | 12/2001 | Lo et al. |
| 2003/0211522 A1 | 11/2003 | Landes et al. |
| 2005/0164241 A1 | 7/2005 | Hahn et al. |
| 2006/0046258 A1 | 3/2006 | Lapidus et al. |
| 2007/0134658 A1 | 6/2007 | Bohmer |
| 2007/0178478 A1 | 8/2007 | Dhallan et al. |
| 2007/0202525 A1 | 8/2007 | Quake et al. |
| 2008/0138809 A1 | 6/2008 | Kapur et al. |
| 2008/0220422 A1 | 9/2008 | Shoemaker et al. |
| 2009/0029377 A1 | 1/2009 | Lo et al. |
| 2009/0061425 A1 | 3/2009 | Lo et al. |
| 2009/0087847 A1 | 4/2009 | Lo et al. |
| 2009/0170114 A1 | 7/2009 | Quake et al. |
| 2009/0203002 A1 | 8/2009 | Brown |

(Continued)

FOREIGN PATENT DOCUMENTS

| | | |
|---|---|---|
| CA | 2 282 793 C | 10/2010 |
| CA | 2 789 734 A1 | 8/2011 |

(Continued)

OTHER PUBLICATIONS http://en.wikipedia.org/wiki/Wikipedia:About; downloaded !Feb. 2, 2009.*

(Continued)

*Primary Examiner* — Joseph Woitach
(74) *Attorney, Agent, or Firm* — Foley & Lardner LLP

(57) ABSTRACT

Fetal maternal samples taken from pregnant women include both maternal cell-free DNA and fetal cell-free DNA. Described herein are methods for determining a chromosomal abnormality of a test chromosome or a portion thereof in a fetus by analyzing a test maternal sample of a woman carrying said fetus, wherein the test maternal sample comprises fetal cell-free DNA and maternal cell-free DNA. The chromosomal abnormality can be, for example, aneuploidy or the presence of a microdeletion. In some embodiments, the chromosomal abnormality is determined by measuring a dosage of the test chromosome or portion thereof in the test maternal sample, measuring a fetal fraction of cell-free DNA in the test maternal sample, and determining an initial value of likelihood that the test chromosome or the portion thereof in the fetal cell-free DNA is abnormal based on the measured dosage, an expected dosage of the test chromosome or portion thereof, and the measured fetal fraction.

12 Claims, 14 Drawing Sheets

(56) References Cited

U.S. PATENT DOCUMENTS

| | | |
|---|---|---|
| 2010/0022406 A1 | 1/2010 | Srinivasan et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0216151 A1 | 8/2010 | Lapidus et al. |
| 2010/0216153 A1 | 8/2010 | Lapidus et al. |
| 2010/0291572 A1 | 11/2010 | Stoughton et al. |
| 2010/0297710 A1 | 11/2010 | Hoyal-Wrightson et al. |
| 2011/0105353 A1 | 5/2011 | Lo et al. |
| 2011/0177517 A1 | 7/2011 | Rava et al. |
| 2011/0201507 A1 | 8/2011 | Rava et al. |
| 2011/0230358 A1 | 9/2011 | Rava |
| 2011/0245085 A1 | 10/2011 | Rava et al. |
| 2011/0276277 A1 | 11/2011 | Lo et al. |
| 2011/0281740 A1 | 11/2011 | Beecham et al. |
| 2011/0294699 A1 | 12/2011 | Lee et al. |
| 2012/0010091 A1* | 1/2012 | Linnarson ......... C12N 15/1096 506/7 |
| 2012/0100548 A1 | 4/2012 | Rava et al. |
| 2012/0135872 A1 | 5/2012 | Chuu et al. |
| 2012/0165203 A1 | 6/2012 | Quake et al. |
| 2012/0178918 A1 | 7/2012 | Wisniewski et al. |
| 2012/0184449 A1 | 7/2012 | Hixson et al. |
| 2012/0214678 A1 | 8/2012 | Rava et al. |
| 2012/0264115 A1 | 10/2012 | Rava |
| 2012/0264121 A1 | 10/2012 | Rava et al. |
| 2012/0270212 A1 | 10/2012 | Rabinowitz et al. |
| 2012/0277119 A1 | 11/2012 | Ehrich et al. |
| 2012/0295819 A1 | 11/2012 | Leamon et al. |
| 2013/0029852 A1 | 1/2013 | Rava et al. |
| 2013/0034546 A1 | 2/2013 | Rava et al. |
| 2013/0059733 A1 | 3/2013 | Lo et al. |
| 2013/0096011 A1 | 4/2013 | Rava et al. |
| 2013/0130923 A1 | 5/2013 | Ehrich et al. |
| 2013/0150253 A1 | 6/2013 | Deciu |
| 2013/0171185 A1 | 7/2013 | Settembre et al. |
| 2013/0253369 A1 | 9/2013 | Rabinowitz et al. |
| 2013/0288242 A1 | 10/2013 | Stoughton et al. |
| 2013/0324418 A1 | 12/2013 | Fuchs et al. |
| 2013/0338933 A1* | 12/2013 | Deciu ............... C12Q 1/6827 702/20 |
| 2014/0019064 A1 | 1/2014 | Lo et al. |
| 2014/0024536 A1 | 1/2014 | Richards et al. |
| 2014/0024541 A1 | 1/2014 | Richards et al. |
| 2014/0038830 A1 | 2/2014 | Srinivasan et al. |
| 2014/0051583 A1 | 2/2014 | Fan et al. |
| 2014/0141982 A1 | 5/2014 | Jacobson et al. |
| 2014/0162269 A1 | 6/2014 | Rabinowitz et al. |
| 2014/0162278 A1 | 6/2014 | Richards et al. |
| 2014/0180594 A1 | 6/2014 | Kim et al. |
| 2014/0193808 A1 | 7/2014 | Hahn et al. |
| 2014/0199691 A1 | 7/2014 | Chuu et al. |
| 2014/0242588 A1* | 8/2014 | Van Den Boom ... C12Q 1/6827 435/6.11 |
| 2014/0274740 A1 | 9/2014 | Srinivasan et al. |
| 2015/0044687 A1 | 2/2015 | Schmitt et al. |
| 2015/0051087 A1 | 2/2015 | Rabinowitz et al. |
| 2015/0065358 A1 | 3/2015 | Comstock et al. |
| 2015/0205914 A1 | 7/2015 | Richards et al. |
| 2015/0275289 A1 | 10/2015 | Otwinokowski et al. |
| 2015/0284712 A1 | 10/2015 | Kurihara et al. |
| 2016/0115544 A1 | 4/2016 | Elzinga |
| 2016/0224724 A1 | 8/2016 | Zhao |
| 2016/0239604 A1 | 8/2016 | Chudova |
| 2017/0321270 A1 | 11/2017 | Haque et al. |
| 2017/0355984 A1 | 12/2017 | Evans et al. |
| 2018/0201994 A1 | 7/2018 | Beauchamp et al. |
| 2018/0216103 A1 | 8/2018 | Lai et al. |
| 2018/0216176 A1 | 8/2018 | Chu et al. |

FOREIGN PATENT DOCUMENTS

| | | |
|---|---|---|
| WO | WO-2010/151842 A2 | 12/2010 |
| WO | WO-2011/057094 A1 | 5/2011 |
| WO | WO-2012/003374 A2 | 1/2012 |
| WO | WO-2012/040387 A1 | 3/2012 |
| WO | WO-2012/003374 A3 | 6/2012 |
| WO | WO-2012/078792 A2 | 6/2012 |
| WO | WO-2012/078792 A3 | 6/2012 |
| WO | WO-2012/088456 A2 | 6/2012 |
| WO | WO-2012/088456 A3 | 6/2012 |
| WO | WO-2013/112923 A1 | 8/2013 |
| WO | WO-2016/010856 A1 | 1/2016 |
| WO | WO-2016/130704 A2 | 8/2016 |
| WO | WO-2018/144216 A1 | 8/2018 |
| WO | WO-2018/144217 A1 | 8/2018 |

OTHER PUBLICATIONS

Sun et al Plasma DNA tissue mapping by genome-wide methylation sequencing for noninvasive prenatal, cancer, and transplantation assessments PNAS | Published online Sep. 21, 2015 www.pnas.org/cgi/doi/10.1073/pnas.1508736112.*

Ahn, J. et al. (May 2, 2017). "Asymmetrical barcode adapter-assisted recovery of duplicate reads and error correction strategy to detect rare mutations in circulating tumor DNA," *Scientific Reports* 7(46678): 1-9.

ACOG Committee on Genetics. (Sep. 2015). "Committee Opinion No. 640: Cell-Free DNA Screening for Fetal Aneuploidy," *Obstetrics and Gynecology* 126(3):e31-37.

Artieri, C.G. et al. (2017). "Noninvasive Prenatal Screening at Low Fetal Fraction: Comparing Whole-Genome Sequencing and Single-Nucleotide Polymorphism Methods," *Prenatal Diagnosis* 37:482-490.

Baer, R.J. et al. (Oct. 2015). "Detection Rates for Aneuploidy by First-Trimester and Sequential Screening," *Obstetrics & Gynecology* 126(4):753-759.

Chim, S.S.C. et al. (Oct. 11, 2005). "Detection of the Placental Epigenetic Signature of the *Maspin* Gene in Maternal Plasma," *PNAS USA* 102(42):14753-14758.

Chiu, R.W.K. et al. (Dec. 23, 2008). "Noninvasive Prenatal Diagnosis of Fetal Chromosomal Aneuploidy by Massively Parallel Genomic Sequencing of DNA in Maternal Plasma," *PNAS* 105(51):20458-20463, (with Supplementary material), twenty three pages.

Fan, H.C. et al. (May 3, 2010; e-published on Mar. 2010). "Sensitivity of Noninvasive Prenatal Detection of Fetal Aneuploidy from Maternal Plasma Using Shotgun Sequencing Is Limited Only by Counting Statistics," *PLoS ONE* 5(5):(e10439), pp. 1-7.

Gil, M.M. et al. (2015; e-published on Feb. 13, 2015). "Analysis of Cell-Free DNA in Maternal Blood in Screening for Fetal Aneuploidies: Updated Meta-Analysis," *Ultrasound in Obstetrics & Gynecology* 45(3):249-266.

Grati, F.R. et al. (Aug. 2014; e-published on Feb. 13, 2014). "Fetoplacental Mosaicism: Potential Implications for False-Positive and False-Negative Noninvasive Prenatal Screening Results," *Genetics in Medicine* 16(8):620-624.

Haas, K.R. et al. (Jul. 9-12, 2017). "Accurate Fetal Fraction from NIPS using Whole Genome Sequencing," Counsyl, Inc. Poster, presented at the *21st International Society for Prenatal Diagnosis*, San Diego, CA, USA, one page.

Hopmans, E.S. et al. (Apr. 29, 2014). "A Programmable Method for Massively Parallel Targeted Sequencing," *Nucleic Acids Res.* 42(10):e88, pp. 1-16.

Johansen, P. et al. (Jun. 2016; e-pub. Apr. 24, 2016). "Open Source Non-Invasive Prenatal Testing Platform and its Performance in a Public Health Laboratory," *Prenat. Diagn.* 36(6):530-536, with Supplementary Information, twelve pages.

Kim, S.K. et al. (Aug. 2015; e-published on Jun. 3, 2015). "Determination of Fetal DNA Fraction From the Plasma of Pregnant Women Using Sequence Read Counts," *Prenatal Diagnosis* 35(8):810-815, (including Supporting Information), fifteen pages.

Lo, Y.M.D. et al. (Aug. 7, 2007). "Digital PCR for the Molecular Detection of Fetal Chromosomal Aneuploidy," *PNAS* 104(32):13116-13121, (with Supplementary material), twenty six pages.

(56) References Cited

OTHER PUBLICATIONS

Mertes, F. et al. (Nov. 2011; e-published on Nov. 26, 2011). "Targeted Enrichment of Genomic DNA Regions for Next-Generation Sequencing," *Briefings in Functional Genomics* 10(6):374-386.

Meyer, M. et al. (2007; e-pub Aug. 1, 2007). "Targeted High-Throughput Sequencing of Tagged Nucleic Samples," *Nucleic Acids Research* 35(15):e97, pp. 1-5.

Muzzey, D. et al. (Sep. 28, 2016). "Maximizing Accuracy, Clinical Utility, and Patient Experience of Non-Invasive Prenatal Screening via Dynamic Iterative Depth Optimization," Counsyl, Inc. Poster, presented at the *National Society of Genetic Counselors*, Seattle, WA, USA, one page.

Myllykangas, S. et al. (Nov. 2011; e-published on Oct. 23, 2011). "Efficient Targeted Resequencing of Human Germline and Cancer Genomes by Oligonucleotide-Selective Sequencing," *Nat Biotechnol.* 29(11):1024-1027.

Ng, S.B. et al. (Sep. 10, 2009; e-published on Aug. 16, 2009). "Targeted Capture and Massively Parallel Sequencing of Twelve Human Exomes," *Nature* 461(7261):272-276.

Ryan, A. et al. (Oct. 2016; e-published on Mar. 31, 2016). "Validation of an Enhanced Version of a Single-Nucleotide Polymorphism-Based Noninvasive Prenatal Test for Detection of Fetal Aneuploidies," *Fetal Diagnosis Therapy* 40(3):219-223.

Saah, A.J. et al. (Jan. 1997). ""Sensitivity" and "Specificity" Reconsidered: The Meaning of these Terms in Analytical and Diagnostic Settings," *Annals of Internal Medicine* 126(1):91-94.

Sparks, A.B. et al. (Apr. 2012). "Noninvasive Prenatal Detection and Selective Analysis of Cell-Free DNA Obtained from Maternal Blood: Evaluation for Trisomy 21 and Trisomy 18," *American Journal of Obstetrics & Gynecology* 206:319.e1-e9.

Straver, R. et al. (Jul. 2016; e-pub. May 20, 2016). "Calculating the Fetal Fraction for Non Invasive Prenatal Testing Based on Genome-Wide Nucleosome Profiles," *Prenat Diagn.* 36(7):614-621, with Supplementary Information, 23 pages.

Wright, D. et al. (2015; e-pub. Dec. 1, 2014). "A Unified Approach to Risk Assessment for Fetal Aneuploidies," *Ultrasound Obstet Gynecol* 45:48-54.

Xu, X.-P. et al. (Jan. 14, 2016). "A Method to Quantify Cell-Free Fetal DNA Fraction in Maternal Plasma Using Next Genaration Sequencing: Its Application in Non-Invasive Prenatal Chromosomal Aneuploidy Detection," *PLoS One* 11(1):e0146997, thirteen pages.

Yaron, Y. (May 2016; e-published on Mar. 4, 2016). "The Implications of Non-Invasive Prenatal Testing Failures: A Review of an under-Discussed Phenomenon," *Prenatal Diagnosis* 36(5):391-396.

Zhao, C. et al. (Apr. 2015). "Detection of Fetal Subchromosomal Abnormalities by Sequencing Circulating Cell-Free DNA from Maternal Plasma," *Clinical Chemistry* 61(4):608-616.

Zhong, S. et al. (2011). "High-Throughput Illumina Strand-Specific RNA Sequencing Library Preparation," *Cold Spring Harbor Protocols* 2011(8):940-949.

Zimmermann, B. et al. (Dec. 2012; e-published on Oct. 30, 2012). "Noninvasive Prenatal Aneuploidy Testing of Chromosomes 13, 18, 21, X, and Y, Using Targeted Sequencing of Polymorphic Loci," *Prenat. Diagn.* 32(13):1233-1241, twenty one pages.

U.S. Appl. No. 15/934,839, filed Mar. 23, 2018 by Haas et al.

International Search Report and Written Opinion issued in corresponding International Application No. PCT/US2017/054318, dated Dec. 22, 2017 (10 pages).

\* cited by examiner

US 11,854,666 B2

NONINVASIVE PRENATAL SCREENING USING DYNAMIC ITERATIVE DEPTH OPTIMIZATION

CROSS-REFERENCE TO RELATED APPLICATIONS

This applications claims priority benefit to U.S. Provisional Application No. 62/401,730, filed on Sep. 29, 2016, entitled "NONINVASIVE PRENATAL SCREENING USING DYNAMIC ITERATIVE DEPTH OPTIMIZATION"; U.S. Provisional Application No. 62/424,303, filed on Nov. 18, 2016, entitled "NONINVASIVE PRENATAL SCREENING USING DYNAMIC ITERATIVE SEQUENCING DEPTH OPTIMIZATION"; U.S. Provisional Application No. 62/475,754, filed on Mar. 23, 2017, entitled "NONINVASIVE PRENATAL SCREENING USING DYNAMIC ITERATIVE SEQUENCING DEPTH OPTIMIZATION"; U.S. Provisional Application No. 62/506,262, filed on May 15, 2017, entitled "NONINVASIVE PRENATAL SCREENING USING DYNAMIC ITERATIVE DEPTH OPTIMIZATION"; and U.S. Provisional Application No. 62/554,910 filed on Sep. 6, 2017, entitled "NONINVASIVE PRENATAL SCREENING USING DYNAMIC ITERATIVE DEPTH OPTIMIZATION"; each of which is incorporated herein by reference for all purposes.

FIELD OF THE INVENTION

The present invention relates to the determination of fetal abnormalities by measuring dosages of one or more chromosomes or portions thereof from cell-free DNA.

BACKGROUND

Circulating throughout the bloodstream of a pregnant woman and separate from cellular tissue are small pieces of DNA, often referred to as cell-free DNA (cfDNA). The cfDNA in the maternal bloodstream includes cfDNA from both the mother (i.e., maternal cfDNA) and the fetus (i.e., fetal cfDNA). The fetal cfDNA originates from the placental cells undergoing apoptosis, and constitutes up to 25% of the total circulating cfDNA, with the balance originating from the maternal genome.

Recent technological developments have allowed for noninvasive prenatal screening of chromosomal aneuploidy in the fetus by exploiting the presence of fetal cfDNA circulating in the maternal bloodstream. Noninvasive methods relying on cfDNA sampled from the pregnant woman's blood serum are particularly advantageous over chorionic villi sampling or amniocentesis, both of which risk substantial injury and possible pregnancy loss.

Accurate determination of the fraction of fetal cfDNA taken from a maternal test sample allows for improved screening of fetal aneuploidy. The fetal fraction for male pregnancies (i.e., a male fetus) can be determined by comparing the amount of Y chromosome from the cfDNA, which can be presumed to originate from the fetus, to the amount of one or more genomic regions that are present in both maternal and fetal cfDNA. Determination of the fetal fraction for female pregnancies (i.e., a female fetus) is more complex, as both the fetus and the pregnant mother have similar sex-chromosome dosage and there are few features to distinguish between maternal and fetal DNA. Methylation differences between the fetal and maternal DNA can be used to estimate the fetal fraction of cfDNA, but such methods are often cumbersome. See, for example, Chim et al., PNAS USA, 102:14753-58 (2005). In another method, the fraction of fetal cfDNA can be determined by sequencing polymorphic loci to search for allelic differences between the maternal and fetal cfDNA. See, for example, U.S. Pat. No. 8,700,338. However, as explained in U.S. Pat. No. 8,700,338 (col. 18, lines 28-36), use of polymorphic loci to determine fetal fraction becomes unreliable when the fetal fraction drops below 3%. See also Ryan et al., Fetal Diag. & Ther., vol. 40, pp. 219-223 (Mar. 31, 2016), which describes setting a threshold for "no call" when the fetal fraction is below 2.8%.

The disclosures of all publications referred to herein are each hereby incorporated herein by reference in their entireties. To the extent that any reference incorporated by references conflicts with the instant disclosure, the instant disclosure shall control.

SUMMARY OF THE INVENTION

In one aspect, there is provided a method for determining a fetal chromosomal abnormality in a test chromosome or a portion thereof by analyzing a test maternal sample, comprising measuring a dosage of the test chromosome or the portion thereof in the test maternal sample comprising fetal cell-free DNA and maternal cell-free DNA; measuring a fetal fraction of cell-free DNA in the test maternal sample based on an over- or under-representation of fetal cell-free DNA from a plurality of bins within an interrogated region relative to maternal cell-free DNA; and determining an initial value of likelihood that the fetal cell-free DNA is abnormal in the test chromosome or the portion thereof based on the measured dosage, an expected dosage, and the measured fetal fraction. In some embodiments, the over- or under-representation is determined based on a sequencing read count. In some embodiments, the over- or under-representation is determined based on a count of hybridized probes.

In another aspect, there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA; measuring a fetal fraction of cell-free DNA in the test maternal sample based on a count of binned sequencing reads from an interrogated region from the maternal sample; and determining an initial value of likelihood that the fetal cell-free DNA is abnormal in the test chromosome or the portion thereof based on the measured dosage, an expected dosage of the test chromosome or the portion thereof, and the measured fetal fraction.

In some embodiments, determining the initial value of likelihood comprises: determining an initial value of statistical significance for the test chromosome or the portion thereof based on the measured dosage and the expected dosage; and determining the initial value of likelihood based on the initial value of statistical significance and the measured fetal fraction. In some embodiments, determining the initial value of likelihood accounts for the probability that the measured fetal proportion is reflective of a true fetal fraction.

In some embodiments, the method further comprises calling the test chromosome or the portion thereof to be abnormal if the absolute value of the initial value of statistical significance is above a predetermined threshold. In some embodiments, the method further comprises calling the test chromosome to be normal if the absolute value of the initial value of statistical significance is below a first predetermined threshold and the initial value of likelihood is below a second predetermined threshold.

In some embodiments, the dosage is measured using an initial assay that generates an initial plurality of quantifiable products, wherein the number of quantifiable products in the initial plurality indicates the measured dosage. In some embodiments, the method further comprises re-measuring the dosage of the test chromosome or the portion thereof using a subsequent assay that generates a subsequent plurality of quantifiable products from the test chromosome or the portion thereof if the initial value of likelihood is above a predetermined threshold; and determining a subsequent value of statistical significance for the test chromosome or the portion thereof based on the re-measured dosage. In some embodiments, the method further comprises re-measuring the dosage of the test chromosome or the portion thereof using a subsequent assay that generates a subsequent plurality of quantifiable products from the test chromosome if the absolute value of the initial value of statistical significance is below a predetermined threshold; and determining a subsequent value of statistical significance for the test chromosome or the portion thereof based on the re-measured dosage. In some embodiments, the method further comprises re-measuring the dosage of the test chromosome or the portion thereof using a subsequent assay that generates a subsequent plurality of quantifiable products from the test chromosome if the initial value of likelihood is above a predetermined threshold and the absolute value of the initial value of statistical significance is below a predetermined threshold; and determining a subsequent value of statistical significance for the test chromosome or the portion thereof based on the re-measured dosage. In some embodiments, the number of quantifiable products in the subsequent plurality indicates the re-measured dosage, and wherein the number of quantifiable products in the subsequent plurality is greater than the number of quantifiable products in the initial plurality. In some embodiments, the method further comprises combining the number of quantifiable products in the initial plurality with the number of quantifiable products in the subsequent plurality, thereby resulting in a combined number of quantifiable products that indicates the re-measured dosage.

In some embodiments, the method further comprises calling the test chromosome or the portion thereof to be abnormal if the absolute value of the subsequent value of statistical significance is above a predetermined threshold. In some embodiments, the method further comprises determining a subsequent value of likelihood that the fetal cell-free DNA is abnormal for the test chromosome or the portion thereof based on the re-measured dosage, the expected dosage, and the measured fetal fraction. In some embodiments, the method further comprises calling the test chromosome or the portion thereof to be normal if the subsequent value of likelihood is below a predetermined threshold.

In some embodiments, the quantifiable products are sequencing reads. In some embodiments, the quantifiable products are PCR products.

In another aspect, there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA; measuring a fetal fraction of cell-free DNA in the test maternal sample based an over- or under-representation of fetal cell-free DNA from a plurality of bins within an interrogated region relative to maternal cell-free DNA; and determining an initial value of statistical significance for the test chromosome or the portion thereof based on the measured dosage and the expected dosage. In some embodiments, the over- or under-representation is determined based on a sequencing read count. In some embodiments, the over- or under-representation is determined based on a count of hybridized probes.

In another aspect, there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA; measuring a fetal fraction of cell-free DNA in the test maternal sample based on a count of binned sequencing reads from an interrogated region from the maternal sample; and determining an initial value of statistical significance for the test chromosome or the portion thereof based on the measured dosage and the expected dosage. In some embodiments, the method further comprises calling the fetal cell-free DNA to be abnormal for the test chromosome if the initial value of statistical significance is above a first predetermined threshold.

In some embodiments, the chromosome dosage is measured using an assay that generates a plurality of quantifiable products, wherein the number of quantifiable products in the plurality indicates the measured chromosome dosage. In some embodiments, the quantifiable products are sequencing reads. In some embodiments, the quantifiable products are PCR products.

In some embodiments, the dosage of the test chromosome or the portion thereof and the fetal fraction are measured in a simultaneous assay. In some embodiments, the dosage of a plurality of test chromosomes or portions thereof is simultaneously measured.

In some embodiments, the fetal chromosomal abnormality is a microdeletion, and the one or more test chromosomes or the portion thereof is a putative microdeletion. In some embodiments, the putative microdeletion is determined using circular binary segmentation. In some embodiments, the putative microdeletion is determined using a hidden Markov model.

In some embodiments, the fetal chromosomal abnormality is aneuploidy, and the one or more test chromosomes or the portion thereof is at least one complete chromosome. In some embodiments, the test chromosome comprises chromosome 13, 18, 21, X, or Y.

In some embodiments, the value of statistical significance is a Z-score, a p-value, or a probability. In some embodiments, the value of likelihood is an odds ratio.

In some embodiments, the dosage of the test chromosome or the portion thereof is measured by: aligning sequencing reads from the test chromosome or portion thereof; binning the aligned sequencing reads in a plurality of bins; counting the number of sequencing reads in each bin; and determining an average number of reads per bin and a variation of the number of reads per bin.

In some embodiments, the expected dosage for the test chromosome or the portion thereof is determined by generating a dosage distribution vector comprising the dosage of at least one chromosome or portion thereof other than the test chromosome or portion thereof for each maternal sample in a plurality of maternal samples; training a machine-learning model by regressing the dosage distribution vector onto the dosage of the test chromosome or portion thereof for each maternal sample in the plurality of maternal samples; and applying the trained machine-learning model to a dosage distribution vector comprising the dosage of at least one chromosome or portion thereof other than the test chromosome or portion thereof from the maternal sample to obtain the expected dosage for the test chromosome or the portion thereof in the test maternal sample.

In some embodiments, the expected dosage for the test chromosome or the portion thereof is determined by: generating an average dosage vector comprising the average number of reads per bin from at least one chromosome or portion thereof other than the test chromosome or portion thereof for each maternal sample in a plurality of maternal samples; training a dosage average machine-learning model by regressing the average dosage vector onto the average number of sequencing reads per bin from the test chromosome or portion thereof for each maternal sample in the plurality of maternal samples; applying the trained dosage average machine-learning model to an average dosage vector comprising the average number of reads per bin from at least one chromosome or portion thereof other than the test chromosome or portion thereof from the maternal sample to obtain the expected average number of sequencing reads per bin for the test chromosome or the portion thereof in the test maternal sample; generating a dosage variation vector comprising the variation (e.g., standard deviation or interquartile range) of the number of reads per bin from at least one chromosome or portion thereof other than the test chromosome or portion thereof for each maternal sample in a plurality of maternal samples; training a dosage variation machine-learning model by regressing the dosage variation vector onto the variation of the number of sequencing reads per bin from the test chromosome or portion thereof for each maternal sample in the plurality of maternal samples; and applying the trained dosage variation machine-learning model to a dosage variation vector comprising the variation of the number of reads per bin from at least one chromosome or portion thereof other than the test chromosome or portion thereof from the maternal sample to obtain the expected variation of the number of sequencing reads per bin for the test chromosome or the portion thereof in the test maternal sample. In some embodiments, the at least one chromosome or portion thereof other than the test chromosome further comprises the test chromosome. In some embodiments, the plurality of maternal samples includes the test maternal sample. In some embodiments, the plurality of maternal samples does not include the test maternal sample.

In some embodiments, the expected chromosome dosage is determined by measuring an average number of reads per bin and a variation of the number of reads per bin for at least one chromosome or a portion thereof other than the test chromosome or portion thereof in the test maternal sample.

In some embodiments, the expected dosage for the test chromosome or the portion thereof is determined by measuring the dosage of at least one chromosome or portion thereof other than the test chromosome or portion thereof from the test maternal sample.

In some embodiments, the expected dosage for the test chromosome or the portion thereof is determined by: measuring the dosage of a plurality of chromosomes or portions thereof other than the test chromosome or portion thereof from the test maternal sample; and determining an average dosage for the plurality of chromosomes or portions thereof.

In some embodiments, the expected dosage for the test chromosome or the portion thereof is determined by: measuring the dosage of the test chromosome or the portion thereof from a plurality of maternal samples other than the test maternal sample; and determining an average dosage for the test chromosome or portions thereof from the plurality of maternal sample other than the test maternal sample.

In some embodiments, measuring the fetal fraction comprises: aligning the sequencing reads from the interrogated region; binning the aligned sequencing reads from the interrogated region in a plurality of bins; counting the number of sequencing reads in each of at least a portion of the bins; and determining the measured fetal fraction based on the number of sequencing reads in the at least a portion of the bins using a trained machine-learning model.

In some embodiments, the machine-learning model is trained by: (i) for each training maternal sample in a plurality of training maternal samples, wherein each training maternal sample has a known fetal fraction of cell-free DNA: aligning sequencing reads from the interrogated region, binning the aligned sequencing reads from the interrogated region in a plurality of bins, and counting the number of sequencing reads in each bin; and (ii) determining one or more model coefficients based on the number of sequencing reads in each bin and the known fetal fraction for each training maternal sample in the plurality of training maternal samples. In some embodiments, the maternal samples are taken from women with male pregnancies, and the known fetal fraction is determined by quantifying an amount of Y chromosome, X chromosome, or a known aneuploid chromosome in the maternal sample. In some embodiments, the machine-learning model is a regression model. In some embodiments, the machine-learning model is a linear regression model. In some embodiments, the machine learning model is a ridge regression model.

In some embodiments, determining the measured fetal fraction further comprises adjusting the fetal fraction predicted by the machine-learning model using polynomial smoothing. In some embodiments, determining the measured fetal fraction further comprises adjusting the fetal fraction predicted by the machine-learning model or determined after polynomial smoothing using a scalar factor that accounts for differences between the male and female pregnancies.

In some embodiments, the interrogated region comprises at least a portion of a chromosome other than the test chromosome or the portion thereof. In some embodiments, the interrogated region comprises at least a whole chromosome other than the test chromosome. In some embodiments, the interrogated region comprises a plurality of chromosomes. In some embodiments, the interrogated region does not include an X chromosome or a Y chromosome. In some embodiments, the interrogated region does not include the test chromosome.

In some embodiments, the method further comprises normalizing the number of sequencing reads prior to counting the sequencing reads. In some embodiments, the sequencing reads are normalized for variations in GC content or read mappability.

In some embodiments, each bin is between about 1 base in length and about 1 chromosome in length (for example about 10 kilobases to about 80 kilobases in length).

In some embodiments, the test maternal sample is obtained from a woman with a body mass index of about 30 or more.

In some embodiments, the method is implemented by a program executed on a computer system.

In some embodiments, the method further comprises reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

In some embodiments, the method further comprises reporting a performance summary statistic. In some embodiments, the performance summary statistic is a clinical specificity, a clinical sensitivity, a positive predictive value, or a negative predictive value. In some embodiments, the performance summary statistic is determined based on the measured fetal fraction of cell-free DNA in the test maternal sample. In some embodiments, the performance summary statistic is determined based on a fetal fraction range, and the measured fetal fraction is within said range. In some embodiments, the performance summary statistic is determined based on a specific fetal fraction consistent with the measured fetal fraction. In some embodiments, the method comprises determining a performance summary statistic for the method.

DETAILED DESCRIPTION

Figure 1:
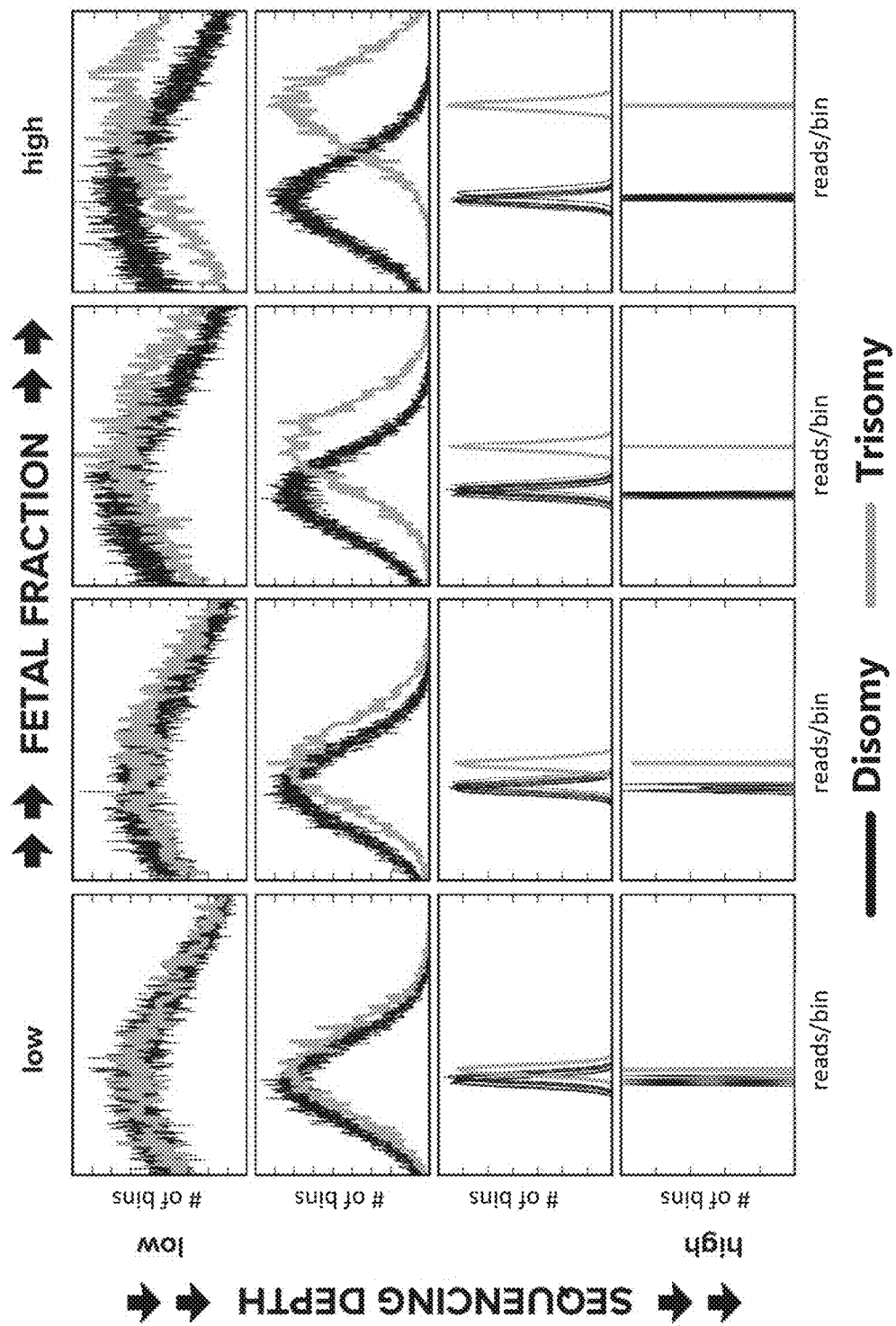
FIG. 1 illustrates the impact of fetal fraction and assay depth (specifically sequencing read depth) on resolving a triploid test chromosome (chromosome 21 in the illustrated example) dosage and an expected test chromosome dosage (which is expected to be diploid).

Provided herein are methods for determining a fetal chromosomal abnormality (such as a microdeletion or chromosomal aneuploidy) in a test chromosome or a portion thereof by analyzing a test maternal sample, comprising measuring a dosage of the test chromosome or the portion thereof in the test maternal sample comprising fetal cell-free DNA and maternal cell-free DNA; measuring a fetal fraction of cell-free DNA in the test maternal sample based on a count of binned sequencing reads from an interrogated region from the maternal sample; and determining an initial value of likelihood (such as an odds ratio) that the fetal cell-free DNA is abnormal in the test chromosome or the portion thereof based on the measured dosage, an expected dosage, and the measured fetal fraction. In some embodiments, determining the initial value of likelihood comprises determining an initial value of statistical significance (such as a Z-score or a p-value) for the test chromosome or the portion thereof based on the measured dosage and the expected dosage; and determining the initial value of likelihood based on the initial value of statistical significance and the measured fetal fraction. Also provided herein are methods for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA; measuring a fetal fraction of cell-free DNA in the test maternal sample based on a count of binned sequencing reads from an interrogated region from the maternal sample; and determining an initial value of statistical significance for the test chromosome or the portion thereof based on the measured dosage and the expected dosage.

In some instances, the determination of the initial value of likelihood or the initial value of statistical significance does not allow for calling the test chromosome in the fetal cfDNA as normal or abnormal with sufficient statistical confidence. Thus, in some embodiments, a subsequent value of likelihood or a subsequent value of statistical significance is determined using a re-measured chromosome dosage, wherein the re-measured chromosome dosage is determined using an assay that provides higher accuracy for the measured test chromosome dosage.

Noninvasive prenatal screens can be used to determine fetal aneuploidies for one or more test chromosomes using cell-free DNA from a test maternal blood sample. The results of screening can, for example, inform the patient's decision whether to pursue invasive diagnostic testing (such as amniocentesis or chronic villus sampling), which has a small (but non-zero) risk of miscarriage. Aneuploidy detection using noninvasive cfDNA analysis is linked to fetal fraction (that is, the proportion of cfDNA in the test maternal sample attributable to fetal origin). Aneuploidy can manifest in noninvasive prenatal screens that rely on a measured test chromosome dosage as a statistical increase or decrease in the count of quantifiable products (such as sequencing reads) that can be attributed to the test chromosome relative to an expected test chromosome dosage (that is, the count of quantifiable products that would be expected if the test chromosome were disomic). For samples with low fetal fraction, a large number of quantifiable products (e.g., a high read depth) are needed to achieve a statistically significant increase or decrease. Conversely, for samples with high fetal fraction, a smaller number of quantifiable products (e.g., a low read depth) can provide the statistically significant increase or decrease.

The methods described herein can also be used to detect microdeletions in a fetal chromosome. Microdeletions are portions of a chromosome (often on the order of 2 million bases to about 10 million bases, but can be larger or smaller), and can cause significant deleterious effects to the fetus.

As further described herein, an initial dosage of a test chromosome or a portion thereof from a test maternal sample can be measured, and a statistical analysis (such as the determination of a value of likelihood that the test chromosome is abnormal or a value of statistical significance) can be performed. The statistical analysis can determine whether a call of normal (such as euploidy or no microdeletion) or abnormal (such as aneuploidy or the presence of a microdeletion) for the test chromosome or portion thereof can be made within the desired level of confidence. In some embodiments, if the call cannot be made within the desired level of confidence or likelihood, the chromosome dosage is re-measured using an assay that provides a higher accuracy or precision (for example, by generating a greater number of quantifiable products, such as sequencing reads). The statistical analysis can be repeated, which can reveal whether, given the subsequent statistical results, a call of normal or abnormal for the test chromosome or portion thereof can be made within the desired level of confidence.

FIG. 1 illustrates the impact of fetal fraction and assay depth (specifically sequencing read depth) on resolving a triploid test chromosome (chromosome 21 in the illustrated example) dosage and an expected test chromosome dosage (which is expected to be diploid). In the example illustrated in FIG. 1, the test chromosome dosage is measured by aligning sequencing reads from the test chromosome; binning the aligned sequencing reads in a plurality of bins; counting the number of sequencing reads in each bin, including normalizing the number of sequencing reads in each bin for GC content and mappability; and determining a distribution for the number of reads per bin. The distribution for the aneuploid test chromosome and the expected distribution for the test chromosome (assuming disomy) is plotted (number of bins versus reads per bin). When the fetal fraction of cfDNA is high (right side of the figure), the sequencing depth needed to resolve the measured and expected test chromosomes is relatively low. However, when the fetal fraction of cfDNA is low (left side of figure) the sequencing depth needed to statistically distinguish the measured from the expected test chromosomes is relatively high.

Since the majority of test maternal samples will likely not require re-measurement of the test chromosome dosage, the subsequent assay may only need to be applied to a limited number of samples. By employing these methods, the cost for the noninvasive prenatal screen is more efficient (both in terms of cost and time) by minimizing the average assay depth while also yielding high sensitivity and specificity even at fetal fractions below which other noninvasive methods are able to call a normal or abnormal fetal chromosome within the desired confidence level. Because clinical guidelines recommend offering invasive diagnostic testing in the case of no-call (due to higher rates of aneuploidy in these samples), the reduced no-call rate from the methods provided herein helps reduce patient anxiety, unnecessary invasive procedures, and clinical workload burden.

Figure 11:
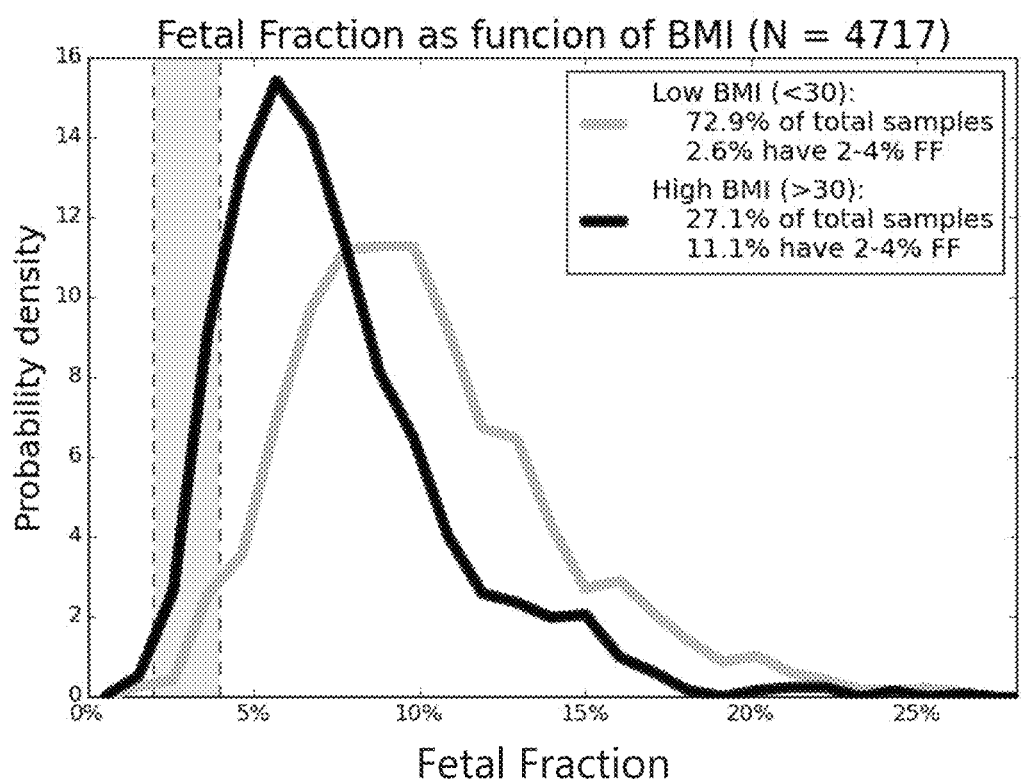
FIG. 11 compares the distribution of fetal fraction among pregnant women with a high body mass index (BMI) (>30) and a low BMI (<30).

Fetal fraction is influenced, in part, by the gestational age of the fetus and by the proportional size of the mother relative to the fetus. Pregnant women with a high body mass index (BMI) tend to have a lower fetal fraction at a similar gestational age. For example, as shown in FIG. 11, women with a BMI greater than 30 are four times as likely to have a low fetal fraction of 2% to 4% (0.35 to 3.8 percentile) as women with a BMI under 30. In some embodiments, the woman carrying the fetus has a BMI of about 25 or higher, about 30 or higher, about 30 or higher, about 35 or higher, or about 40 or higher. In some embodiments, the woman carrying the fetus has a BMI of about 25 to about 50 (such as about 30 to about 40, about 30 to about 35, or about 35 to about 40). In some embodiments, the method includes selecting a test maternal sample from a woman carrying a fetus with a BMI of about 25 or higher, about 30 or higher, about 35 or higher, or about 40 or higher, or with a BMI of about 25 to about 50 (such as about 30 to about 40, about 30 to about 35, or about 35 or about 40), and performing the method for determining a chromosomal abnormality (such as aneuploidy) on the selected test maternal sample. Previous methods of noninvasive prenatal screening for aneuploidy are thus less likely to be useful for pregnant women with high BMI, or any other pregnant woman with a low fetal fraction of cfDNA. Furthermore, fetuses with chromosomal aneuploidy or certain microdeletions are more often undersized, further decreasing the fetal fraction of cfDNA.

The methods described herein are more robust, and can more reliably provide screening for pregnant women with a high BMI, fetus with developmental anomalies, and at a younger gestational age. In some embodiments of the methods described herein, the methods allow for accurate screening of fetal aneuploidy using a test maternal sample from about 99.65 percent of pregnant women.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

The term "average" as used herein refers to either a mean or a median, or any value used to approximate the mean or the median. An "average mean" or "average median" refers to a mean or median (or any value used to approximate the mean or the median) of the means or medians (or approximate means or medians) from a plurality of distributions. An "average variation" refers to a mean or median (or any value used to approximate the mean or the median) of variations from a plurality of distributions. An "average distribution" refers to i) an average mean or an average median, and ii) an average variation, from a plurality of distributions.

A "bin" is an arbitrary genomic region from which a quantifiable measurement can be made. When multiple bins (i.e., a plurality of bins) are subjected to common analysis, the length of each arbitrary genomic region is preferably the same and tiled across a region of interest without overlaps. Nevertheless, the bins can be of different lengths, and can be tiled across the region of interest with overlaps or gaps.

A "chromosome dosage" is a quantitated amount of a chromosome, measured directly or indirectly, or a quantitated amount of an assay product representing a chromosome. The chromosome dosage may be represented as an absolute amount or as a distribution (including a mean or median (or an approximate value representing the mean or the median) and a variation). The chromosome dosage can be an integer (such as an integer number of chromosomes or an integer number of assay products) or a fraction (such as an amount of a chromosome indirectly measured based on a quantitated amount of an assay product representing the chromosome or a normalized amount of the assay product representing the chromosome).

An "expected chromosome dosage" is a chromosome dosage that would be expected if no fetal chromosomal abnormality were present.

A "fetal chromosomal abnormality" is any chromosomal copy number variant of the fetal genome relative to the maternal genome, including a microdeletion or chromosomal aneuploidy.

An "interrogated region" is any portion of a genome, which may be contiguous or non-contiguous, and can include one or more whole chromosomes or any one or more portions of any one or more chromosomes.

A "machine-learning model" is a predictive mathematical model—which may be implemented on a computer system—that uses an observed data set of numerical or categorical data to generate a predicted outcome data set of numerical or categorical data. The model can be "trained" on a plurality of observed data sets, wherein each of the observed data sets has a known outcome data set. Once trained, the model can be applied to a novel observed data set to yield a predicted outcome data set. The term "machine learning model" includes, but is not limited to, a regression model, a linear regression model, a ridge regression model, an elastic-net model, or a random-forest model.

A "mappable" sequencing read is a sequencing read that aligns with a unique location in a genome. A sequencing read that maps to zero or two or more locations in the genome is considered not "mappable."

A "maternal sample" refers to any sample taken from a pregnant mammal which comprises a maternal source and a fetal source of nucleic acids. The term "training maternal sample" refers to a maternal sample that is used to train a machine-learning model.

The term "maternal cell-free DNA" or "maternal cfDNA" refers to a cell-free DNA originating from a chromosome from a maternal cell that is neither placental nor fetal. The term "fetal cell-free DNA" or "fetal cfDNA" refers to a cell-free DNA originating from a chromosome from a placental cell or a fetal cell.

The term "normal" when used to characterize a putative fetal chromosomal abnormality, such as a microdeletion or aneuploidy, indicates that the putative fetal chromosomal abnormality is not present. The term "abnormal" when used to characterize a putative fetal chromosomal abnormality indicates that the putative fetal chromosomal abnormality is present.

A "variation" as used herein refers to any statistical metric that defines the width of a distribution, and can be, but is not limited to, a standard deviation, a variance, or an interquartile range.

A "value of likelihood" refers to any value achieved by directly calculating likelihood or any value that can be correlated to or otherwise indicative of likelihood. The term "value of likelihood" includes an odds ratio.

A "value of statistical significance" is any value that indicates the statistical distance of a tested event or hypothesis from a null or reference hypothesis, such as a Z-score, a p-value, or a probability.

It is understood that aspects and variations of the invention described herein include "consisting" and/or "consisting essentially of" aspects and variations.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention.

The section headings used herein are for organizational purposes only and are not to be construed as limiting the subject matter described.

In one aspect there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA; measuring a fetal fraction of cell-free DNA in the test maternal sample based on a count of binned sequencing reads from an interrogated region from the maternal sample; and determining an initial value of likelihood that the fetal cell-free DNA is abnormal in the test chromosome or the portion thereof based on the measured dosage, an expected dosage of the test chromosome or the portion thereof, and the measured fetal fraction. In some embodiments, the dosage of the test chromosome or the portion thereof and the fetal fraction are measured in a simultaneous assay.

In some embodiments, the value of likelihood is an odds ratio. In some embodiments, the dosage of the test chromosome or the portion thereof is measured by: aligning sequencing reads from the test chromosome or portion thereof; binning the aligned sequencing reads in a plurality of bins; counting the number of sequencing reads in each bin; and determining an average number of reads per bin and a variation of the number of reads per bin. In some embodiments, the expected dosage for the test chromosome or the portion thereof is determined by generating a dosage distribution vector comprising the dosage of at least one chromosome or portion thereof other than the test chromosome or portion thereof for each maternal sample in a plurality of maternal samples; training a machine-learning model by regressing the dosage distribution vector onto the dosage of the test chromosome or portion thereof for each maternal sample in the plurality of maternal samples; and applying the trained machine-learning model to a dosage distribution vector comprising the dosage of the at least one chromosome or portion thereof other than the test chromosome or portion thereof from the maternal sample to obtain the expected dosage for the test chromosome or the portion thereof in the test maternal sample. In some embodiments, the expected dosage for the test chromosome or the portion thereof is determined by: generating an average dosage vector comprising the average number of reads per bin from at least one chromosome or portion thereof other than the test chromosome or portion thereof for each maternal sample in a plurality of maternal samples; training a dosage average machine-learning model by regressing the average dosage vector onto the average number of sequencing reads per bin from the test chromosome or portion thereof for each maternal sample in the plurality of maternal samples; applying the trained dosage average machine-learning model to an average dosage vector comprising the average number of reads per bin from the at least one chromosome or portion thereof other than the test chromosome or portion thereof from the maternal sample to obtain the expected average number of sequencing reads per bin for the test chromosome or the portion thereof in the test maternal sample; generating a dosage variation vector comprising the variation of the number of reads per bin from at least one chromosome or portion thereof other than the test chromosome or portion thereof for each maternal sample in a plurality of maternal samples; training a dosage variation machine-learning model by regressing the dosage variation vector onto the variation of the number of sequencing reads per bin from the test chromosome or portion thereof for each maternal sample in the plurality of maternal samples; and applying the trained dosage variation machine-learning model to a dosage variation vector comprising the variation of the number of reads per bin from the least one chromosome or portion thereof other than the test chromosome or portion thereof from the maternal sample to obtain the expected variation of the number of sequencing reads per bin for the test chromosome or the portion thereof in the test maternal sample. In some embodiments, measuring the fetal fraction comprises: aligning the sequencing reads from the interrogated region; binning the aligned sequencing reads from the interrogated region in a plurality of bins; counting the number of sequencing reads in each of at least a portion of the bins; and determining the measured fetal fraction based on the number of sequencing reads in the at least a portion of the bins using a trained machine learning model. In some embodiments, the machine-learning model is trained by: for each training maternal sample in a plurality of training maternal samples, wherein each training maternal sample has a known fetal fraction of cell-free DNA: aligning sequencing reads from the interrogated region, binning the aligned sequencing reads from the interrogated region in a plurality of bins, and counting the number of sequencing reads in each bin; and determining one or more model coefficients based on the number of sequencing reads in each bin and the known fetal fraction for each training maternal sample in the plurality of training maternal samples. In some embodiments, the test maternal sample is obtained from a woman with a body mass index of about 30 or more. In some embodiments, the method is implemented by a program executed on a computer system. In some embodiments, the method further comprises reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

In another aspect there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA; measuring a fetal fraction of cell-free DNA in the test maternal sample based on a count of binned sequencing reads from an interrogated region from the maternal sample; and determining an initial value of likelihood that the fetal cell-free DNA is abnormal in the test chromosome or the portion thereof by determining an initial value of statistical significance for the test chromosome or the portion thereof based on the measured dosage and the expected dosage; and determining the initial value of likelihood based on the initial value of statistical significance and the measured fetal fraction. In some embodiments, the test chromosome is called as abnormal (such as aneuploid or having a microdeletion) if the absolute value of the initial value of statistical significance is above a predetermined threshold. In some embodiments, the test chromosome is called as normal if the absolute value of the initial value of statistical significance is below a first predetermined threshold and the initial value of likelihood is below a second predetermined threshold. In some embodiments, the dosage of the test chromosome or the portion thereof and the fetal fraction are measured in a simultaneous assay. In some embodiments, the value of statistical significance is a Z-score, a p-value, or a probability. In some embodiments, the value of likelihood is an odds ratio. In some embodiments, the dosage of the test chromosome or the portion thereof is measured by: aligning sequencing reads from the test chromosome or portion thereof; binning the aligned sequencing reads in a plurality of bins; counting the number of sequencing reads in each bin; and determining an average number of reads per bin and a variation of the number of reads per bin. In some embodiments, the expected dosage for the test chromosome or the portion thereof is determined by generating a dosage distribution vector comprising the dosage of at least one chromosome or portion thereof other than the test chromosome or portion thereof for each maternal sample in a plurality of maternal samples; training a machine-learning model by regressing the dosage distribution vector onto the dosage of the test chromosome or portion thereof for each maternal sample in the plurality of maternal samples; and applying the trained machine-learning model to a dosage distribution vector comprising the dosage of the least one chromosome or portion thereof other than the test chromosome or portion thereof from the maternal sample to obtain the expected dosage for the test chromosome or the portion thereof in the test maternal sample. In some embodiments, the expected dosage for the test chromosome or the portion thereof is determined by: generating an average dosage vector comprising the average number of reads per bin from at least one chromosome or portion thereof other than the test chromosome or portion thereof for each maternal sample in a plurality of maternal samples; training a dosage average machine-learning model by regressing the average dosage vector onto the average number of sequencing reads per bin from the test chromosome or portion thereof for each maternal sample in the plurality of maternal samples; applying the trained dosage average machine-learning model to an average dosage vector comprising the average number of reads per bin from the least one chromosome or portion thereof other than the test chromosome or portion thereof from the maternal sample to obtain the expected average number of sequencing reads per bin for the test chromosome or the portion thereof in the test maternal sample; generating a dosage variation vector comprising the variation of the number of reads per bin from at least one chromosome or portion thereof other than the test chromosome or portion thereof for each maternal sample in a plurality of maternal samples; training a dosage variation machine-learning model by regressing the dosage variation vector onto the variation of the number of sequencing reads per bin from the test chromosome or portion thereof for each maternal sample in the plurality of maternal samples; and applying the trained dosage variation machine-learning model to a dosage variation vector comprising the variation of the number of reads per bin from the least one chromosome or portion thereof other than the test chromosome or portion thereof from the maternal sample to obtain the expected variation of the number of sequencing reads per bin for the test chromosome or the portion thereof in the test maternal sample. In some embodiments, measuring the fetal fraction comprises: aligning the sequencing reads from the interrogated region; binning the aligned sequencing reads from the interrogated region in a plurality of binds; counting the number of sequencing reads in each of at least a portion of the bins; and determining the measured fetal fraction based on the number of sequencing reads in the at least a portion of the bins using a trained machine learning model. In some embodiments, the machine-learning model is trained by: for each training maternal sample in a plurality of training maternal samples, wherein each training maternal sample has a known fetal fraction of cell-free DNA: aligning sequencing reads from the interrogated region, binning the aligned sequencing reads from the interrogated region in a plurality of bins, and counting the number of sequencing reads in each bin; and determining one or more model coefficients based on the number of sequencing reads in each bin and the known fetal fraction for each training maternal sample in the plurality of training maternal samples. In some embodiments, the test maternal sample is obtained from a woman with a body mass index of about 30 or more. In some embodiments, the method is implemented by a program executed on a computer system. In some embodiments, the method further comprises reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

In another aspect there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA, wherein the dosage is measured using an initial assay that generates an initial plurality of sequencing reads, wherein the number of sequencing reads in the initial plurality indicates the measured dosage; measuring a fetal fraction of cell-free DNA in the test maternal sample based on a count of binned sequencing reads from an interrogated region from the maternal sample; and determining an initial value of likelihood that the fetal cell-free DNA is abnormal in the test chromosome or the portion thereof by determining an initial value of statistical significance for the test chromosome or the portion thereof based on the measured dosage and the expected dosage; and determining the initial value of likelihood based on the initial value of statistical significance and the measured fetal fraction. In some embodiments, the dosage of the test chromosome or the portion thereof and the fetal fraction are measured in a simultaneous assay. In some embodiments, the value of statistical significance is a Z-score, a p-value, or a probability. In some embodiments, the value of likelihood is an odds ratio. In some embodiments, the dosage of the test chromosome or the portion thereof is measured by: aligning sequencing reads from the test chromosome or portion thereof; binning the aligned sequencing reads in a plurality of bins; counting the number of sequencing reads in each bin; and determining an average number of reads per bin and a variation of the number of reads per bin. In some embodiments, the expected dosage for the test chromosome or the portion thereof is determined by generating a dosage distribution vector comprising the dosage of at least one chromosome or portion thereof other than the test chromosome or portion thereof for each maternal sample in a plurality of maternal samples; training a machine-learning model by regressing the dosage distribution vector onto the dosage of the test chromosome or portion thereof for each maternal sample in the plurality of maternal samples; and applying the trained machine-learning model to a dosage distribution vector comprising the dosage of the least one chromosome or portion thereof other than the test chromosome or portion thereof from the maternal sample to obtain the expected dosage for the test chromosome or the portion thereof in the test maternal sample. In some embodiments, the expected dosage for the test chromosome or the portion thereof is determined by: generating an average dosage vector comprising the average number of reads per bin from at least one chromosome or portion thereof other than the test chromosome or portion thereof for each maternal sample in a plurality of maternal samples; training a dosage average machine-learning model by regressing the average dosage vector onto the average number of sequencing reads per bin from the test chromosome or portion thereof for each maternal sample in the plurality of maternal samples; applying the trained dosage average machine-learning model to an average dosage vector comprising the average number of reads per bin from the least one chromosome or portion thereof other than the test chromosome or portion thereof from the maternal sample to obtain the expected average number of sequencing reads per bin for the test chromosome or the portion thereof in the test maternal sample; generating a dosage variation vector comprising the variation of the number of reads per bin from at least one chromosome or portion thereof other than the test chromosome or portion thereof for each maternal sample in a plurality of maternal samples; training a dosage variation machine-learning model by regressing the dosage variation vector onto the variation of the number of sequencing reads per bin from the test chromosome or portion thereof for each maternal sample in the plurality of maternal samples; and applying the trained dosage variation machine-learning model to a dosage variation vector comprising the variation of the number of reads per bin from the least one chromosome or portion thereof other than the test chromosome or portion thereof from the maternal sample to obtain the expected variation of the number of sequencing reads per bin for the test chromosome or the portion thereof in the test maternal sample. In some embodiments, measuring the fetal fraction comprises: aligning the sequencing reads from the interrogated region; binning the aligned sequencing reads from the interrogated region in a plurality of bins; counting the number of sequencing reads in each of at least a portion of the bins; and determining the measured fetal fraction based on the number of sequencing reads in the at least a portion of the bins using a trained machine learning model. In some embodiments, the machine-learning model is trained by: for each training maternal sample in a plurality of training maternal samples, wherein each training maternal sample has a known fetal fraction of cell-free DNA: aligning sequencing reads from the interrogated region, binning the aligned sequencing reads from the interrogated region in a plurality of bins, and counting the number of sequencing reads in each bin; and determining one or more model coefficients based on the number of sequencing reads in each bin and the known fetal fraction for each training maternal sample in the plurality of training maternal samples. In some embodiments, the test maternal sample is obtained from a woman with a body mass index of about 30 or more. In some embodiments, the method is implemented by a program executed on a computer system. In some embodiments, the method further comprises reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

In another aspect there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA, wherein the dosage is measured using an initial assay that generates an initial plurality of sequencing reads, wherein the number of sequencing reads in the initial plurality indicates the measured dosage; measuring a fetal fraction of cell-free DNA in the test maternal sample based on a count of binned sequencing reads from an interrogated region from the maternal sample; and determining an initial value of likelihood that the fetal cell-free DNA is abnormal in the test chromosome or the portion thereof by determining an initial value of statistical significance for the test chromosome or the portion thereof based on the measured dosage and the expected dosage; determining the initial value of likelihood based on the initial value of statistical significance and the measured fetal fraction; re-measuring the dosage of the test chromosome or the portion thereof using a subsequent assay that generates a subsequent plurality of sequencing reads from the test chromosome or portion thereof if the initial value of likelihood is above a predetermined threshold; and determining a subsequent value of statistical significance for the test chromosome or the portion thereof based on the re-measured dosage. In some embodiments, the test chromosome or portion thereof is called abnormal (such as aneuploid or having a microdeletion) if the absolute value of the subsequent value of statistical significance is above a predetermined threshold. In some embodiments, the method further comprises determining a subsequent value of likelihood that the fetal cell-free DNA is abnormal for the test chromosome or the portion thereof based on the re-measured dosage, the expected dosage of the test chromosome or portion thereof, and the measured fetal fraction. In some embodiments, the test chromosome or portion thereof is called as normal if the subsequent value of likelihood is below a predetermined threshold. In some embodiments, the dosage of the test chromosome or the portion thereof and the fetal fraction are measured in a simultaneous assay. In some embodiments, the value of statistical significance is a Z-score, a p-value, or a probability. In some embodiments, the value of likelihood is an odds ratio. In some embodiments, the dosage of the test chromosome or the portion thereof is measured by: aligning sequencing reads from the test chromosome or portion thereof; binning the aligned sequencing reads in a plurality of bins; counting the number of sequencing reads in each bin; and determining an average number of reads per bin and a variation of the number of reads per bin. In some embodiments, the expected dosage for the test chromosome or the portion thereof is determined by generating a dosage distribution vector comprising the dosage of at least one chromosome or portion thereof other than the test chromosome or portion thereof for each maternal sample in a plurality of maternal samples; training a machine-learning model by regressing the dosage distribution vector onto the dosage of the test chromosome or portion thereof for each maternal sample in the plurality of maternal samples; and applying the trained machine-learning model to a dosage distribution vector comprising the dosage of the least one chromosome or portion thereof other than the test chromosome or portion thereof from the maternal sample to obtain the expected dosage for the test chromosome or the portion thereof in the test maternal sample. In some embodiments, the expected dosage for the test chromosome or the portion thereof is determined by: generating an average dosage vector comprising the average number of reads per bin from at least one chromosome or portion thereof other than the test chromosome or portion thereof for each maternal sample in a plurality of maternal samples; training a dosage average machine-learning model by regressing the average dosage vector onto the average number of sequencing reads per bin from the test chromosome or portion thereof for each maternal sample in the plurality of maternal samples; applying the trained dosage average machine-learning model to an average dosage vector comprising the average number of reads per bin from the least one chromosome or portion thereof other than the test chromosome or portion thereof from the maternal sample to obtain the expected average number of sequencing reads per bin for the test chromosome or the portion thereof in the test maternal sample; generating a dosage variation vector comprising the variation of the number of reads per bin from at least one chromosome or portion thereof other than the test chromosome or portion thereof for each maternal sample in a plurality of maternal samples; training a dosage variation machine-learning model by regressing the dosage variation vector onto the variation of the number of sequencing reads per bin from the test chromosome or portion thereof for each maternal sample in the plurality of maternal samples; and applying the trained dosage variation machine-learning model to a dosage variation vector comprising the variation of the number of reads per bin from the least one chromosome or portion thereof other than the test chromosome or portion thereof from the maternal sample to obtain the expected variation of the number of sequencing reads per bin for the test chromosome or the portion thereof in the test maternal sample. In some embodiments, measuring the fetal fraction comprises: aligning the sequencing reads from the interrogated region; binning the aligned sequencing reads from the interrogated region in a plurality of binds; counting the number of sequencing reads in each of at least a portion of the bins; and determining the measured fetal fraction based on the number of sequencing reads in the at least a portion of the bins using a trained machine learning model. In some embodiments, the machine-learning model is trained by: for each training maternal sample in a plurality of training maternal samples, wherein each training maternal sample has a known fetal fraction of cell-free DNA: aligning sequencing reads from the interrogated region, binning the aligned sequencing reads from the interrogated region in a plurality of bins, and counting the number of sequencing reads in each bin; and determining one or more model coefficients based on the number of sequencing reads in each bin and the known fetal fraction for each training maternal sample in the plurality of training maternal samples. In some embodiments, the test maternal sample is obtained from a woman with a body mass index of about 30 or more. In some embodiments, the method is implemented by a program executed on a computer system. In some embodiments, the method further comprises reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

In another aspect there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA, wherein the dosage is measured using an initial assay that generates an initial plurality of sequencing reads, wherein the number of sequencing reads in the initial plurality indicates the measured dosage; measuring a fetal fraction of cell-free DNA in the test maternal sample based on a count of binned sequencing reads from an interrogated region from the maternal sample; and determining an initial value of likelihood that the fetal cell-free DNA is abnormal in the test chromosome or the portion thereof by determining an initial value of statistical significance for the test chromosome or the portion thereof based on the measured dosage and the expected dosage; determining the initial value of likelihood based on the initial value of statistical significance and the measured fetal fraction; re-measuring the dosage of the test chromosome or the portion thereof using a subsequent assay that generates a subsequent plurality of sequencing reads from the test chromosome if the absolute value of the initial value of statistical significance is below a predetermined threshold; and determining a subsequent value of statistical significance for the test chromosome or the portion thereof based on the re-measured dosage. In some embodiments, the test chromosome or portion thereof is called abnormal (such as aneuploid or having a microdeletion) if the absolute value of the subsequent value of statistical significance is above a predetermined threshold. In some embodiments, the method further comprises determining a subsequent value of likelihood that the fetal cell-free DNA is abnormal for the test chromosome or the portion thereof based on the re-measured dosage, the expected dosage of the test chromosome or portion thereof, and the measured fetal fraction. In some embodiments, the test chromosome or portion thereof is called as normal if the subsequent value of likelihood is below a predetermined threshold. In some embodiments, the dosage of the test chromosome or the portion thereof and the fetal fraction are measured in a simultaneous assay. In some embodiments, the value of statistical significance is a Z-score, a p-value, or a probability. In some embodiments, the value of likelihood is an odds ratio. In some embodiments, the dosage of the test chromosome or the portion thereof is measured by: aligning sequencing reads from the test chromosome or portion thereof; binning the aligned sequencing reads in a plurality of bins; counting the number of sequencing reads in each bin; and determining an average number of reads per bin and a variation of the number of reads per bin. In some embodiments, the expected dosage for the test chromosome or the portion thereof is determined by generating a dosage distribution vector comprising the dosage of at least one chromosome or portion thereof other than the test chromosome or portion thereof for each maternal sample in a plurality of maternal samples; training a machine-learning model by regressing the dosage distribution vector onto the dosage of the test chromosome or portion thereof for each maternal sample in the plurality of maternal samples; and applying the trained machine-learning model to a dosage distribution vector comprising the dosage of the least one chromosome or portion thereof other than the test chromosome or portion thereof from the maternal sample to obtain the expected dosage for the test chromosome or the portion thereof in the test maternal sample. In some embodiments, the expected dosage for the test chromosome or the portion thereof is determined by: generating an average dosage vector comprising the average number of reads per bin from at least one chromosome or portion thereof other than the test chromosome or portion thereof for each maternal sample in a plurality of maternal samples; training a dosage average machine-learning model by regressing the average dosage vector onto the average number of sequencing reads per bin from the test chromosome or portion thereof for each maternal sample in the plurality of maternal samples; applying the trained dosage average machine-learning model to an average dosage vector comprising the average number of reads per bin from the least one chromosome or portion thereof other than the test chromosome or portion thereof from the maternal sample to obtain the expected average number of sequencing reads per bin for the test chromosome or the portion thereof in the test maternal sample; generating a dosage variation vector comprising the variation of the number of reads per bin from at least one chromosome or portion thereof other than the test chromosome or portion thereof for each maternal sample in a plurality of maternal samples; training a dosage variation machine-learning model by regressing the dosage variation vector onto the variation of the number of sequencing reads per bin from the test chromosome or portion thereof for each maternal sample in the plurality of maternal samples; and applying the trained dosage variation machine-learning model to a dosage variation vector comprising the variation of the number of reads per bin from the least one chromosome or portion thereof other than the test chromosome or portion thereof from the maternal sample to obtain the expected variation of the number of sequencing reads per bin for the test chromosome or the portion thereof in the test maternal sample. In some embodiments, measuring the fetal fraction comprises: aligning the sequencing reads from the interrogated region; binning the aligned sequencing reads from the interrogated region in a plurality of binds; counting the number of sequencing reads in each of at least a portion of the bins; and determining the measured fetal fraction based on the number of sequencing reads in the at least a portion of the bins using a trained machine learning model. In some embodiments, the machine-learning model is trained by: for each training maternal sample in a plurality of training maternal samples, wherein each training maternal sample has a known fetal fraction of cell-free DNA: aligning sequencing reads from the interrogated region, binning the aligned sequencing reads from the interrogated region in a plurality of bins, and counting the number of sequencing reads in each bin; and determining one or more model coefficients based on the number of sequencing reads in each bin and the known fetal fraction for each training maternal sample in the plurality of training maternal samples. In some embodiments, the test maternal sample is obtained from a woman with a body mass index of about 30 or more. In some embodiments, the method is implemented by a program executed on a computer system. In some embodiments, the method further comprises reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

In another aspect there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA, wherein the dosage is measured using an initial assay that generates an initial plurality of sequencing reads, wherein the number of sequencing reads in the initial plurality indicates the measured dosage; measuring a fetal fraction of cell-free DNA in the test maternal sample based on a count of binned sequencing reads from an interrogated region from the maternal sample; and determining an initial value of likelihood that the fetal cell-free DNA is abnormal in the test chromosome or the portion thereof by determining an initial value of statistical significance for the test chromosome or the portion thereof based on the measured dosage and the expected dosage; determining the initial value of likelihood based on the initial value of statistical significance and the measured fetal fraction; re-measuring the dosage of the test chromosome or the portion thereof using a subsequent assay that generates a subsequent plurality of quantifiable products from the test chromosome if the initial value of likelihood is above a predetermined threshold and the absolute value of the initial value of statistical significance is below a predetermined threshold; and determining a subsequent value of statistical significance for the test chromosome or the portion thereof based on the re-measured dosage. In some embodiments, the test chromosome or portion thereof is called abnormal (such as aneuploid or having a microdeletion) if the absolute value of the subsequent value of statistical significance is above a predetermined threshold. In some embodiments, the method further comprises determining a subsequent value of likelihood that the fetal cell-free DNA is abnormal for the test chromosome or the portion thereof based on the re-measured dosage, the expected dosage of the test chromosome or portion thereof, and the measured fetal fraction. In some embodiments, the test chromosome or portion thereof is called as normal if the subsequent value of likelihood is below a predetermined threshold. In some embodiments, the dosage of the test chromosome or the portion thereof and the fetal fraction are measured in a simultaneous assay. In some embodiments, the value of statistical significance is a Z-score, a p-value, or a probability. In some embodiments, the value of likelihood is an odds ratio. In some embodiments, the dosage of the test chromosome or the portion thereof is measured by: aligning sequencing reads from the test chromosome or portion thereof; binning the aligned sequencing reads in a plurality of bins; counting the number of sequencing reads in each bin; and determining an average number of reads per bin and a variation of the number of reads per bin. In some embodiments, the expected dosage for the test chromosome or the portion thereof is determined by generating a dosage distribution vector comprising the dosage of at least one chromosome or portion thereof other than the test chromosome or portion thereof for each maternal sample in a plurality of maternal samples; training a machine-learning model by regressing the dosage distribution vector onto the dosage of the test chromosome or portion thereof for each maternal sample in the plurality of maternal samples; and applying the trained machine-learning model to a dosage distribution vector comprising the dosage of the least one chromosome or portion thereof other than the test chromosome or portion thereof from the maternal sample to obtain the expected dosage for the test chromosome or the portion thereof in the test maternal sample. In some embodiments, the expected dosage for the test chromosome or the portion thereof is determined by: generating an average dosage vector comprising the average number of reads per bin from at least one chromosome or portion thereof other than the test chromosome or portion thereof for each maternal sample in a plurality of maternal samples; training a dosage average machine-learning model by regressing the average dosage vector onto the average number of sequencing reads per bin from the test chromosome or portion thereof for each maternal sample in the plurality of maternal samples; applying the trained dosage average machine-learning model to an average dosage vector comprising the average number of reads per bin from the least one chromosome or portion thereof other than the test chromosome or portion thereof from the maternal sample to obtain the expected average number of sequencing reads per bin for the test chromosome or the portion thereof in the test maternal sample; generating a dosage variation vector comprising the variation of the number of reads per bin from at least one chromosome or portion thereof other than the test chromosome or portion thereof for each maternal sample in a plurality of maternal samples; training a dosage variation machine-learning model by regressing the dosage variation vector onto the variation of the number of sequencing reads per bin from the test chromosome or portion thereof for each maternal sample in the plurality of maternal samples; and applying the trained dosage variation machine-learning model to a dosage variation vector comprising the variation of the number of reads per bin from the least one chromosome or portion thereof other than the test chromosome or portion thereof from the maternal sample to obtain the expected variation of the number of sequencing reads per bin for the test chromosome or the portion thereof in the test maternal sample. In some embodiments, measuring the fetal fraction comprises: aligning the sequencing reads from the interrogated region; binning the aligned sequencing reads from the interrogated region in a plurality of binds; counting the number of sequencing reads in each of at least a portion of the bins; and determining the measured fetal fraction based on the number of sequencing reads in the at least a portion of the bins using a trained machine learning model. In some embodiments, the machine-learning model is trained by: for each training maternal sample in a plurality of training maternal samples, wherein each training maternal sample has a known fetal fraction of cell-free DNA: aligning sequencing reads from the interrogated region, binning the aligned sequencing reads from the interrogated region in a plurality of bins, and counting the number of sequencing reads in each bin; and determining one or more model coefficients based on the number of sequencing reads in each bin and the known fetal fraction for each training maternal sample in the plurality of training maternal samples. In some embodiments, the test maternal sample is obtained from a woman with a body mass index of about 30 or more. In some embodiments, the method is implemented by a program executed on a computer system. In some embodiments, the method further comprises reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

In another aspect, there is provided a method for determining a fetal chromosomal abnormality in a test chromosome or a portion thereof by analyzing a test maternal sample, comprising: measuring a dosage of the test chromosome or the portion thereof in the test maternal sample comprising fetal cell-free DNA and maternal cell-free DNA; measuring a fetal fraction of cell-free DNA in the test maternal sample based on a count of binned sequencing reads from an interrogated region from the maternal sample; and determining an initial value of statistical significance for the test chromosome or the portion thereof based on the measured dosage and an expected dosage of the test chromosome or the portion thereof. In some embodiments, the method further comprises calling the test chromosome or portion thereof to be abnormal (such as aneuploid or having a microdeletion) if the initial value of statistical significance is above a first predetermined threshold. In some embodiments, the dosage of the test chromosome or the portion thereof and the fetal fraction are measured in a simultaneous assay. In some embodiments, the value of statistical significance is a Z-score, a p-value, or a probability. In some embodiments, the value of likelihood is an odds ratio. In some embodiments, the dosage of the test chromosome or the portion thereof is measured by: aligning sequencing reads from the test chromosome or portion thereof; binning the aligned sequencing reads in a plurality of bins; counting the number of sequencing reads in each bin; and determining an average number of reads per bin and a variation of the number of reads per bin. In some embodiments, the expected dosage for the test chromosome or the portion thereof is determined by generating a dosage distribution vector comprising the dosage of at least one chromosome or portion thereof other than the test chromosome or portion thereof for each maternal sample in a plurality of maternal samples; training a machine-learning model by regressing the dosage distribution vector onto the dosage of the test chromosome or portion thereof for each maternal sample in the plurality of maternal samples; and applying the trained machine-learning model to a dosage distribution vector comprising the dosage of the least one chromosome or portion thereof other than the test chromosome or portion thereof from the maternal sample to obtain the expected dosage for the test chromosome or the portion thereof in the test maternal sample. In some embodiments, the expected dosage for the test chromosome or the portion thereof is determined by: generating an average dosage vector comprising the average number of reads per bin from at least one chromosome or portion thereof other than the test chromosome or portion thereof for each maternal sample in a plurality of maternal samples; training a dosage average machine-learning model by regressing the average dosage vector onto the average number of sequencing reads per bin from the test chromosome or portion thereof for each maternal sample in the plurality of maternal samples; applying the trained dosage average machine-learning model to an average dosage vector comprising the average number of reads per bin from the least one chromosome or portion thereof other than the test chromosome or portion thereof from the maternal sample to obtain the expected average number of sequencing reads per bin for the test chromosome or the portion thereof in the test maternal sample; generating a dosage variation vector comprising the variation of the number of reads per bin from at least one chromosome or portion thereof other than the test chromosome or portion thereof for each maternal sample in a plurality of maternal samples; training a dosage variation machine-learning model by regressing the dosage variation vector onto the variation of the number of sequencing reads per bin from the test chromosome or portion thereof for each maternal sample in the plurality of maternal samples; and applying the trained dosage variation machine-learning model to a dosage variation vector comprising the variation of the number of reads per bin from the least one chromosome or portion thereof other than the test chromosome or portion thereof from the maternal sample to obtain the expected variation of the number of sequencing reads per bin for the test chromosome or the portion thereof in the test maternal sample. In some embodiments, measuring the fetal fraction comprises: aligning the sequencing reads from the interrogated region; binning the aligned sequencing reads from the interrogated region in a plurality of binds; counting the number of sequencing reads in each of at least a portion of the bins; and determining the measured fetal fraction based on the number of sequencing reads in the at least a portion of the bins using a trained machine learning model. In some embodiments, the machine-learning model is trained by: for each training maternal sample in a plurality of training maternal samples, wherein each training maternal sample has a known fetal fraction of cell-free DNA: aligning sequencing reads from the interrogated region, binning the aligned sequencing reads from the interrogated region in a plurality of bins, and counting the number of sequencing reads in each bin; and determining one or more model coefficients based on the number of sequencing reads in each bin and the known fetal fraction for each training maternal sample in the plurality of training maternal samples. In some embodiments, the test maternal sample is obtained from a woman with a body mass index of about 30 or more. In some embodiments, the method is implemented by a program executed on a computer system. In some embodiments, the method further comprises reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

Measuring Fetal Fraction

Certain regions of a genome may be over- or under-represented in the amount of fetal cell-free DNA versus maternal cell-free DNA. The amount of the over- or under-representation within these regions is proportional to the fetal fraction of cell-free DNA. Not all regions of the genome are over- or under-represented proportional to the fetal fraction of cfDNA. By binning the genome, or a portion thereof (such as an interrogated region, such as one or more chromosomes or a portion thereof), discreet portions of the genome can be isolated so that those specific regions can independently influence a machine-learning model. Measuring the amount of over- or under-representation of those regions can thus be used to indirectly measure the fetal fraction of cfDNA in a maternal sample by applying a trained machine-learning model.

In some embodiments, the fetal fraction of the cell-free DNA in a maternal sample is measured based on the over- or under-representation of fetal cell-free DNA from a plurality of bins within an interrogated region relative to maternal cell-free DNA. In some embodiments, the over- or under-representation of the fetal cell-free DNA is determined by a count of binned sequencing reads. In some embodiments, the over- or under-representation of the fetal cell-free DNA is determined by a count of binned hybridized probes.

In some embodiments, the fetal fraction of the cell-free DNA in a maternal sample is measured based on a count of binned sequencing reads from an interrogated region in the maternal sample. In some embodiments, the sequencing reads are aligned (for example, using a reference sequence), binned in a plurality of bins after being aligned, and the number of sequencing reads in each bin are counted. In some embodiments, the counted sequencing reads are normalized, for example to account for variations in GC content or mappability of the sequencing reads. Binning of the sequencing reads isolates discrete portions of the genome so that those specific regions can independently influence the trained model.

In some embodiments, the fetal fraction of the cell-free DNA in a maternal sample is measured based on a count of binned hybridized probes from an interrogated region in the maternal sample. In some embodiments, a plurality of probes hybridize to an interrogated region, the interrogated region is binned, and the number (or density) of probes that hybridize in each bin is counted. In some embodiments, the number or density of probes is determined using a fluorescence assay. In some embodiments, the probes are bound to a microarray.

A trained machine-learning model (such as a regression model, for example a linear regression model or a ridge regression model) is used to determine the measured fetal fraction based on the number of counts (e.g., sequencing reads or hybridized probes) in each of the bins. For example, the number of counts in the bin can be used to form a bin-count vector for any given test maternal sample, which is inputted into a trained machine-learning model to determine the fetal fraction. Optionally, the trained machine-model is a ridge regression model corrected by polynomial smoothing and/or an error reduction scaling process.

The machine-learning model can be trained using a training set. The training set includes a plurality of maternal samples (i.e., training maternal samples), wherein each training maternal sample has a known fetal fraction of cell-free DNA. One or more model coefficients can be determined based on the number of counts (such as sequencing reads or hybridized probes) in each bin and the known fetal fraction for each training maternal sample in the plurality of training maternal samples. The trained model can then be applied to the test maternal sample, which can indirectly measure the fetal fraction in the test maternal sample. The known fetal fraction from the training maternal samples can be determined, for example, by relying on the proportion of Y chromosome, the methylation differential between maternal and fetal cell-free DNA, the distribution of cfDNA fragment lengths, by sequencing polymorphic loci, or by any other known method.

In some embodiments, a sequencing library from each of the training maternal samples is prepared using cell-free DNA from the pregnant woman's serum. The cell-free DNA includes both maternal cell-free DNA and fetal cell-free DNA. The sequencing library is then sequenced (for example, using massive parallel sequencing, such as on an Illumina HiSeq 2500) to generate a plurality of sequencing counts. In some embodiments, the whole genome is sequenced, and in some embodiments, a portion of the genome is sequenced. The portion of the genome can be, for example, one or more chromosomes or one or more portions of one or more chromosomes. In some embodiments, the sequencing reads are about 10 to about 1000 bases in length (such as about 10 to about 14 bases in length, about 14 to about 18 bases in length, about 18 to about 22 bases in length, about 22 to about 26 bases in length, about 26 to about 30 bases in length, about 30 to about 38 bases in length, about 38 to about 46 bases in length, about 46 to about 60 bases in length, about 60 to about 100 bases in length, about 100 to about 200 bases in length, about 200 to about 400 bases in length, about 400 to about 600 bases in length, about 600 to about 800 bases in length, or about 800 to about 1000 bases in length). In some embodiments, the sequencing reads are single-end reads and in some embodiments, the sequencing reads are paired-end reads. Sequencing paired end reads allows for the determination of the length of sequenced cell-free DNA. This information can be beneficial in training the machine-learning model, since maternal cell-free DNA is often, on average, longer than fetal cell-free DNA, and this differential can be used to determine fetal fraction. However, it has been found that training the machine-learning model using paired-end reads is not necessary, and substantial information can be gained from single-end reads alone. As single-end reads provide substantial time and cost savings, single-end reads are preferred.

The sequencing reads from an interrogated region from the training maternal samples are then aligned, for example using one or more reference sequences (such as a human reference genome). The interrogated region is those portions of the sequenced genome from the training maternal samples that are used to train the machine-learning model (e.g., the linear regression model or the ridge regression model). In some embodiments, the interrogated region is the whole genome. In some embodiments, the interrogated region excludes the X chromosome or the Y chromosome. In some embodiments, the interrogated region excludes the chromosome being tested for aneuploidy, such as chromosome 13, 18, or 21. In some embodiments, the interrogated region is one or more chromosomes, or one or more portions of one or more chromosomes. For example, the interrogated region can be a plurality of predetermined bins, which may be on the same chromosome or on different chromosomes.

The aligned sequencing reads from the interrogated region are binned in a plurality of bins. The bins are discrete regions along the genome or chromosome. Smaller bins provide higher resolution of the interrogated region. In some embodiments, the bins are about 1 base to about 1 chromosome in length (such as about 1 kilobases to about 200 kilobases in length (such as about 1 kilobases to about 5 kilobases, about 5 kilobases to about 10 kilobases, about 10 kilobases to about 20 kilobases, about 20 kilobases to about 50 kilobases, about 50 kilobases to about 100 kilobases, or about 100 kilobases to about 200 kilobases). In some embodiments, the interrogated region comprises about 100 bins to about 100,000 bins (such as between about 50 bins and about 100 bins, between about 100 bins and about 200 bins, between about 200 bins and about 500 bins, between about 500 bins and about 1000 bins, between about 1000 bins and about 2000 bins, between about 2000 bins and about 5000 bins, between about 5000 bins and about 10,000 bins, between about 10,000 bins and about 20,000 bins, between about 20,000 bins and about 40,000 bins, between about 40,000 bins and about 60,000 bins, between about 60,000 bins and about 80,000 bins, or between about 80,000 bins and about 100,000 bins). Preferably, the bins are of equal size.

The number of sequencing reads in each bin within the interrogated region for each training sample is counted. The counted sequencing reads for each bin are optionally normalized. Normalization can account for variations in GC content or mappability of the reads between the bins. For example, some bins within the interrogated region may have a higher GC content than other bins within the interrogation region. The higher GC content may increase or decrease the sequencing efficiency within that bin, inflating the relative number of sequencing reads for reasons other than fetal fraction. Methods to normalize GC content are known in the art, for example as described in Fan & Quake, PLoS ONE, vol. 5, e10439 (2010). Similarly, the certain bins within the interrogated region may be more easily mappable (or alignable to the reference interrogated region), and a number of sequencing reads may be excluded, thereby deflating the relative number of sequencing reads for reasons other than fetal fraction. Mappability at a given position in the genome can be predetermined for a given read length, k, by segmenting every position within the interrogated region into k-mers and aligning the sequences back to the interrogated region. K-mers that align to a unique position in the interrogated region are labeled "mappable," and k-mers that no not align to a unique position in the interrogated region are labeled "not mappable." A given bin can be normalized for mappability by scaling the number of reads in the bin by the inverse of the fraction of the mappable k-mers in the bin. For example, if 50% of k-mers within a bin are mappable, the number of observed reads from within that bin are scaled by a factor of 2. Normalization can also optionally include scaling the number of sequencing reads in each bin, for example by dividing the number of sequencing reads in each bin by the average of sequencing reads for the bins within the interrogated region.

For each training maternal sample, the numbers of sequencing reads (which may be normalized) for each bin are associated with a known fetal fraction of cell-free DNA for that training sample. The known fetal fraction may be determined using the chromosome dosage of the Y chromosome or the X chromosome (or both) of the training maternal sample. The chromosome dosage may be determined, for example, by aligning sequencing reads from the X or Y chromosome, which may be obtained simultaneously to the sequencing reads used for the interrogated regions. Because males have one Y chromosome and one X chromosome, whereas the pregnant mother has two X chromosomes and no Y chromosomes, the sequencing read density (i.e., reads per bin) of the X chromosome in male pregnancies should be (1−e/2) relative to female pregnancies, wherein e is the fetal fraction of cell-free DNA (conversely, for the Y chromosome, the sequencing read density is (1+e/2)). The fetal dosage may be determined, for example, using the methods described in Fan & Quake, PLoS ONE, vol. 5, e10439 (2010) or U.S. Patent App. No. US 2010/0112575. In some embodiments, the sequencing reads for the X chromosome or the Y chromosome are aligned (for example, using a reference X chromosome or reference Y chromosome), the aligned sequencing reads are binned, and the number of sequencing reads in each bin are counted. In some embodiments, the numbers of sequencing reads are normalized, for example to account for variations in GC content or mappability. In some embodiments, the numbers of sequencing reads are scaled, for example by dividing by the average or median number of sequencing reads. In some embodiments, the fetal fraction is determined on the basis of the Y chromosome and the X chromosome separately. In some embodiments, to account for any systematic discrepancies between the calculation of fetal fraction from the X chromosome and the Y chromosome, the general relationship between fetal fraction inferred from the Y chromosome and the fetal fraction inferred from the X chromosome is modeled using a linear fit. The slope and intercept of the linear fit is used to scale the fetal fraction inferred from the X chromosome, and the known fetal fraction is the average of the fetal fraction inferred from the Y chromosome and the scaled fetal fraction inferred from the X chromosome (it works similarly well to perform scaling on fetal fraction estimated from the Y chromosome and then average the scaled Y-chromosome fetal fraction with the X-chromosome fetal fraction). Alternative methods of determining fetal fraction for the training maternal samples include methods relying on differential methylation of the maternal and fetal cell-free DNA or polymorphic loci.

The training maternal samples are preferably derived from male pregnancies (that is, a woman pregnant with a male fetus). In some embodiments, fetal fraction determined from the Y chromosome (i.e., $FF_Y$) and fetal fraction from the X chromosome (i.e., $FF_X$) can be determined separately. Optionally, an inferred fetal fraction from the X chromosome ($FF_{IX}$) is determined. An inferred fetal fraction from the X chromosome is generally preferable because it can provide more accurate fetal fraction determinations. $FF_{IX}$ can be determined by using a linear fit to model the relationship between $FF_Y$ and $FF_X$ for a plurality of the training maternal samples. A slope and intercept can be determined for the linear fit, and $FF_X$ can be used as an independent variable to determine the dependent variable $FF_{IX}$. The average of $FF_Y$ and $FF_{IX}$ (or $FF_Y$ and $FF_X$, if $FF_{IX}$ is not used) can be determined, which can be used as the fetal fraction for the training maternal samples (that is, the observed fetal fraction, $FF_O$, for the training maternal samples). Although the observed fetal fraction is preferably determined using the fetal fraction determined from the X chromosome and the fetal fraction determined from the Y chromosome, in some embodiments the observed fetal fraction is determined only from the X chromosome or only from the Y chromosome.

The machine-learning model can be, for example, a regression model, such as a multivariate linear regression model or a multivariate ridge regression model. The machine-learning model can be trained to determine one or more model coefficients using the training maternal samples, each with a known fetal fraction and a vector including the sequencing read counts (which may be normalized) for the bins in the interrogation region. Exemplary linear regression models include elastic net (Enet) and reduced-rank regression with the rank estimated using the weighted rank selection criterion (WRSC), and further detailed in Kim et al., Prenatal Diagnosis, vol. 35, pp. 810-815 (2015) (including Supporting Information).

The machine-learning model can be trained using the fetal fraction and the bin counts (which may be normalized bin counts, or $\log_2$ normalized bin counts) from the training maternal samples. The machine-learning model can be, for example, a linear model defined by:

$$FF_{i,regressed} = \vec{\beta} * \vec{x}_i + c$$

wherein $FF_{i,regressed}$ is the fetal fraction determined by the linear model, $\vec{x}_i$ is the bin-count vector for sample i, $\vec{\beta}$ is a regression coefficient vector, and c is the intercept of the model. The regression coefficient and the intercept can be determined by training the machine-learning model on the training maternal samples, for example, by linear regression or ridge regression. For example, the regression coefficient and the intercept can be determined by minimizing the square error with $L_2$ norm regularization with magnitude α according to:

$$\vec{\beta}, c = \operatorname{argmin}_{\beta, c} \Sigma_i (FF_{i,regressed} - FF_{i,})^2 + \alpha \|\vec{\beta}\|^2$$

In some embodiments, the process of determining the regression coefficient includes scaling the bin counts ($d_{i,j}$) such that the median is set to 0 and the variance (e.g., the interquartile range) is set to 1 for each bin j across all training maternal samples used to train the machine-learning model (also referred to as a robust scalar transform). In some embodiments, the machine-learning model is trained using ridge regression. The ridge parameter α can be set by the user. Since the machine-learning model is underdetermined (that is, there are more bin count variables than fetal fraction outputs), the confidence in the model coefficients can be determined using a randomized k-fold validation (e.g., 10-fold validation) to iteratively determine the coefficients. For example, 90% of the training maternal samples (randomly selected) can be used for any given iteration, and the coefficients can be determined for 10 iterations with training maternal samples randomly selected for each iteration. In some embodiments, the regression model (such as a ridge regression model) is corrected by polynomial smoothing and/or an error reduction scaling process.

Polynomial smoothing of the trained machine-learning model can further improve the determined fetal fraction. Polynomial smoothing helps remove systematic bias artifacts. In some embodiments, a third-order polynomial is used to correct bias in the trained machine-learning model to arrive at a corrected fetal fraction (e.g., $FF_{corrected}$):

$$FF_{corrected} = c_0 + c_1 FF_{regressed} + c_2 FF_{regressed}^2 + c_3 FF_{regressed}^3$$

In some embodiments, the fetal fraction is corrected using a scalar error reduction process (which may be employed in addition to or in place of the polynomial smoothing of the trained machine-learning model). The machine-learning model may over or under predict the regressed or corrected fetal fraction ($FF_{regressed}$ or $FF_{corrected}$) of male or female pregnancies. To account for this, the regressed or corrected fetal fraction of the male or the female pregnancies can be multiplied by a scalar factor η. For example, in some embodiments, the fetal fraction for female pregnancies is under-predicted, and an inferred fetal fraction ($FF_{inferred}$) can be determined from the regressed or corrected fetal fraction as follows:

$$FF_{inferred}^{XY} = FF_{corrected}^{XY}$$

$$FF_{inferred}^{XX} = \eta FF_{corrected}^{XX}$$

where:

$$\eta = \frac{\operatorname{average}(FF_{corrected}^{XY})}{\operatorname{average}(FF_{corrected}^{XX})}$$

The average fetal fraction can be a median fetal fraction or a mean fetal fraction.

The trained machine-learning model can be used to estimate the fetal fraction of a test maternal sample. The test maternal sample may be from a woman with a male or female pregnancy. The fetal fraction of cell-free DNA in the test maternal sample is measured based on a count of binned sequencing reads from the interrogated region from the maternal sample. In some embodiments, a sequencing library is formed from the cell-free DNA from the test maternal sample. The sequencing library is then sequenced, for example using massive parallel sequencing (such as on an Illumina HiSeq 2500) to generate a plurality of sequencing counts. In some embodiments, the whole genome is sequenced, and in some embodiments, a portion of the genome is sequenced. The portion of the genome can be, for example, one or more chromosomes or one or more portions of one or more chromosomes. Preferably, the same portions of the genome of the test maternal sample are sequenced as for the training maternal samples. Further, it is preferable that the sequencing reads should be the same length as used to sequence the training maternal samples. The sequencing reads can be paired-end reads or single-end reads, although single-end reads are generally preferred for efficiency.

The sequencing reads from the interrogated region of the test maternal sample are aligned, for example using one or more reference sequences. Preferably, the same reference sequence or sequences are used to align the test maternal sample as the training maternal sample. The aligned sequencing reads from the test maternal sample are binned using the same bin characteristics (that is, number of bins, size of bins, and location of bins).

The number of sequencing reads in each bin within the interrogated region for each test maternal sample is counted. If the counted sequencing reads for each bin are normalized for the training maternal samples, then the counted sequencing reads for the test maternal samples are similarly normalized. Normalization can account for variations in GC content or mappability of the reads between the bins. Normalization can also include scaling the number of sequencing reads in each bin, for example by dividing the number of sequencing reads in each bin by the mean or median number of sequencing reads for the bins within the interrogated region.

The number of sequencing reads in each bin of the interrogated region of the test maternal sample (which may be normalized) can then be received by the trained machine-learning model (e.g., the linear regression model or the ridge regression model), which outputs the indirectly measured fetal fraction for the test maternal sample. The measured fetal fraction of the test maternal sample can be corrected using the polynomial smoothing process (e.g., the third-order polynomial determined) or the scalar error reduction using the predetermined scalar factor η. In some embodiments, the measured fetal fraction of the test sample can be the regressed fetal fraction, the corrected fetal fraction, or the inferred fetal fraction.

Accurate fetal fraction for the test maternal sample can be measured at low sequencing depth. In some embodiments, the test maternal sample is sequenced at a genome-wide sequencing depth of about 6 million sequencing reads or more (such as about 7 million sequencing reads or more, about 8 million sequencing reads or more, about 9 million sequencing reads or more, about 10 million sequencing reads or more, about 11 million sequencing reads or more, about 12 million sequencing reads or more, about 13 million sequencing reads or more, about 14 million sequencing reads or more, or about 15 million sequencing reads or more). In some embodiments, the training maternal samples are sequenced at an average genome-wide sequencing depth of about 6 million sequencing reads or more (such as about 7 million sequencing reads or more, about 8 million sequencing reads or more, about 9 million sequencing reads or more, about 10 million sequencing reads or more, about 11 million sequencing reads or more, about 12 million sequencing reads or more, about 13 million sequencing reads or more, about 14 million sequencing reads or more, or about 15 million sequencing reads or more). Genome-wide sequencing depth refers to the number of sequencing reads that are generated when the full genome is sequenced. That is, if less than the full genome is sequenced (for example, an interrogated region of only predetermined regions), then the sequencing depth can be proportionately reduced.

The test maternal sample and the training maternal samples can be simultaneously assayed or independently assayed. For example, the machine-learning model can be trained from a database of training maternal samples. The database of training maternal samples can be static, or additional training maternal samples can be added to the database over time (for example, as further maternal samples are sequenced). The training maternal samples can also be simultaneously assayed along with the test maternal sample, for example by massive parallel sequencing of the plurality of maternal samples (including the training maternal samples and the test maternal samples). For example, a plurality of maternal samples can be sequenced in parallel. The fetal fraction of maternal samples taken from women with male pregnancies can be determined based on the dosage of the Y chromosome or X chromosome. Those maternal samples from women with male pregnancies can then be used to train a machine-learning model that is used to determine the fetal fraction of remaining maternal samples taken from women with female pregnancies. By regularly retraining the machine-learning model, the model is controlled for fluctuations in laboratory conditions.

The methods described herein are useful for determining a chromosomal abnormality of a test chromosome with high sensitivity and at lower measured fetal fraction percentages than known methods. In some embodiments, the measured fetal fraction is about 30% or less (such as about 25% or less, about 20% or less, about 15% or less, about 10% or less, about 5% or less, about 4% or less, about 3.5% or less, about 3% or less, about 2.5% or less, about 2% or less, about 1.5% or less, or about 1% or less). In some embodiments, the fetal fraction is about 1% or more, about 1.25% or more, about 1.5% or more, about 2% or more, about 2.5% or more, about 3% or more, about 3.5% or more, about 4% or more, or about 5% or more. In certain aspects, the sensitivity of the method is higher for determining a chromosomal abnormality of certain test chromosomes than other test chromosomes. For example, in some embodiments, there is a method for determining a chromosomal abnormality (such as trisomy) of chromosome 13, wherein the measured fetal fraction is about 1% or more (such as about 1.25% or more, about 1.5% or more, about 2% or more, about 2.5% or more, about 3% or more, about 3.5% or more, about 4% or more, or about 5% or more), wherein the sensitivity of the method is about 0.7 or higher, about 0.75 or higher, about 0.8 or higher, about 0.85 or higher, about 0.9 or higher, about 0.95 or higher, about 0.96 or higher, about 0.97 or higher, about 0.98 or higher, or about 0.99 or higher. In some embodiments, there is a method for determining a chromosomal abnormality (such as trisomy) of chromosome 18, wherein the measured fetal fraction is about 1% or more (such as about 1.25% or more, about 1.5% or more, about 2% or more, about 2.5% or more, about 3% or more, about 3.5% or more, about 4% or more, or about 5% or more), wherein the sensitivity of the method is about 0.4 or higher, about 0.45 or higher, about 0.5 or higher, about 0.55 or higher, about 0.6 or higher, about 0.7 or higher, about 0.75 or higher, about 0.8 or higher, about 0.85 or higher, about 0.9 or higher, about 0.95 or higher, about 0.96 or higher, about 0.97 or higher, about 0.98 or higher, or about 0.99 or higher. In some embodiments, there is a method for determining a chromosomal abnormality (such as trisomy) of chromosome 21, wherein the measured fetal fraction is about 1% or more (such as about 1.25% or more, about 1.5% or more, about 2% or more, about 2.5% or more, about 3% or more, about 3.5% or more, about 4% or more, or about 5% or more), wherein the sensitivity of the method is about 0.2 or higher, about 0.25 or higher, about 0.3 or higher, about 0.35 or higher, 0.4 or higher, about 0.45 or higher, about 0.5 or higher, about 0.55 or higher, about 0.6 or higher, about 0.7 or higher, about 0.75 or higher, about 0.8 or higher, about 0.85 or higher, about 0.9 or higher, about 0.95 or higher, about 0.96 or higher, about 0.97 or higher, about 0.98 or higher, or about 0.99 or higher.

Measuring Chromosome Dosage

The dosage of the test chromosome or a test portion of a chromosome in the test maternal sample can be measured and compared to an expected dosage for the test chromosome (or test portion of the chromosome), where the expected dosage is the dosage if the test chromosome or portion thereof were normal (e.g., euploid or no microdeletion). Chromosome dosage can be measured, for example, using an assay that generates a plurality of quantifiable products (such as sequencing reads or PCR (such as digital PCR) products originating from the test chromosome), wherein the number of quantifiable products indicates the measured test chromosome dosage.

In some embodiments, the test chromosome or a test portion of the chromosome is selected from the maternal sample prior to generating the quantifiable products (i.e., selectively isolated from the maternal sample prior to generating the quantifiable products). Such methods for selection include, for example, selective capture (such as hybridization). In some embodiments, the quantifiable products used to measure the chromosome dosage can be selected after being generated, for example by filtering sequencing reads. In some embodiments, the quantifiable products are generated simultaneously to selecting the test chromosome or test portion of the chromosome, for example by selective PCR amplification.

The original source (i.e., fetal or maternal test chromosome) of the quantifiable products need not be distinguished, as the measured test chromosome dosage is used in conjunction with the measured fetal fraction, as explained below. Solely by way of example, if the test chromosome were chromosome 21, sequencing reads can be generated from both fetal chromosome 21 and maternal chromosome 21 in the test maternal sample. The generated sequencing reads can be treated identically and without regard to whether the origin of any particular sequencing read is fetal chromosome 21 or maternal chromosome 21.

Exemplary methods for determining chromosome dosage are described in Fan & Quake, PLoS ONE, vol. 5(5), e10439 (2010) and U.S. Pat. No. 8,008,018. Briefly, an assay can be performed to generate a plurality of quantifiable products from the test chromosome. As the fetal fraction in a maternal sample is usually relatively low, the majority of the quantifiable products that are generated will originate from the maternal cfDNA. However, a portion of the quantifiable products will originate from the fetal cfDNA. If, for example, the test chromosome from the fetal cfDNA is trisomic for the test chromosome, the number of resulting sequencing quantifiable products will be greater than would be expected if the fetal cfDNA were disomic for the test chromosome.

In some embodiments, a test portion of a chromosome is selected as a putative microdeletion. A microdeletion is a segment of chromosomal DNA missing in at least one fetal chromosome. Exemplary microdeletions include 22q11.2 deletion syndrome, 1p36 deletion syndrome, 15q11.2 deletion syndrome, 5p deletion syndrome, and 4p deletion syndrome The dosage of the portion of the chromosome with a microdeletion will be less than the expected dosage (that is, without the microdeletion). However, assuming a euploid chromosome, the remaining portions of chromosome with the putative microdeletion will have a measured dosage that is not statistically different from the expected dosage. The expected dosage can be determined, for example, from portions of the chromosome other than the putative region, or from other chromosomes or portions of other chromosomes in the genome. The microdeletion can be detected, for example, using circular binary segmentation techniques or by using a hidden Markov model search algorithm. See, for example, Zhao et al., Detection of Fetal Subchromosomal Abnormalities by Sequencing Circulating Cell-Free DNA from Maternal Plasma, Clinical Chemistry, vol. 61, pp. 608-616 (2015). For example, a sliding window along a chromosome can select a putative microdeletion and the chromosome dosage can be measured within the selected window (for example, a reads-per-bin distribution within any given window). The measured chromosome dosage of the putative microdeletion is compared to an expected dosage, and a value of likelihood of a microdeletion or a value of statistical significance can be determined, as further explained below. In some embodiments, the microdeletion is about 500,000 bases to about 15 million bases in length (for example, about 1 million to about 2 million bases in length, about 2 million to about 4 million bases in length, about 4 million to about 6 million bases in length, about 6 million to about 8 million bases in length, about 8 million to about 10 million bases in length, about 10 million to about 12 million bases in length, or about 12 million bases to about 15 million bases in length). In some embodiments, the microdeletion is more than about 15 million bases in length.

In some embodiments, the measured dosage is compared to an expected dosage (assumed normal) using statistical analysis. The statistical analysis can be used to evaluate the measured test chromosome dosage to determine a value of statistical significance (such as a Z-score, a p-value, or a probability) and/or value of likelihood that the test chromosome or portion thereof is abnormal.

In some embodiments, the dosage of the test chromosome (or portion thereof) is measured by aligning a plurality of sequencing reads from the test chromosome (or portion) in the maternal sample, binning the aligned sequencing reads in a plurality of bins, counting the number of sequencing reads in each bin, and determining a distribution for the number of reads per bin. The sequencing reads can be generated, for example, using massive parallel sequencing techniques. In some embodiments, the sequencing reads are generated using the same assay used to measure the fetal fraction of the maternal sample (that is, the sequencing reads used to measure the chromosome dosage are generated simultaneously as the sequencing reads used to measure the fetal fraction).

The sequencing reads generated from the test chromosome (or portion thereof) are aligned, for example using a reference sequence (such as a chromosome or portion from a human reference genome). The sequencing reads are then binned in a plurality of bins. In some embodiments, the bins are about 1 base to about one chromosome in length (such as about 1 kilobase to about 200 kilobases in length such as about 1 kilobases to about 5 kilobases, about 5 kilobases to about 10 kilobases, about 10 kilobases to about 20 kilobases, about 20 kilobases to about 50 kilobases, about 50 kilobases to about 100 kilobases, or about 100 kilobases to about 200 kilobases). In some embodiments, the interrogated region comprises about 1000 bins to about 100,000 bins (such as between about 1000 bins and about 2000 bins, between about 2000 bins and about 5000 bins, between about 5000 bins and about 10,000 bins, between about 10,000 bins and about 20,000 bins, between about 20,000 bins and about 40,000 bins, between about 40,000 bins and about 60,000 bins, between about 60,000 bins and about 80,000 bins, or between about 80,000 bins and about 100,000 bins). Preferably, the bins are of equal size.

The number of sequencing reads in each bin along the test chromosome is counted. Optionally, the counted sequencing reads for each bin are normalized, for example by accounting for variations in GC content or mappability of the reads between the bins. Normalization can also optionally include scaling the number of sequencing reads in each bin, for example by dividing the number of sequencing reads in each bin by the mean or median number of sequencing reads for the bins within the interrogated region.

A distribution of the number of reads per bin can be determined for the measured dosage. The distribution for the measured dosage can include, for example, an average (mean or median, or a value approximating a mean or a median), $\mu_{test}$, and a variation, $\sigma_{test}$ of the number of reads per bin. The variation can be, for example, a standard deviation or an interquartile range.

As chromosomal abnormality (such as aneuploidy or a microdeletion) is a relatively rare event compared to chromosomal normality (such as euploidy or no microdeletion), it can be assumed that the average dosage of each chromosome or portion thereof in a sufficiently large plurality of maternal samples reflects the expected dosage (i.e., normal for each chromosome or portion thereof). In some embodiments, the plurality of maternal samples comprises a plurality of external maternal samples. In some embodiments, the plurality of maternal samples comprises a plurality of external maternal samples and the test maternal sample. In some embodiments, the expected chromosomal dosage may be determined using a single maternal sample, which may be an external sample or the test maternal sample itself.

The expected dosage (that is, assuming the test chromosome is normal) for the test maternal sample can be determined based on the measured dosage of one or more external maternal samples (that is, maternal samples other than the test maternal sample), the test maternal sample, or a combination thereof. For example, in some embodiments, the measured dosage of one or more chromosomes (or portions thereof) other than the test chromosome (or portion thereof) from the test maternal sample is used to determine the expected dosage of the test maternal sample (or portion thereof). In some embodiments, the measured dosage of the test chromosome (or a portion thereof) from one or more external samples is used to determine the expected dosage of the test chromosome (or portion thereof) in the test maternal sample. In some embodiments, the measured dosage of the test chromosome (or a portion thereof) from one or more external samples and the measured dosage of the test chromosome (or portion thereof) from the test maternal sample is used to determine the expected dosage of the test chromosome (or portion thereof) in the test maternal sample. In some embodiments, the measured chromosome dosage of one or more chromosomes or portion thereof (which may or may not comprise the test chromosome or portion thereof) from one or more external maternal samples is used to determine the expected dosage of the test chromosome (or portion thereof) from the test maternal sample. In some embodiments, the measured chromosome dosage of one or more chromosomes or portion thereof (which may or may not comprise the test chromosome or portion thereof) from one or more external maternal samples and the measured chromosome dosage of one or more chromosomes or portion thereof (which may or may not comprise the test chromosome thereof) from the test maternal sample is used to determine the expected dosage of the test chromosome (or portion thereof) from the test maternal sample. In some embodiments, the one or more external maternal samples are the same as one or more of the training maternal samples used to train the machine-learning model used to determine the fetal fraction of the test maternal sample.

In some embodiments, the expected dosage of a test chromosome or a portion thereof in a test maternal sample is determined by measuring the dosage of a chromosome (or a portion thereof) other than the test chromosome (or the portion thereof) in the test maternal sample. That is, the expected dosage is determined using a measured dosage internal to the test maternal sample. In some embodiments, the measured dosage includes an average number of reads per bin and a variation of the number of reads per bin. In some embodiments, the expected dosage of the test chromosome or the portion thereof is the measured dosage of the chromosome or the portion thereof other than the test chromosome or the portion thereof. Preferably, if the dosage of a portion of a chromosome is measured, the portion of the chromosome is on a different chromosome than the test chromosome portion.

In some embodiments, the expected dosage of a test chromosome or a portion thereof in a test maternal sample is determined by measuring the dosages of two or more chromosomes or portions thereof other than the test chromosome or the portion thereof in the test maternal sample. That is, the expected dosage is determined using a plurality of measured dosages (other than the test chromosome or portion thereof) internal to the test maternal sample. Each measured dosage can include an average number of reads per bin and a variation of the number of reads per bin. In some embodiments, an average distribution (or average mean or average median and an average variation) of the two or more measured dosages is determined. In some embodiments, the average distribution (or average mean or average median and average variation) is the expected dosage of the test chromosome or portion thereof. In some embodiments, the average distribution (or average mean or average median and average variation) of two or more, three or more, four or more, five or more, six or more, seven or more, eight or more, nine or more, or ten or more chromosomes or portions thereof other than the test chromosome or portion thereof is the expected chromosome dosage of the test chromosome or portion thereof. In some embodiments, the two or more chromosomes include all chromosomes other than the test chromosome or portion thereof or all autosomal chromosomes other than the test chromosome or portion thereof. In some embodiments, the test chromosome or portion thereof is further included in the average distribution to determine the expected dosage of the test chromosome or portion thereof.

In some embodiments, the expected dosage of the test chromosome or portion thereof in the test maternal sample is determined by measuring the dosage of the test chromosome or portion thereof in one or more external samples. When a single external sample is used, the measured dosage can include an average number of reads per bin and a variation of the number of reads per bin. In some embodiments, the measured dosage of the test chromosome (or portion thereof) from the external sample is used as the expected dosage of the test chromosome from the test maternal sample. If a plurality of external samples is used, the measure dosage of the test chromosome (or portion thereof) from each of the external maternal samples can be averaged to obtain an average distribution (or average mean or average median and average variation). The average distribution determined from the measured dosages of the test chromosome from the plurality of external maternal samples can be used as the expected dosage of the test chromosome from the test maternal sample.

In some embodiments, the expected dosage of one or more chromosomes (such as a test chromosome) or a portion thereof for the test maternal sample is determined by measuring the dosage of one or more chromosomes from one or more external samples. For example, in some embodiments, the expected dosage of a test chromosome or a portion thereof for the test maternal sample is determined by training a machine-learning model using a plurality of external samples, and applying the machine-learning model to the measured dosage of one or more chromosomes or a portion thereof from the test sample. The one or more chromosomes or a portion thereof used to determine the expected dosage of the test chromosome or a portion thereof in the test sample can be all chromosomes in the genome, all autosomal chromosomes, all chromosomes in the genome excluding the test chromosome, all autosomal chromosomes excluding the test chromosome, or any portion thereof.

In some embodiments, a machine-learning model (such as a regression model, such as a linear-regression model) is trained using a measured dosage of a test chromosome or portion thereof and a measured dosage of at least one chromosome or portion thereof other than the test chromosome or portion thereof in a plurality of maternal samples, and the machine learning model is applied to the measured dosage of the at least one chromosome or portion thereof other than the test chromosome or portion thereof in a test maternal sample to determine the expected chromosome dosage of the test chromosome or portion thereof in the test maternal sample. In some embodiments, a dosage distribution vector comprising the dosages from each of the at least one chromosome or portions thereof other than the test chromosome or portion thereof is regressed onto the dosage of the test chromosome or portion thereof for each maternal sample in the plurality of maternal samples, thereby training the regression model. The trained model is then applied to a dosage distribution vector comprising the dosages from each of the at least one chromosome or portion thereof other than the test chromosome or portion thereof from the test maternal sample to obtain the expected dosage of the test chromosome or portion thereof. In some embodiments, the dosage distribution vector comprises an average (mean or median) dosage vector and a variation dosage vector (for example, the average (mean or median) reads per bin can be determined independently from the variation of the number of reads per bin). In some embodiments, the plurality of maternal samples includes the test maternal sample. In some embodiments, the plurality of maternal samples excludes the test maternal samples. In some embodiments, the at least one chromosome or portion thereof other than the test chromosome or portion thereof includes all chromosomes other than the test chromosome or portion thereof or all autosomal chromosomes other than the test chromosome or portion thereof. In some embodiments, the at least one chromosome or portion thereof other than the test chromosome further includes the test chromosome.

In some embodiments, the one or more chromosomes or portions thereof used to determine the expected dosage would exclude chromosomes with an increased likelihood of aneuploidy, such as chromosomes 13, 18, 21, X, or Y. In some embodiments, the chromosome dosage for each of the one or more chromosomes or portions thereof is determined separately. The chromosome dosage can be a distribution of reads per bin, and can include a mean (or median) and a variation (such as a standard deviation or an interquartile range).

When using a plurality of maternal samples to determine the expected dosage, it is generally preferred that the measured dosages used to determine the expected dosage of the test chromosome or portion thereof is measured under the same conditions as the measurement for the test chromosome dosage in the test maternal sample. For example, in some embodiments, the dosage of the one or more chromosomes in the external maternal samples and the test chromosome (or test portion) dosage in the test maternal sample are measured simultaneously or approximately simultaneously. In some embodiments, the test chromosome dosage in the test maternal sample and the one or more additional chromosomes from the test maternal sample are measured simultaneously or approximately simultaneously.

Statistical Analysis

A value of likelihood that the fetal cell-free DNA in the test maternal sample is abnormal (for example, aneuploid or has a microdeletion) for the test chromosome or test portion thereof can be determined based on the measured dosage of the test chromosome or portion thereof, the expected dosage of the test chromosome, and the measured fetal fraction. In some embodiments, the value of likelihood is determined by determining a value of statistical significance (such as a Z-score) for the test chromosome (or portion thereof) based on the measured dosage and the expected dosage; and then determining the value of likelihood of abnormality based on the value of statistical significance and the measured fetal fraction.

A statistical test (such as a Z-test) can be used to determine whether the measured dosage is statistically different from the expected dosage (i.e., the normal chromosome null hypothesis). To conduct the statistical test, a value of statistical significance is determined and compared to a predetermined threshold. If the value of statistical significance is above the predetermined threshold, the null hypothesis (that is, that the test chromosome is normal) can be rejected. In some embodiments, the value of statistical significance is a Z-score. In some embodiments, the Z-score is determined using the following formula:

$$Z = \frac{\mu_{test} - \mu_{exp}}{\sqrt{\frac{\sigma_{test}^2}{n_{test}} + \frac{\sigma_{exp}^2}{n_{exp}}}}$$

where $\mu_{test}$ is the mean or median for the measured dosage distribution of the test chromosome (or portion thereof), $\mu_{exp}$ is the mean or median for the expected dosage distribution, $\sigma_{test}$ is the variation (such as standard deviation or interquartile range) for the measured dosage distribution of the test chromosome (or portion thereof), $\sigma_{exp}$ is the variation (such as standard deviation or interquartile range) for the expected dosage distribution, $n_{test}$ is the number of inputs to determine the measured dosage distribution (e.g., the number of bins) of the test chromosome (or portion thereof), and $n_{exp}$ is the number of inputs to determine the expected dosage distribution (e.g., the number of bins).

In some embodiments, the Z-score calculation is simplified by assuming that the number of inputs used to determine the measured dosage and the expected dosage are the same, and that the variations for the measured dosage ($\sigma_{test}$) distribution and the expected dosage distribution ($\sigma_{exp}$) are approximately the same, and can be determined using the following formula:

$$Z = \frac{\mu_{test} - \mu_{exp}}{\sigma_{test}}$$

or:

$$Z = \frac{\mu_{test} - \mu_{exp}}{\sigma_{exp}}$$

The value of statistical significance is highly correlated with fetal fraction for an aneuploid test chromosome in the test maternal sample. That is, among maternal samples that are abnormal for the test chromosome (or portion thereof), those maternal samples with a higher fetal fraction of cfDNA will have a higher absolute value of statistical significance. However, for those maternal samples with normal test chromosome, the value of statistical significance does not substantially change for differences in fetal fraction. Thus, maternal samples having low fetal fraction and abnormal test chromosome (or portion thereof) may have a value of statistical significance near those maternal samples having a normal test chromosome (or portion thereof), particularly when the sequencing depth is low. Thus, a value of likelihood that the fetal cell-free DNA is abnormal for the test chromosome can be determined based on the measured test chromosome dosage and the expected test chromosome dosage (for example, by using the Z-score), as well as the fetal fraction. This value of likelihood can be expressed as, for example an odds ratio that the test chromosome (or portion thereof) is abnormal versus normal. See, for example, U.S. Pat. No. 8,700,338.

The value of likelihood of an abnormal chromosome (or portion thereof) can be determined using a model assuming a normal fetal test chromosome (or portion thereof) and/or a model assuming an abnormal fetal test chromosome (or portion thereof). The models can be developed, for example, using a Monte Carlo simulation to estimate the difference between the measured test chromosome dosage and the expected chromosome dosage (which may be, for example, expressed as ($\mu_{test}-\mu_{exp}$) or a value of statistical significance) for randomly generated maternal samples drawn from empirical samples. The empirical samples can include, for example, samples taken from verified abnormal maternal samples with known fetal fraction and samples taken from non-pregnant women (where the fetal fraction is defined as 0 and the measured test chromosome dosage equals the expected dosage). The models provide a distribution of estimated difference between the measured test chromosome dosage and the expected chromosome dosage for a specified fetal fraction.

In some embodiments, the value of likelihood for an abnormal test chromosome from the test maternal sample is expressed as an odds ratio:

$$\frac{P(x_i \mid A)}{P(x_i \mid E)}$$

wherein $P(x_i|A)$ is the probability that the difference between the measured test chromosome or portion thereof (i) dosage (which, for example, may be expressed as ($\mu_{test}-\mu_{exp}$) or a Z-score), $x_i$, can be attributed to aneuploidy, A, and $P(x_i|E)$ is the probability that the difference between the measured test chromosome dosage (which, for example, may be expressed as ($\mu_{test}-\mu_{exp}$) or a Z-score), $x_i$, can be attributed to euploidy, E.

In some embodiments, the value of likelihood that the fetal cell-free DNA is abnormal for the test chromosome accounts for the probability that the measured fetal proportion is reflective of a true fetal fraction. When the fetal fraction is measured using any known method or the method described herein, there is some probability that the measured fetal fraction is reflective of the true fetal fraction. The value of likelihood that the fetal test chromosome from the test maternal is abnormal can be determined using the abnormal model and/or the normal model at any given fetal fraction, but this value of likelihood can also be adjusted using a weighted average across a spectrum of possible fetal fractions, wherein the probability of aneuploidy for a given fetal fraction is weighted by the probability that the measured fetal fraction reflects the true fetal fraction. This accounting can be reflected as follows:

$$P(A_i|FF_m,x_i) = \int_{FF_t} P(A_i|FF_t,x_i) \times P(FF_t|FF_m)$$

wherein $FF_m$ is the measured fetal fraction and $FF_t$ is the true fetal fraction. The term $P(A_i|FF_t, x_i)$ represents the probability of aneuploidy relative to the summed probability of euploidy and aneuploidy. Specifically:

$$P(A_i \mid FF_t, x_i) = \frac{P(z_i \mid \mu_{i,aneuploid}, \sigma_{i,aneuploid})}{P(z_i \mid \mu_{i,aneuploid}, \sigma_{i,aneuploid}) + P(z_i \mid \mu_{i,euploid}, \sigma_{i,euploid})}$$

where $\mu_{i,euploid}=0$, $\sigma_{i,euploid}=1$ ($\sigma$ achieves a normalized value of 1 after dividing all un-normalized values of statistical significance (e.g., Z-scores) by the standard deviation of un-normalized statistical significance (e.g., Z-scores)), and $\mu_{aneuploid}$, and $\sigma_{aneuploid}$ are functions of fetal fraction (e.g., a linear model can be fit to a set of aneuploidy samples where both the fetal fraction and Z-score are known; thus, the mean and standard deviation of Z-scores for a particular fetal fraction can be inferred from the linear model). The probabilities themselves are calculated by noting that the values of statistical significance (e.g., Z-score) distributions are Gaussian—thus completely characterized by the mean, $\mu$, and standard deviation, $\sigma$—and using the Gaussian probability-density function to calculate the probability of a given z-score. The probability that the measured fetal proportion is reflective of a true fetal fraction can be determined, for example, by modeling a Gaussian distribution centered on the measured fetal fraction, with the distribution determined from maternal samples with known fetal fractions. The Gaussian is fit to the distribution of observed differences between the true fetal fraction and the measured fetal fraction for a plurality of samples. The difference between the true fetal fraction and the measured fetal fraction can be measured by applying the trained machine-learning model on a set of maternal samples with known fetal fraction (such as from maternal samples with male pregnancies). The distribution of differences between the true fetal fraction and the measured fetal fraction for the set of maternal samples with male pregnancies can be fit by a Gaussian model to yield mean, $\mu$, and standard deviation, $\sigma_{FF}$, which is then applied to the test maternal sample. Thus, to calculate $P(FF_t|FF_m)$, the Gaussian probability density function can be used where the mean, $\mu$, is set to $FF_m$ and the standard deviation is $\sigma_{FF}$. In some embodiments, the maternal samples used to generate the model distribution comprise the training maternal samples.

Abnormal Chromosome Calling and Dynamic Iterative Depth Optimization

In some embodiments, the test chromosome is called as abnormal (e.g., aneuploid or microdeletion) or normal (e.g., euploid or no microdeletion) using an initially determined value of statistical significance (such as a Z-score) and/or value of likelihood of abnormality. In some embodiments, the test chromosome (or portion thereof) is not called as abnormal or normal using the initially determined value of statistical significance or value of likelihood, and the test chromosome dosage is re-measured and a subsequent value of statistical significance and/or subsequent value of likelihood is determined. The re-measured dosage of the test chromosome (or portion thereof) is re-measured using a higher accuracy assay. For example, the dosage of the test chromosome (or portion thereof) can be measured by analyzing a greater number of quantifiable products (such as sequencing reads).

In some embodiments, if the initial value of statistical significance is above a predetermined threshold, the test chromosome (or portion thereof) from the test maternal sample is called as abnormal (e.g., aneuploid or microdeletion) for the fetal cfDNA. It should be noted that when evaluating the value of statistical significance (such as a Z-score) against a predetermined threshold, the absolute value of the value is preferably considered. This is because, in some instances, the aneuploid test chromosome has only a single copy (i.e., monoploid) originating from the fetal cfDNA, whereas the test chromosome would be expected to have two copies (i.e., diploid). An example of this is Turner syndrome, wherein the fetus has monosomy X. The measured test chromosome dosage would thus be less than the expected chromosome dosage, and the Z-score could be computed as a negative value. Similarly, in the circumstance of a microdeletion, an abnormal chromosome with a microdeletion would result in a lower measured dosage than a normal chromosome without the microdeletion. Thus, it is equivalent to call the test chromosome (or portion thereof) as abnormal for the fetal cfDNA when a positive value of statistical significance (e.g., Z-score) is above a positive predetermined threshold as it is to call the test chromosome as abnormal for the fetal cfDNA when a negative value of statistical significance is below a negative predetermined threshold. However, when making a specific call of fewer copies of the test chromosome (or portion thereof) in the fetal cfDNA than the expected number of copies, such as in the case of monosomy X or a microdeletion, then the call can be made when the value of statistical significance is below a negative predetermined threshold.

When the absolute value of the statistical significance is above the predetermined threshold, the measured dosage of the test chromosome (or portion thereof) is sufficiently above (or below, the case of a negative predetermined threshold) the expected dosage that the call of abnormality (such as aneuploidy or microdeletion) can be made with the desired confidence level. The desired confidence level can be used to set the predetermined threshold. In some embodiments, the desired one-tailed confidence level ($\alpha$) is about 0.05 or lower (such as about 0.025 or lower, about 0.01 or lower, about 0.005 or lower, or about 0.001 or lower). In some embodiments, the predetermined threshold for the Z-score is about 2 or higher (such as about 2.5 or higher, about 3 or higher, about 3.5 or higher, about 4 or higher, about 4.5 or higher, or about 5 or higher).

When the absolute value of the value of statistical significance is below the predetermined threshold, the measured dosage of the test chromosome or portion thereof is not sufficiently above (or below in the case of a negative predetermined threshold) the expected test chromosome dosage that the call of abnormality (e.g., aneuploidy or microdeletion) cannot be made with the desired confidence level. This might occur, for example, when the test chromosome is euploid for the fetal cfDNA, but may also occur when the test chromosome is aneuploid for the cfDNA and the accuracy or precision of the measured test chromosome dosage is not sufficient to distinguish the measured test chromosome dosage from the expected test chromosome dosage. The accuracy or precision may not be sufficient, for example, if the fetal fraction of cfDNA in the test maternal sample is low and the sequencing depth is low.

In some embodiments, a value of likelihood that the fetal cell-free DNA is abnormal (e.g., aneuploid or microdeletion) for the test chromosome (or portion thereof) is determined based on the measured dosage of the test chromosome (or portion thereof), the expected dosage, and the measured fetal fraction. The value of likelihood can be, for example, odds ratio that the test chromosome for the fetal cfDNA is abnormal versus normal. In some embodiments, if the value of likelihood that the test chromosome is abnormal is below a predetermined threshold, then the test chromosome (or portion thereof) is called as normal. If, however, the value of likelihood is above the predetermined threshold, the test chromosome (or portion thereof) is not called as normal (and may be called as abnormal if the absolute value of the value of statistical significance is above the predetermined threshold). If the test chromosome (or portion thereof) is not called as normal and is not called as abnormal (for example, if the value of statistical significance is below a predetermined threshold and the value of likelihood of abnormality is above a predetermined threshold), it is generally because the measured test chromosome dosage is not sufficiently resolved from the expected test chromosome dosage. In some embodiments, if the test chromosome is not called as abnormal or normal from the initially determined value of likelihood and/or value of statistical significance, the test chromosome dosage is re-measured by analyzing a greater number of quantifiable assay products, such as sequencing reads. In some embodiments, the predetermined threshold that that the odds ratio that the test chromosome for the fetal cfDNA is abnormal versus normal is about 0.05 or higher, about 0.1 or higher, about 0.15 or higher, about 0.20 or higher, about 0.25 or higher, or about 0.3 or higher.

As an example, the determination of a call for the test chromosome or portion thereof as normal (e.g., euploid or no microdeletion) or abnormal (e.g., aneuploid or with a microdeletion) can summarized in Table 1, wherein the arrow indicates whether the indicated value is above or below the predetermined threshold.

TABLE 1

Abnormal Test Chromosome (or Portion) Calling Logic

| Value of Statistical Significance | Value of Likelihood of Abnormality | Call |
|---|---|---|
| ↑ | n.d. | Abnormal |
| ↓ | ↑ | No call |
| ↓ | ↓ | Normal |

"n.d." indicates that the value of likelihood of aneuploidy need not be determined if the value of statistical significance is above the predetermined threshold.

If no call is made (for example, because the value of statistical significance is too low and the value of likelihood of an abnormality is too high), the test maternal sample can be reflexed (that is, the test chromosome is re-measured) with a greater assay depth. Optionally, if the test maternal sample is reflexed, the fetal fraction can also be re-measured with a greater assay depth. In some embodiments, the reflex equation is expressed as:

$$\max_{i \in (chr13, chr18, chr21, chrX)} p(A_i | FF_m, z_i) > \alpha$$

Evaluate the probability, $p(A_i|FF_m, z_i)$, of aneuploidy of a test chromosome or portion thereof, i, for a given measured fetal fraction, $FF_m$, and value of statistical significance, $z_i$, across all test chromosomes or portion thereof of interest (e.g., the set of chromosome 13, chromosome 18, chromosome 21, and chromosome X; though, this set could be expanded to include other chromosomes or portions thereof that are of interest), and take the maximum of the results. If that maximum exceeds a predetermined threshold, $\alpha$, the test maternal sample should be reflexed to a higher depth of sequencing.

In some embodiments, an abnormal call or a normal call is made only if the measured fetal fraction is above a predetermined threshold. In some embodiments, the predetermined threshold is about 2% or higher (such as about 2.5% or higher, about 3% or higher, about 3.5% or higher, about 4% or higher, about 4.5% or higher, or about 5% or higher), using any of the methods to determine fetal fraction as described herein. As the measured fetal fraction can vary depending on the method used, the fetal fraction may be referenced as a percentile (for example, about 0.01% of maternal samples may have a measured fetal fraction of about 1% or less). In some embodiments, the predetermined fraction is a percentile, such as about 0.25 percentile or higher, about 0.35 percentile or higher, about 0.5 percentile or higher, about 1 percentile or higher, about 1.5 percentile or higher, about 2 percentile or higher, about 2.5 percentile or higher, about 3 percentile or higher, about 3.5 percentile or higher, about 4 percentile or higher, about 5 percentile or higher, about 6 percentile or higher, about 7 percentile or higher, or about 8 percentile or higher.

In some embodiments, the test chromosome (or portion thereof) of the fetal cfDNA is called as abnormal (e.g., aneuploid or having a microdeletion) if the value of statistical significance (e.g., Z-score) is above a predetermined threshold. In some embodiments, the test chromosome (or portion thereof) of the fetal cfDNA is called as abnormal (e.g., aneuploid or having a microdeletion) only if the value of statistical significance (e.g., Z-score) is above a predetermined threshold. In some embodiments, the test chromosome of the fetal cfDNA is called as abnormal (e.g., aneuploid or having a microdeletion) only if the fetal fraction is above a predetermined threshold.

In some embodiments, the test chromosome (or portion thereof) of the fetal cfDNA is called as normal (e.g., euploid or no microdeletion) if the value of likelihood of an abnormality is below a predetermined threshold. In some embodiments, the test chromosome (or portion thereof) of the fetal cfDNA is called as normal (e.g., euploid or no microdeletion) only if the value of likelihood of an abnormality is below a predetermined threshold. In some embodiments, the test chromosome (or portion thereof) of the fetal cfDNA is called as normal (e.g., euploid or no microdeletion) if the value of likelihood of an abnormality is below a predetermined threshold and the value of statistical significance is below a predetermined threshold. In some embodiments, the test chromosome (or portion thereof) of the fetal cfDNA is called as normal (e.g., euploid or no microdeletion) only if the value of likelihood of an abnormality is below a predetermined threshold and the value of statistical significance is below a predetermined threshold. In some embodiments, the test chromosome (or portion thereof) of the fetal cfDNA is called as normal (e.g., euploid or no microdeletion) only if the fetal fraction is above a predetermined threshold.

In some embodiments, the dosage of the test chromosome (or portion thereof) is re-measured if the value of likelihood of an abnormality is above a predetermined threshold and the value of statistical significance (such as a Z-score) is below a predetermined threshold. In some embodiments, the dosage of the test chromosome (or portion thereof) is re-measured only if the value of likelihood of an abnormality is above a predetermined threshold and the value of statistical significance (such as a Z-score) is below a predetermined threshold.

In some embodiments, the dosage of the test chromosome (or portion thereof) is re-measured using a subsequent assay that generates a subsequent plurality of quantifiable products (such as sequencing reads or PCR products) from the test chromosome. In some embodiments, the fetal fraction is also re-measured using the subsequent plurality of quantifiable products. The subsequent plurality of quantifiable products can be separately analyzed, or the quantifiable products can be analyzed in combination with the plurality of quantifiable products formed from the initial assay. The number of quantifiable products in the subsequent plurality (or the number of quantifiable products in the combination of the subsequent plurality and the initial plurality) is preferably greater than the number of quantifiable products in the initial assay. By generating a large number of quantifiable products, the accuracy and/or precision of the measured chromosome dosage can be enhanced. A subsequent value of likelihood that the fetal cell-free DNA is aneuploid for the chromosome and/or a subsequent value of statistical significance can then be determined based on the re-measured chromosome dosage.

When the dosage of the test chromosome or portion thereof is re-measured, for example by using an assay that generates a subsequent plurality of quantifiable products, wherein the number of quantifiable products used to determine the re-measured dosage is greater than the number of quantifiable products used to determine in initially measured dosage, the expected chromosome dosage is adjusted to account for the increase in the number of quantifiable products. In some embodiments, the expected chromosome dosage is re-determined using the methods described herein, but with the greater number of quantifiable products.

By way of example, the number of quantifiable products (such as sequencing reads) in the initial assay used to determine the initial test chromosome dosage (and/or fetal fraction) can be about 6 million reads or more (such as about 7 million reads or more, about 8 million reads or more, about 9 million reads or more, about 10 million reads or more, about 11 million reads or more, about 12 million reads or more, about 13 million reads or more, about 14 million reads or more, about 15 million reads or more, about 16 million reads or more, or about 17 million reads or more). The number of reads is based on genome-wide sequencing, and the number of reads can be reduced by the proportion of the genome that is actually sequenced. The number of quantifiable products used to determine the subsequent dosage of the test chromosome or portion thereof (which can be, for example, the combination of the quantifiable products from the initial assay and the subsequent assay, or from the subsequent assay alone) can be, for example, about 18 million reads or more (such as about 20 million reads or more, about 25 million reads or more, about 30 million reads or more, about 35 million reads or more, about 40 million reads or more, about 45 million reads or more, about 50 million reads or more, about 60 million reads or more, about 70 million reads or more, about 80 million reads or more, about 90 million reads or more, or about 100 million reads or more). As the cost of an assay generally increases with the number of reads, it is generally preferable to minimize the number of reads necessary in an initial or subsequent assay. By performing the initial assay for all test maternal samples and only performing the subsequent assay for those test maternal samples for which no call (either aneuploid or euploid) can be made, excess and unnecessary assays are minimized.

Calls of normal or abnormal test chromosome can be made using the subsequently determined value of statistical significance (e.g., Z-score) and/or value of likelihood of abnormality in a similar manner as for the initially determined value of statistical significance and/or value of likelihood of abnormality, except the determination is based on the re-measured dosage. Because the re-measured dosage of the test chromosome or portion thereof is determined using a larger number of quantifiable products, the accuracy of the re-measured dosage and the expected dosage is greater, and the magnitude of the expected variance is less.

In some instances, the absolute value of the subsequently determined value of statistical significance (e.g., Z-score) is below the predetermined threshold and the subsequent value of likelihood of an abnormality is above the predetermined threshold. Optionally, a no-call can be made for those samples. Alternatively, the test maternal sample can be again reflexed (that is, the dosage of the test chromosome (or a portion thereof) can be again re-measured and value of statistical significance and/or value of likelihood of an abnormality re-determined). In some embodiments, test maternal samples are reflexed one or more times, two or more times, three or more times, or four or more times.

Figure 2:
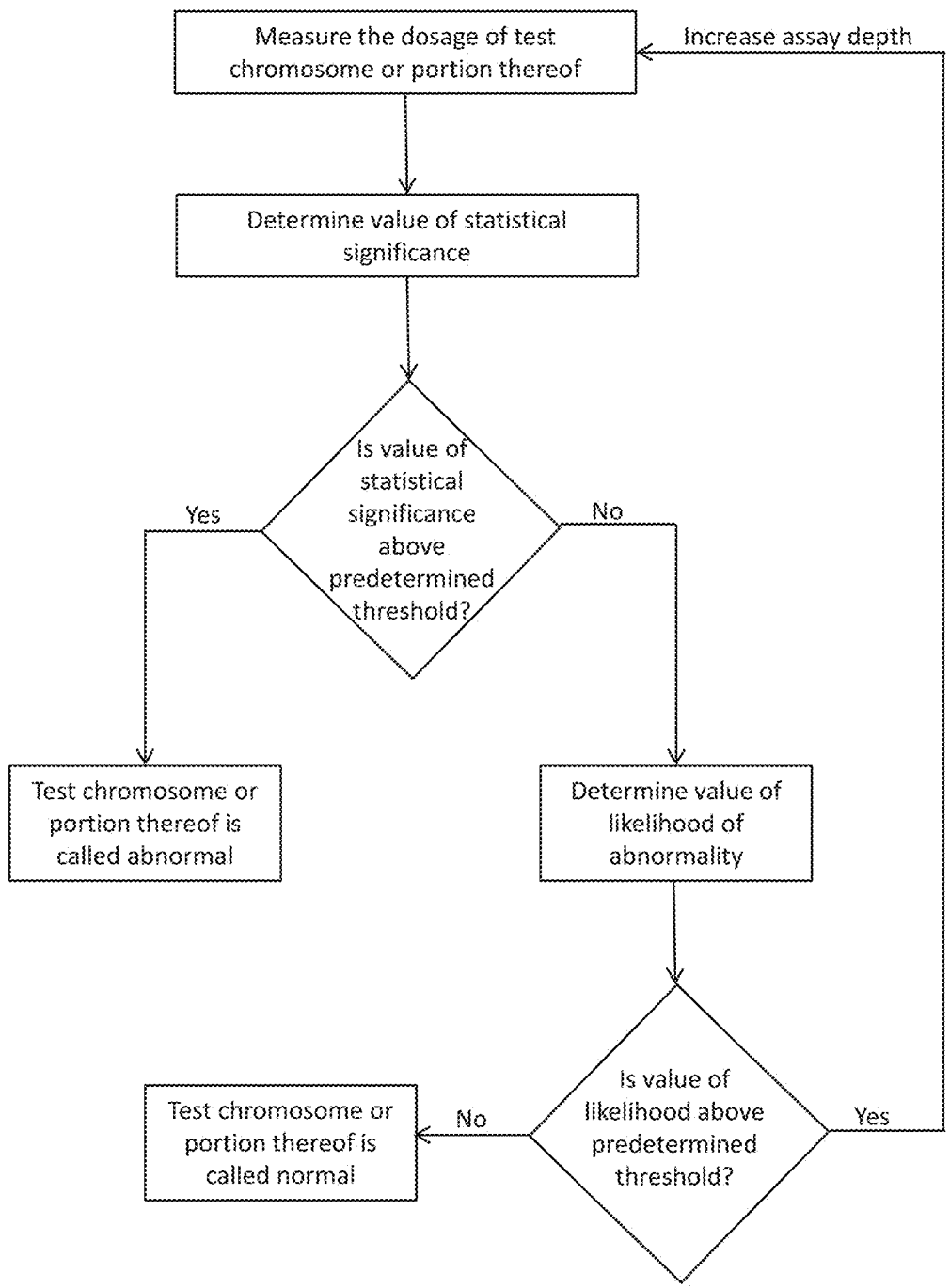
FIG. 2 illustrates an exemplary workflow for the dynamic iterative depth optimization process.

FIG. 2 illustrates one exemplary workflow for the dynamic iterative depth optimization process. An initial dosage of a test chromosome or a portion thereof is determined, for example by using an assay to generate sequencing reads, which are aligned, binned in a plurality of bins, and forming a distribution of the normalized number of reads per bin. A value of statistical significance (such as a Z-score) for the test chromosome or the portion thereof based on the measured dosage and an expected dosage. If the value of statistical significance is above a predetermined threshold, then the test chromosome or portion thereof is called as abnormal. If the value of statistical significance is below the predetermined threshold for the value of statistical significance, a value of likelihood of abnormality (such as an odds ratio) is determined. If the value of likelihood of abnormality is below a predetermined threshold for the value of likelihood, then the test chromosome or the portion thereof is called as normal. If the value of likelihood of abnormality is above the predetermined threshold for the value of likelihood, the dosage of the test chromosome or portion thereof is re-measured using an assay with increased depth (for example, using a larger number of sequencing reads). A subsequent value of statistical significance is then determined using the re-measured dosage and a re-measured expected dosage. If the value of the subsequent value of statistical significance is above the predetermined threshold for the value of statistical significance, the test chromosome or portion thereof is called as abnormal. If the value of the subsequent value of statistical significance is below the predetermined threshold for the value of statistical significance, a subsequent value of likelihood is determined. If the subsequent value of likelihood is below the predetermined threshold for the value of likelihood, the test chromosome or portion thereof is called as normal. If the subsequent value of likelihood is above the predetermined threshold for the value of likelihood, the test chromosome or portion thereof is not called or, optionally, another round of dosage measurement and statistical analysis is performed using a further increased assay depth.

In some embodiments, the call of the test chromosome (e.g., normal (such as euploid or no microdeletion, abnormal (such as aneuploid or with microdeletion), or no call) is reported (for example, to a patient, a physician, or an institution) or displayed on a monitor. In some embodiments, a value determined using any of the methods described herein (for example, a value of statistical significance (such as a Z-score), a value of likelihood (such as an odds ratio), a percent fetal fraction, or a percentile fetal fraction) is reported or displayed on a monitor.

In some embodiments, a performance summary statistic for the method (such as a sensitivity value (such as a clinical sensitivity value or an analytic sensitivity value), a specificity value (such as a clinical specificity value or an analytical specificity value), a positive predictive value, or a negative predictive value) is determined, reported (for example, to a patient, a physician, or an institution), or displayed (such as on a monitor). The performance summary statistic can be used to measure the performance of the method, which can vary based on the fetal fraction and the sequencing depth for any given test sample. For example, higher depth sequencing can result in increased sensitivity and specificity of the method. Similarly, increased fetal fraction can result in increased sensitivity and specificity of the method. In some instances (for example, when analyzing a sample with low fetal fraction), it may be preferable to report or display a call of the test chromosome (e.g., normal (such as euploid or no microdeletion, abnormal (such as aneuploid or with microdeletion)) along with one or more performance summary statistics.

In some embodiments, one or more performance summary statistics are determined based on the measured fetal fraction of cell-free DNA in the test maternal sample. For example, in some embodiments, the summary statistic is determined based on a fetal fraction range, and the measured fetal fraction is within said range. In some embodiments, the summary statistic is determined based on a specific fetal fraction consistent with the measured fetal fraction. In some embodiments, the one or more performance summary statistics (such as a clinical sensitivity value and/or clinical specificity value) determined based on the fetal fraction of the sample are determined, reported, or displayed along with the call of the test chromosome. In some embodiments, the fetal fraction is further reported or displayed along with the call and the summary statistic.

Clinical sensitivity is the fraction of condition positive samples (i.e., a population of clinical validation samples) that are identified as positive by the method when applied in clinical testing. Analytical sensitivity is the fraction of condition positive samples (i.e., a population of analytical validation samples) that are identified as positive by the method when applied to known (and validated) samples. Clinical specificity is the fraction of condition negative samples that are identified as negative by the method when applied in clinical testing. Analytical specificity is the fraction of condition negative samples that are identified as negative by the method when applied to known (and validated) samples. Clinical sensitivity and specificity are generally lower than analytical sensitivity and specificity, respectively, as the clinical statistics incorporate confounding variation in performance from both biological (e.g., confined placental mosaicism) and technical (e.g., sample preparation and handling) origins that are not represented among analytical validation samples (i.e., confounding factors). Clinical sensitivity and specificity can be determined from post-method clinical validation experiments (e.g., chorionic villi sampling or amniocentesis) of a population of clinical validation samples (for example, more than 100 samples, more than 200 samples, or more than 500 clinical validation samples).

The relationship between clinical sensitivity for the method (based on the population of clinical validation samples) can be related to the analytic sensitivity using the formula:

$$Csens_{pop} = Asens_{pop} - \varepsilon sens_{pop}$$

wherein $Csens_{pop}$ is the clinical sensitivity for a population of clinical validation samples, $Asens_{pop}$ is the analytical sensitivity for a population of analytical validation samples, and $\varepsilon sens_{pop}$ is the reduction in analytical sensitivity caused by all confounding factors in the clinical validation population (such as those of biological or technical origin). Similarly, the relationship between clinical specificity for the method (based on the population of clinical validation samples) can be related to the analytic specificity using the formula:

$$Cspec_{pop} = Aspec_{pop} - \varepsilon spec_{pop}$$

wherein $Cspec_{pop}$ is the clinical specificity for a population of clinical validation samples, $Aspec_{pop}$ is the analytical specificity for a population of analytical validation samples, and $\varepsilon spec_{pop}$ is the reduction in analytical specificity caused by all confounding factors in the clinical validation population (such as those of biological or technical origin).

Because the clinical sensitivity and clinical specificity for the method are known (or can be determined) from a clinical validation experiment, and analytical sensitivity and analytical specificity for the method are known (or can be determined) from an analytical validation experiment, the values of $\varepsilon sens_{pop}$ and $\varepsilon spec_{pop}$ can be determined. The clinical and analytical sensitivity and specificity values (that is, $Csens_{pop}$, $Cspec_{pop}$, $Asens_{pop}$, $Aspec_{pop}$) and can be determined from a population of clinical validation samples comprising a distribution of all possible fetal fractions or from a subset of fetal fractions (for example, samples with a fetal fraction of about 3% or higher, about 3.5% or higher, about 4% or higher, about 4.5% or higher, about 5% or higher, about 6% or higher, about 7% or higher or about 8% or higher), which can be used to determine $\varepsilon sens_{pop}$ and $\varepsilon spec_{pop}$.

In some embodiments, it is assumed that the confounding factors for sensitivity and/or specificity do not vary as a function of fetal fraction. Thus, $\varepsilon sens_{pop}$ and $\varepsilon spec_{pop}$ can be considered independent of fetal fraction. Accordingly, clinical sensitivity for a subset population (for example, for samples with a specified fetal fraction or a fetal fraction within a specified fetal fraction range) can be determined according to the formula:

$$Csens_{subset} = Asens_{subset} - \varepsilon sens_{pop}$$

wherein $Csens_{subset}$ is the clinical sensitivity for the subset population, $Asens_{subset}$ is the analytical sensitivity (which can be known or determined) for analytical validation samples representative of the subset population, and $\varepsilon sens_{pop}$ is as determined above. Similarly, clinical specificity for the subset population can be determined according to the formula:

$$Cspec_{subset} = Aspec_{subset} - \varepsilon spec_{pop}$$

wherein $Cspec_{subset}$ is the clinical specificity for the subset population, $Aspec_{subset}$ is the analytical specificity (which can be known or determined) for analytical validation samples representative of the subset population, and $\varepsilon spec_{pop}$ is as determined above.

In some embodiments, it is not assumed that the confounding factors for sensitivity and/or specificity do not vary as a function of fetal fraction. The clinical sensitivity and clinical specificity for the subset population can then be determined by modifying the formulas above to:

$$Csens_{subset} = Asens_{subset} - (Ksens_{subset} \times \varepsilon sens_{pop})$$

and $$Cspec_{subset} = Aspec_{subset} - (Kspec_{subset} \times \varepsilon spec_{pop})$$

wherein $Ksens_{subset}$ and $Kspec_{subset}$ are scaling factors to adjust the magnitude of the confounding effects on clinical sensitivity and clinical specificity, respectively, relative to the full population used to determine $\varepsilon sens_{pop}$ or $\varepsilon spec_{pop}$ as a function of the population subset (e.g., particular subset of fetal fraction or range of fetal fraction). The scaling factors $Ksens_{subset}$ and $Kspec_{subset}$ can be determined, for example, by in silico simulation of a large number of simulated positive or negative samples at simulated fetal fractions. The simulated samples can be called using a calling algorithm, and the frequency of the correct call is determined, yielding the analytical sensitivity and specificity for the simulated samples.

Clinical sensitivity or clinical specificity (or other summary statistic) can be determined (and reported or displayed) based on the fetal fraction of the sample. In some embodiments, the clinical sensitivity or clinical specificity (or other summary statistic) is determine for a subset population with a fetal fraction within a particular range, such as between 0% and about 7% (for example, between 0% and about 0.5%, about 0.5% and about 1%, about 1% and about 1.5%, about 1.5% and about 2%, about 2% and about 2.5%, about 3% and about 3.5%, about 3.5% and about 4%, about 4% and about 4.5%, about 4.5% and about 5%, about 5% and about 5.5%, about 5.5% and about 6%, about 6% and about 6.5%, and about 6.5% and about 7%). In some embodiments, the range of fetal fraction is within 1% or narrower (such as within 0.5% or narrower, 0.25% or narrower, or 0.1% or narrower). Solely by way of example, in some embodiments a sample with a fetal fraction of about 2.9% could be reported with a clinical sensitivity or specificity (or other summary statistic) determined for fetal fraction with a range of about 2.5% to about 3.5%, about 2.5% to about 3%, about 2.75% to about 3%, about 2.8% to about 2.9%, or about 2.9% to about 3%. In some embodiments, the clinical sensitivity or specificity (or other summary statistic) can be determine for a specific fetal fraction, for example a sample with a fetal fraction of about 2.9% could be reported or displayed with a clinical sensitivity or specificity determined for a fetal fraction of about 2.9%. For example, a distribution of clinical sensitivity or specificity (or other summary statistic) is fit to a model (such as a linear regression model) and used to determine the clinical sensitivity or specificity (or other summary statistic) for the specific fetal fraction.

The clinical sensitivity and clinical specificity (which may be determined for a particular fetal fraction or range of fetal fraction) can be used to determine other summary statistics, such as positive predictive value (PPV) or negative predictive value (NPV) of the method. By using clinical sensitivity or clinical specificity determined for fetal fraction, the positive predictive value or negative predictive value is also determined for the fetal fraction.

Computing Systems

Figure 3:
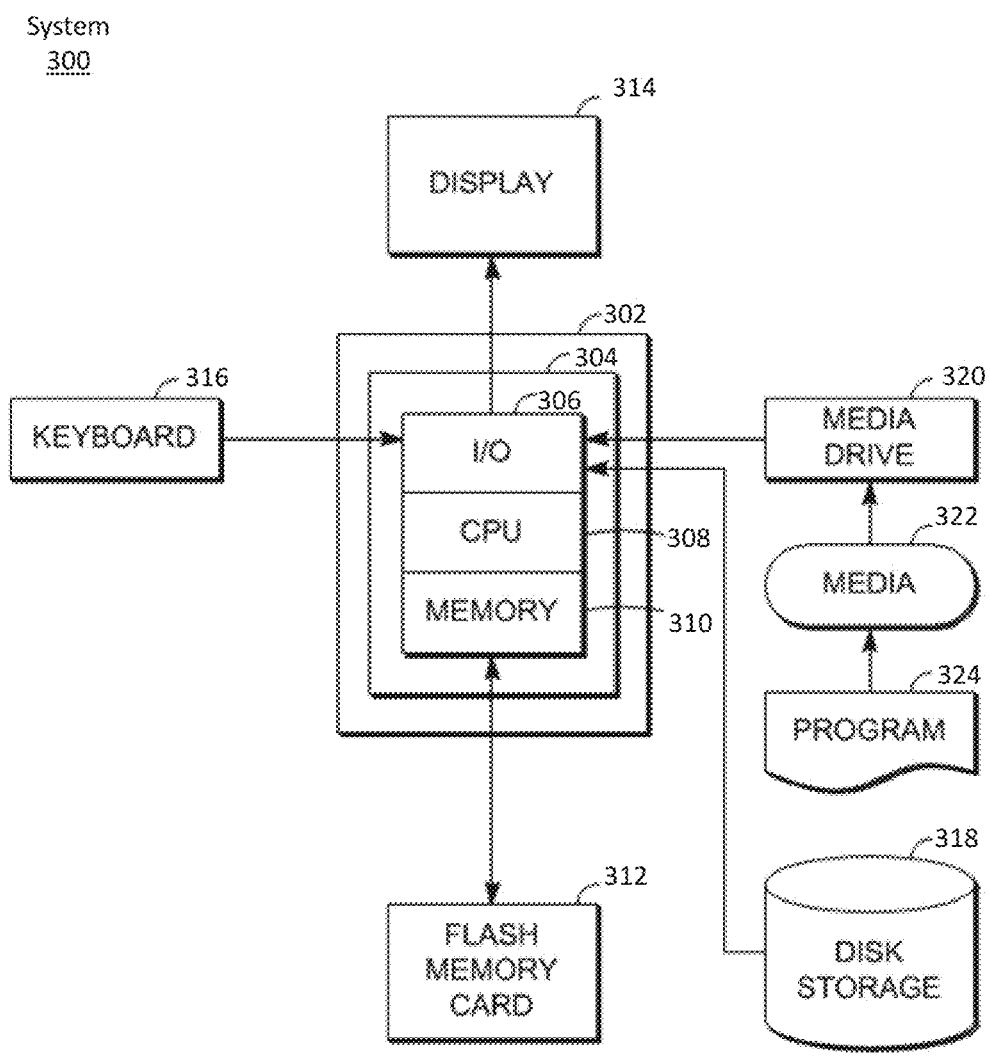
FIG. 3 depicts an exemplary computing system configured to perform processes described herein, including the various exemplary methods for determining a fetal chromosomal abnormality in a test chromosome or a portion thereof by analyzing a test maternal sample.

In some embodiments, the methods described herein are implemented by a program executed on a computer system. FIG. 3 depicts an exemplary computing system 300 configured to perform any one of the above-described processes, including the various exemplary methods for determining a fetal chromosomal abnormality in a test chromosome or a portion thereof by analyzing a test maternal sample. The computing system 300 may include, for example, a processor, memory, storage, and input/output devices (e.g., monitor, keyboard, disk drive, Internet connection, etc.). The computing system 300 may include circuitry or other specialized hardware for carrying out some or all aspects of the processes. For example, in some embodiments, the computing system includes a sequencer (such as a massive parallel sequencer). In some operational settings, computing system 300 may be configured as a system that includes one or more units, each of which is configured to carry out some aspects of the processes either in software, hardware, or some combination thereof.

FIG. 3 depicts computing system 300 with a number of components that may be used to perform the above-described processes. The main system 302 includes a motherboard 304 having an input/output ("I/O") section 306, one or more central processing units ("CPU") 308, and a memory section 310, which may have a flash memory card 312 related to it. The I/O section 306 is connected to a display 314, a keyboard 316, a disk storage unit 318, and a media drive unit 320. The media drive unit 320 can read/write a computer-readable medium 322, which can contain programs 324 and/or data.

At least some values based on the results of the above-described processes can be saved for subsequent use. Additionally, a non-transitory computer-readable medium can be used to store (e.g., tangibly embody) one or more computer programs for performing any one of the above-described processes by means of a computer. The computer program may be written, for example, in a general-purpose programming language (e.g., Pascal, C, C++, Java, Python, JSON, etc.) or some specialized application-specific language.

Various exemplary embodiments are described herein. Reference is made to these examples in a non-limiting sense. They are provided to illustrate more broadly applicable aspects of the disclosed technology. Various changes may be made and equivalents may be substituted without departing from the true spirit and scope of the various embodiments. In addition, many modifications may be made to adapt a particular situation, material, composition of matter, process, process act(s) or step(s) to the objective(s), spirit or scope of the various embodiments. Further, as will be appreciated by those with skill in the art, each of the individual variations described and illustrated herein has discrete components and features that may be readily separated from or combined with the features of any of the other several embodiments without departing from the scope or spirit of the various embodiments. All such modifications are intended to be within the scope of claims associated with this disclosure.

The following non-limiting examples further illustrate the methods of the present invention. Those skilled in the art will recognize that several embodiments are possible within the scope and spirit of this invention. While illustrative of the invention, the following examples should not be construed in any way limiting its scope.

EXEMPLARY EMBODIMENTS

Embodiment 1. A method for determining a chromosomal abnormality of a test chromosome or a portion thereof in a fetus by analyzing a test maternal sample of a woman carrying said fetus, wherein the test maternal sample comprises fetal cell-free DNA and maternal cell-free DNA, the method comprising:
  measuring a dosage of the test chromosome or the portion thereof in the test maternal sample;
  measuring a fetal fraction of cell-free DNA in the test maternal sample based an over- or under-representation of fetal cell-free DNA relative to maternal cell-free DNA from a plurality of bins within an interrogated region from the maternal sample; and
  determining an initial value of likelihood that the test chromosome or the portion thereof in the fetal cell-free DNA is abnormal based on the measured dosage, an expected dosage of the test chromosome or the portion thereof, and the measured fetal fraction.

Embodiment 2. The method of embodiment 1, wherein the over- or under-representation is determined based on a sequencing read count.

Embodiment 3. The method of embodiment 1, wherein the over- or under-representation is determined based on a count of binned probes hybridized to the interrogated region.

Embodiment 4. A method for determining a chromosomal abnormality of a test chromosome or a portion thereof in a fetus by analyzing a test maternal sample of a woman carrying said fetus, wherein the test maternal sample comprises fetal cell-free DNA and maternal cell-free DNA, the method comprising:
  measuring a dosage of the test chromosome or the portion thereof in the test maternal sample;
  measuring a fetal fraction of cell-free DNA in the test maternal sample based on a count of binned sequencing reads from an interrogated region from the maternal sample; and
  determining an initial value of likelihood that the test chromosome or the portion thereof in the fetal cell-free DNA is abnormal based on the measured dosage, an expected dosage of the test chromosome or the portion thereof, and the measured fetal fraction.

Embodiment 5. The method of any one of embodiments 1-4, wherein determining the initial value of likelihood comprises:
  determining an initial value of statistical significance for the test chromosome or the portion thereof based on the measured dosage and the expected dosage; and
  determining the initial value of likelihood based on the initial value of statistical significance and the measured fetal fraction.

Embodiment 6. The method of any one of embodiments 1-5, wherein determining the initial value of likelihood accounts for the probability that the measured fetal fraction is reflective of a true fetal fraction.

Embodiment 7. The method of embodiment 5 or 6, further comprising calling the test chromosome or the portion thereof to be abnormal if the absolute value of the initial value of statistical significance is above a predetermined threshold.

Embodiment 8. The method of embodiment 5 or 6, further comprising calling the test chromosome to be normal if the absolute value of the initial value of statistical significance is below a first predetermined threshold and the initial value of likelihood is below a second predetermined threshold.

Embodiment 9. The method of any one of embodiments 4-8, wherein the dosage is measured using an initial assay that generates an initial plurality of quantifiable products, wherein the number of quantifiable products in the initial plurality indicates the measured dosage.

Embodiment 10. The method of embodiment 9, further comprising:
  re-measuring the dosage of the test chromosome or the portion thereof using a subsequent assay that generates a subsequent plurality of quantifiable products from the test chromosome or the portion thereof if the initial value of likelihood is above a predetermined threshold; and
  determining a subsequent value of statistical significance for the test chromosome or the portion thereof based on the re-measured dosage.

Embodiment 11. The method of embodiment 9, further comprising:
  re-measuring the dosage of the test chromosome or the portion thereof using a subsequent assay that generates a subsequent plurality of quantifiable products from the test chromosome if the absolute value of the initial value of statistical significance is below a predetermined threshold; and
  determining a subsequent value of statistical significance for the test chromosome or the portion thereof based on the re-measured dosage.

Embodiment 12. The method of embodiment 9, further comprising:
  re-measuring the dosage of the test chromosome or the portion thereof using a subsequent assay that generates a subsequent plurality of quantifiable products from the test chromosome if the initial value of likelihood is above a predetermined threshold and the absolute value of the initial value of statistical significance is below a predetermined threshold; and
  determining a subsequent value of statistical significance for the test chromosome or the portion thereof based on the re-measured dosage.

Embodiment 13. The method of any one of embodiments 10-12, wherein the number of quantifiable products in the subsequent plurality indicates the re-measured dosage, and wherein the number of quantifiable products in the subsequent plurality is greater than the number of quantifiable products in the initial plurality.

Embodiment 14. The method of any one of embodiments 10-12, further comprising combining the number of quantifiable products in the initial plurality with the number of quantifiable products in the subsequent plurality, thereby resulting in a combined number of quantifiable products that indicates the re-measured dosage.

Embodiment 15. The method of any one of embodiments 10-14, further comprising calling the test chromosome or the portion thereof to be abnormal if the absolute value of the subsequent value of statistical significance is above a predetermined threshold.

Embodiment 16. The method of any one of embodiments 10-14, further comprising determining a subsequent value of likelihood that the fetal cell-free DNA is abnormal for the test chromosome or the portion thereof based on the re-measured dosage, the expected dosage of the test chromosome or portion thereof, and the measured fetal fraction.

Embodiment 17. The method of embodiment 16, further comprising calling the test chromosome or the portion thereof to be normal if the subsequent value of likelihood is below a predetermined threshold.

Embodiment 18. The method of any one of embodiments 9-17, wherein the quantifiable products are sequencing reads.

Embodiment 19. The method of any one of embodiments 9-17, wherein the quantifiable products are PCR products.

Embodiment 20. A method for determining a chromosomal abnormality of a test chromosome or a portion thereof in a fetus by analyzing a test maternal sample of a woman carrying said fetus, wherein the test maternal sample comprises fetal cell-free DNA and maternal cell-free DNA, the method comprising:
  measuring a dosage of the test chromosome or the portion thereof in the test maternal sample;
  measuring a fetal fraction of cell-free DNA in the test maternal sample based an over- or under-representation of fetal cell-free DNA relative to maternal cell-free DNA from a plurality of bins within an interrogated region from the maternal sample; and
  determining an initial value of statistical significance for the test chromosome or the portion thereof based on the measured dosage and an expected dosage of the test chromosome or the portion thereof.

Embodiment 21. The method of embodiment 20, wherein the over- or under-representation is determined based on a sequencing read count.

Embodiment 22. The method of embodiment 20, wherein the over- or under-representation is determined based on a count of binned probes hybridized to the interrogated region.

Embodiment 23. A method for determining a chromosomal abnormality of a test chromosome or a portion thereof in a fetus by analyzing a test maternal sample of a woman carrying said fetus, wherein the test maternal sample comprises fetal cell-free DNA and maternal cell-free DNA, the method comprising:
  measuring a dosage of the test chromosome or the portion thereof in the test maternal sample;
  measuring a fetal fraction of cell-free DNA in the test maternal sample based on a count of binned sequencing reads from an interrogated region from the maternal sample; and
  determining an initial value of statistical significance for the test chromosome or the portion thereof based on the measured dosage and an expected dosage of the test chromosome or the portion thereof.

Embodiment 24. The method of embodiment 23, further comprising calling the test chromosome or portion thereof to be abnormal if the initial value of statistical significance is above a first predetermined threshold.

Embodiment 25. The method of embodiment 23 or 24, wherein the chromosome dosage is measured using an assay that generates a plurality of quantifiable products, wherein the number of quantifiable products in the plurality indicates the measured chromosome dosage.

Embodiment 26. The method of embodiment 25, wherein the quantifiable products are sequencing reads.

Embodiment 27. The method of embodiment 25, wherein the quantifiable products are PCR products.

Embodiment 28. The method of any one of embodiments 1-27, wherein the dosage of the test chromosome or the portion thereof and the fetal fraction are measured in a simultaneous assay.

Embodiment 29. The method of any one of embodiments 1-28, wherein the dosage of a plurality of test chromosomes or portions thereof is simultaneously measured.

Embodiment 30. The method of any one of embodiments 1-29, wherein the fetal chromosomal abnormality is a microdeletion, and the one or more test chromosomes or the portion thereof is a putative microdeletion.

Embodiment 31. The method of embodiment 30, wherein the putative microdeletion is determined using circular binary segmentation.

Embodiment 32. The method of embodiment 30, wherein the putative microdeletion is determined using a hidden Markov model.

Embodiment 33. The method of any one of embodiments 1-29, wherein the fetal chromosomal abnormality is aneuploidy, and the one or more test chromosomes or the portion thereof is at least one complete chromosome.

Embodiment 34. The method of embodiment 33, wherein the test chromosome comprises chromosome 13, 18, 21, X, or Y.

Embodiment 35. The method of any one of embodiments 5-34, wherein the value of statistical significance is a Z-score, a p-value, or a probability.

Embodiment 36. The method of any one of embodiments 1-19 and 28-35, wherein the value of likelihood is an odds ratio.

Embodiment 37. The method of any one of embodiments 1-36, wherein the dosage of the test chromosome or the portion thereof is measured by:
  aligning sequencing reads from the test chromosome or portion thereof;
  binning the aligned sequencing reads in a plurality of bins;
  counting the number of sequencing reads in each bin; and
  determining an average number of reads per bin and a variation of the number of reads per bin.

Embodiment 38. The method of any one of embodiments 1-37, wherein the expected dosage for the test chromosome or the portion thereof is determined by:
  i. generating a dosage distribution vector comprising the measured dosage of at least one chromosome or portion thereof other than the test chromosome or portion thereof for each maternal sample in a plurality of maternal samples;
  ii. training a machine-learning model by regressing the dosage distribution vector onto the measured dosage of the test chromosome or portion thereof for each maternal sample in the plurality of maternal samples; and
  iii. applying the trained machine-learning model to a dosage distribution vector comprising the measured dosage of the at least one chromosome or portion thereof other than the test chromosome or portion thereof from the maternal sample to obtain the expected dosage for the test chromosome or the portion thereof in the test maternal sample.

Embodiment 39. The method of any one of embodiments 1-37, wherein the expected dosage for the test chromosome or the portion thereof is determined by:
  i. generating an average dosage vector comprising the average number of reads per bin from at least one chromosome or portion thereof other than the test chromosome or portion thereof for each maternal sample in a plurality of maternal samples;
  ii. training a dosage average machine-learning model by regressing the average dosage vector onto the average number of sequencing reads per bin from the test chromosome or portion thereof for each maternal sample in the plurality of maternal samples;
  iii. applying the trained dosage average machine-learning model to an average dosage vector comprising the average number of reads per bin from the least one chromosome or portion thereof other than the test chromosome or portion thereof from the maternal sample to obtain the expected average number of sequencing reads per bin for the test chromosome or the portion thereof in the test maternal sample;
  iv. generating a dosage variation vector comprising the variation of the number of reads per bin from at least one chromosome or portion thereof other than the test chromosome or portion thereof for each maternal sample in a plurality of maternal samples;
  v. training a dosage variation machine-learning model by regressing the dosage variation vector onto the variation of the number of sequencing reads per bin from the test chromosome or portion thereof for each maternal sample in the plurality of maternal samples; and
  vi. applying the trained dosage variation machine-learning model to a dosage variation vector comprising the variation of the number of reads per bin from the least one chromosome or portion thereof other than the test chromosome or portion thereof from the maternal sample to obtain the expected variation of the number of sequencing reads per bin for the test chromosome or the portion thereof in the test maternal sample.

Embodiment 40. The method of embodiment 38 or 39, wherein the at least one chromosome or portion thereof other than the test chromosome further comprises the test chromosome.

Embodiment 41. The method of any one of embodiments 38-40, wherein the plurality of maternal samples includes the test maternal sample.

Embodiment 42. The method of any one of embodiments 38-41, wherein the plurality of maternal samples does not include the test maternal sample.

Embodiment 43. The method of any one of embodiments 1-37, wherein the expected dosage for the test chromosome or the portion thereof is determined by measuring the dosage of at least one chromosome or portion thereof other than the test chromosome or portion thereof from the test maternal sample.

Embodiment 44. The method of any one of embodiments 1-37, wherein the expected dosage for the test chromosome or the portion thereof is determined by:
  measuring the dosage of a plurality of chromosomes or portions thereof other than the test chromosome or portion thereof from the test maternal sample; and
  determining an average dosage for the plurality of chromosomes or portions thereof.

Embodiment 45. The method of any one of embodiments 1-37, wherein the expected dosage for the test chromosome or the portion thereof is determined by:
  measuring the dosage of the test chromosome or the portion thereof from a plurality of maternal samples other than the test maternal sample; and
  determining an average dosage for the test chromosome or portions thereof from the plurality of maternal sample other than the test maternal sample.

Embodiment 46. The method of any one of embodiments 1-45, wherein measuring the fetal fraction comprises:
  aligning the sequencing reads from the interrogated region;
  binning the aligned sequencing reads from the interrogated region in a plurality of binds;
  counting the number of sequencing reads in each of at least a portion of the bins; and
  determining the measured fetal fraction based on the number of sequencing reads in the at least a portion of the bins using a trained machine-learning model.

Embodiment 47. The method of embodiment 46, wherein the machine-learning model is trained by:
  i. for each training maternal sample in a plurality of training maternal samples, wherein each training maternal sample has a known fetal fraction of cell-free DNA:
    aligning sequencing reads from the interrogated region,
    binning the aligned sequencing reads from the interrogated region in a plurality of bins, and
    counting the number of sequencing reads in each bin; and
  ii. determining one or more model coefficients based on the number of sequencing reads in each bin and the known fetal fraction for each training maternal sample in the plurality of training maternal samples.

Embodiment 48. The method of embodiment 47, wherein the maternal samples are taken from women with male pregnancies, and the known fetal fraction is determined by quantifying an amount of Y chromosome, X chromosome, or a known aneuploid chromosome in the maternal sample.

Embodiment 49. The method of any one of embodiments 46-48, wherein the machine-learning model is a regression model.

Embodiment 50. The method of any one of embodiments 46-49, wherein the machine-learning model is a linear regression model.

Embodiment 51. The method of any one of embodiments 46-49, wherein the machine learning model is a ridge regression model.

Embodiment 52. The method of any one of embodiments 46-51, wherein determining the measured fetal fraction comprises adjusting the fetal fraction predicted by the machine-learning model using polynomial smoothing.

Embodiment 53. The method of any one of embodiments 46-52, wherein determining the measured fetal fraction comprises adjusting the fetal fraction determined by the machine-learning model or determined after polynomial smoothing using a scalar factor that accounts for differences between the male and female pregnancies.

Embodiment 54. The method of any one of embodiments 46-53, wherein the interrogated region comprises at least a portion of a chromosome other than the test chromosome or the portion thereof.

Embodiment 55. The method of any one of embodiments 46-54, wherein the interrogated region comprises at least a whole chromosome other than the test chromosome.

Embodiment 56. The method of any one of embodiments 46-55, wherein the interrogated region comprises a plurality of chromosomes.

Embodiment 57. The method of any one of embodiments 46-56, wherein the interrogated region does not include an X chromosome or a Y chromosome.

Embodiment 58. The method of any one of embodiments 46-57, wherein the interrogated region does not include the test chromosome.

Embodiment 59. The method of any one of embodiments 37-58, further comprising normalizing the number of sequencing reads prior to counting the number of sequencing reads.

Embodiment 60. The method of embodiment 59, wherein the sequencing reads are normalized for variations in GC content or read mappability.

Embodiment 61. The method of any one of embodiments 37-60, wherein each bin is between about 10 kilobases to about 80 kilobases in length.

Embodiment 62. The method of any one of embodiments 1-61, wherein the test maternal sample is obtained from a woman with a body mass index of about 30 or more.

Embodiment 63. The method of any one of embodiments 1-62, wherein the test maternal sample is obtained from a woman with a body mass index of about 30 to about 40.

Embodiment 64. The method of any one of embodiments 1-63, wherein the method is implemented by a program executed on a computer system.

Embodiment 65. The method of any one of embodiments 1-64, further comprising reporting an aneuploidy call for the test chromosome, a microdeletion call for the portion of the test chromosome, a value of statistical significance, a value of likelihood that the fetal cell-free DNA is abnormal in the test chromosome or the portion thereof, a percent fetal fraction, or a percentile fetal fraction.

Embodiment 66. The method of any one of embodiments 1-65, further comprising reporting a performance summary statistic.

Embodiment 67. The method of embodiment 66, wherein the performance summary statistic is a clinical specificity, a clinical sensitivity, a positive predictive value, or a negative predictive value.

Embodiment 68. The method of embodiment 66 or 67, wherein the performance summary statistic is determined based on the measured fetal fraction of cell-free DNA in the test maternal sample.

Embodiment 69. The method of embodiment 68, wherein the performance summary statistic is determined based on a fetal fraction range, and the measured fetal fraction is within said range.

Embodiment 70. The method of embodiment 68, wherein the performance summary statistic is determined based on a specific fetal fraction consistent with the measured fetal fraction.

Embodiment 71. The method of any one of embodiments 1-70, comprising determining a performance summary statistic for the method.

Embodiment 72. The method of any one of embodiments 1-71, wherein the fetal fraction is less than about 4%.

Embodiment 73. The method of any one of embodiments 1-72, wherein the fetal fraction is about 3% or less.

Embodiment 74. The method of any one of embodiments 1-73, wherein the fetal fraction is between about 1% and less than about 4%.

EXAMPLES

Example 1: Fetal Fraction Determination

Cell-free DNA of 1249 maternal samples taken from women with male pregnancies was sequenced by massively parallel sequencing. For each maternal sample, the sequencing reads from each chromosome were aligned using a reference genome, binned in a plurality of bins, and the number of sequencing reads in each bin were counted. The bins were each 20 kilobases in length, giving approximately 155,000 bins across the genome. The counted reads were normalized to account for GC correction, bin mappability, and median scaling. For median scaling, the count in each bin in any given sample was divided by the median value across all bins in that sample, thus making the bin counts centered at 1.0, or a log 2 value centered at 0. At least 15e6 genome-wide sequencing reads were obtained for each maternal sample, with the average number of reads being about 17e6 genome-wide sequencing reads.

The measured fetal fraction, $FF_o$, for each maternal sample was determined by independently calculating the fetal fraction based on the median normalized reads per bin from the X chromosome and the median normalized reads per bin from the Y chromosome, each compared to the global average for those chromosomes in female samples. The percent fetal fraction based on the number of reads per bin from the X chromosome was calculated as:

$$FF_X = 2(\mu_{X,exp} - \mu_{X,m})$$

wherein $\mu_{X,exp}$ is the expected dosage of chromosome X and $\mu_{X,m}$ is the measured dosage of chromosome X. The percent fetal fraction based on the number of reads per bin from the Y chromosome was calculated as:

$$FF_Y = 2(\mu_{Y,m} - \mu_{Y,exp})$$

wherein $\mu_{Y,exp}$ is the expected dosage of chromosome Y and $\mu_{Y,m}$ is the measured dosage of chromosome Y. The expected dosage of chromosome X is determined based on normalized binned sequencing reads from autosomal chromosomes using a regression-model trained using maternal samples only from female pregnancies. The expected dosage of chromosome Y is determined using the median normalized read counts per bin (and is thus, near zero since this value is obtained from female pregnancies), and the measured dosage of chromosome Y is determined using the median normalized read counts per bin in the test sample.

The fetal fraction based on the number of reads per bin from the X chromosome and the fetal fraction based on the number of reads per bin from the Y chromosome were inconsistent. To account for this inconsistency, a linear fit was used to model the general relationship between $FF_X$ and $FF_Y$ across all samples, and the slope (1.07) and intercept (2.5%) from this fit scaled $FF_X$ to yield a fetal fraction inferred from the X chromosome, $FF_{IX}$. The recorded observed fetal fraction was then calculated as:

$$FF_o = \frac{FF_Y + FF_{IX}}{2}$$

A linear regression model was trained using the set of maternal samples by regressing a bin-count vector representing the bin count for each bin (across all autosomal chromosomes in the genome) onto the observed (i.e., known) fetal fraction of each sample. As the about 1500 maternal samples were used to train the linear regression model, they can be referred to as training maternal samples.

Figure 4:
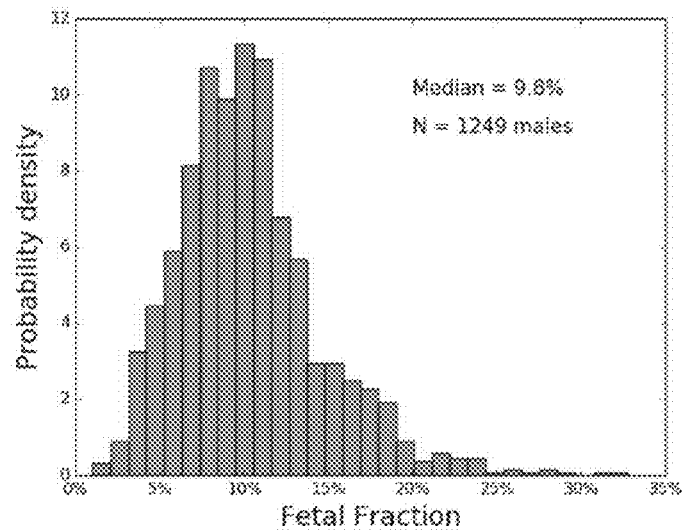
FIG. 4 is a distribution of an observed fetal fraction for 1249 samples, with a median fetal fraction of 9.8%, as determined by a measured and expected dosage of the X chromosome and Y chromosome.
Figure 5:
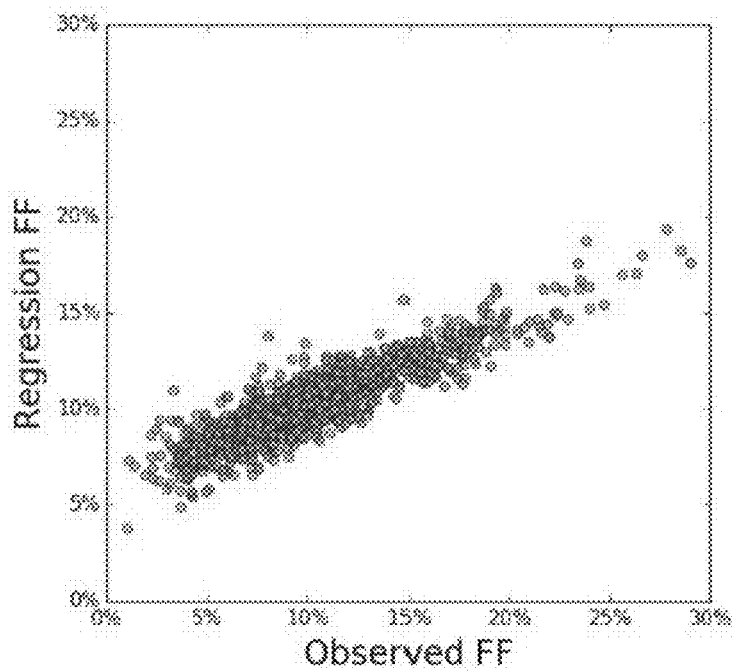
FIG. 5 illustrates a determined regression fetal fraction (determined using a linear regression model) plotted against the observed fetal fraction, as determined by a measured dosage of the X chromosome and Y chromosome.

The fetal fraction for 1249 additional maternal samples was determined using the trained regression model. For each maternal sample, the sequencing reads from each chromosome were aligned using a reference genome, binned in a plurality of bins, and the number of sequencing reads in each bin were counted and normalized using the same methods as for the maternal samples used to train the linear regression model. Additionally, an observed fetal fraction was calculated using the same methods as for the maternal samples used to train the linear regression model (that is, by using the sequencing reads from the X chromosome and the Y chromosome). The observed fetal fraction for the 1249 samples is plotted as a distribution shown in FIG. 4, with a median fetal fraction of 9.8%. The bin-count vector for each maternal sample was used as an input for the trained model, which determined a fetal fraction (which can be referred to as the "regression fetal fraction"). The determined regression fetal fraction was plotted against the observed fetal fraction, which is illustrated in FIG. 5.

Figure 6:
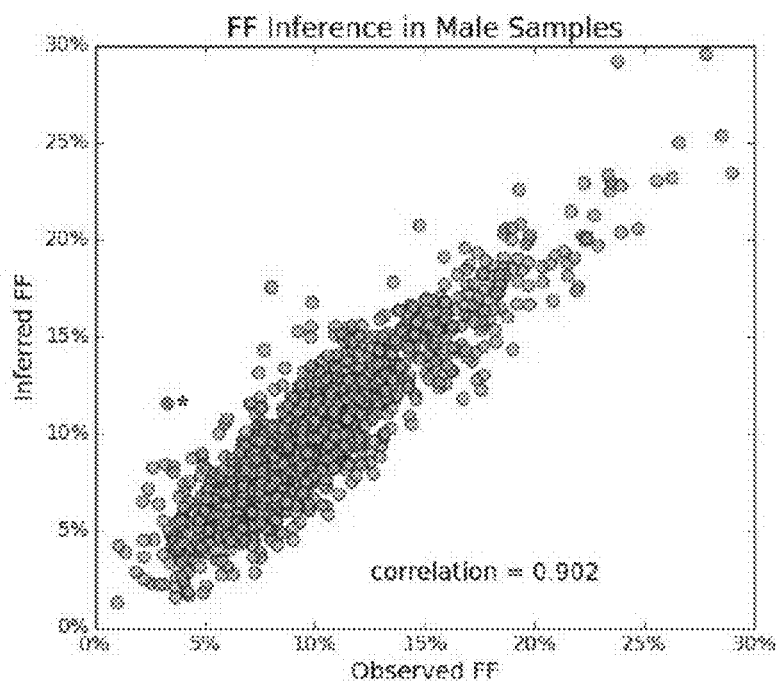
FIG. 6 illustrates an inferred fetal fraction, as determined using a linear regression model and adjusting the predicted fetal fraction based on predicted fetal fraction percentiles plotted against the observed fetal fraction, as determined by a measured dosage of the X chromosome and Y chromosome.

The regression fetal fractions predicted by the trained linear regression model correlated with the observed fetal fractions, although the intercept and slope were not 0 and 1, respectively. To normalize the regression fetal fraction to match the observed fetal fraction, an inferred fetal fraction was determined by computing the percentile of any given regression fetal fraction and adjusting the fetal fraction to an equivalent percentile of the observed fetal fraction distribution from the training maternal samples. Plotting the inferred fetal fraction against the observed fetal fraction results in a correlation coefficient of 0.902. See FIG. 6. A single outlier was observed (noted with an asterisk (*) in FIG. 6), which may be due to a high-noise female that was inadvertently characterized as a male pregnancy, or could be due to a vanishing male twin.

The trained linear regression model was then used to determine the fetal fraction in 26 maternal samples with female pregnancies with previously detected trisomy for chromosome 21. The bin density for chromosome 21 was used to determine an observed fetal fraction as follows:

$$FF_{21} = 2(\mu_{21,m} - \mu_{21,exp})$$

Figure 7:
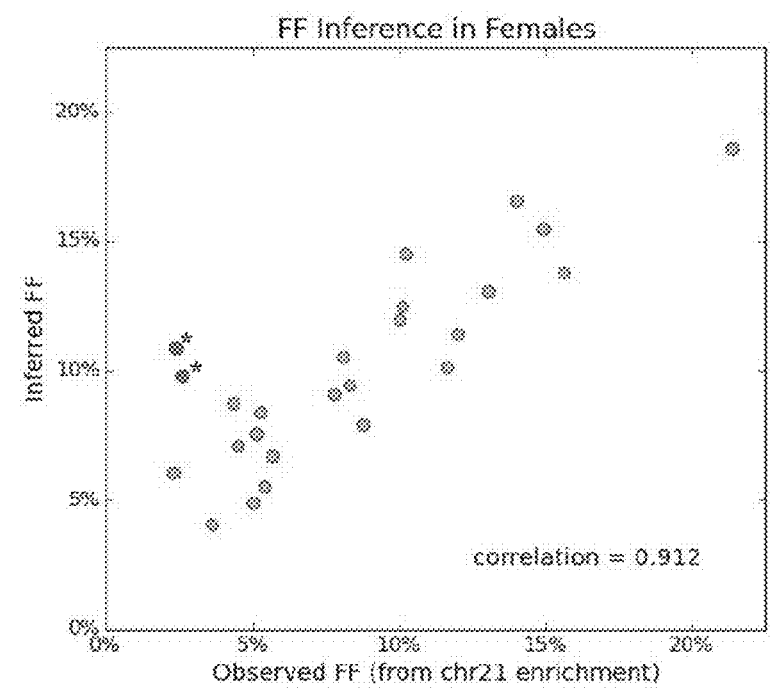
FIG. 7 illustrates an inferred fetal fraction from 26 trisomy 21 pregnancies, as determined using a linear regression model and adjusting the fetal fraction based on fetal fraction percentiles plotted against the observed fetal fraction, as determined by a measured dosage of the X chromosome and Y chromosome.

The fetal fraction for the 26 maternal samples was then determined using the linear regression model that was trained using the 1249 training maternal samples, as described above. The entire genome for each of the 26 maternal samples was sequenced, aligned, binned, and the number of sequencing reads in each bin was normalized and counted, thereby generating bin-count vectors for each of the maternal samples. The bin-count vectors were used as an input into the trained linear regression model to generate a regression fetal fraction for each maternal sample. An inferred fetal fraction was then determined by normalizing the percentiles as described above. Plotting the inferred fetal fraction against the observed fetal fraction results in a correlation coefficient of 0.912, after excluding two outliers (noted with an asterisk (*)). See FIG. 7. Upon retesting the two outlier samples at a higher sequencing depth, it was determined that these samples were false positives for chromosome 21 trisomy (that is, they were euploid for chromosome 21). Thus, the observed fetal fraction for these outliers was incorrectly determined (as the formula for determining fetal fraction assumed trisomy), at the correct fetal fraction was about 10%, near the fetal fraction inferred by the trained linear regression model.

Example 2: Fetal Fraction Determination with Low Sequencing Depth

Figure 8:
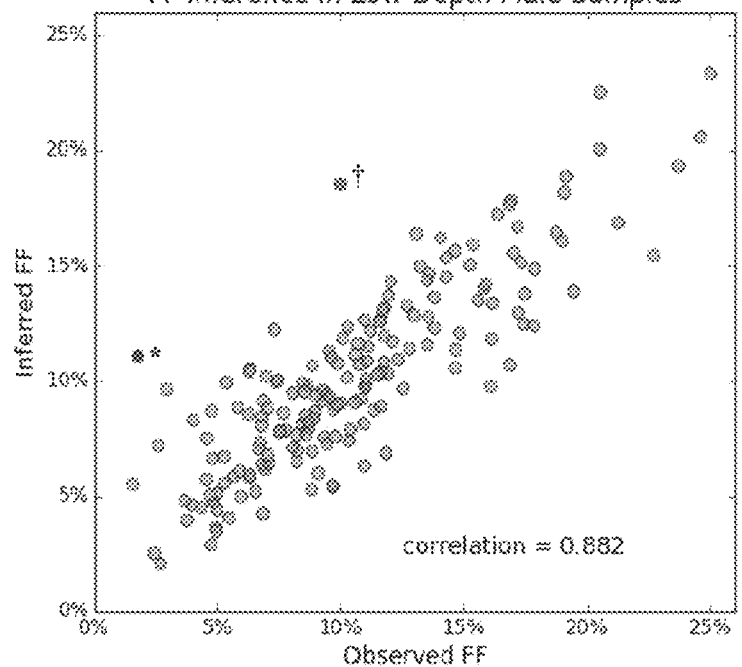
FIG. 8 illustrates an inferred fetal fraction for 180 low sequencing depth samples using a linear regression model and adjusting the fetal fraction based on fetal fraction percentiles plotted against the observed fetal fraction, as determined by a measured dosage of the X chromosome and Y chromosome.

Fetal fraction was measured using the trained linear regression model (trained using the 1249 training samples, as described in Example 1) for 180 low sequencing depth samples (sequencing depth was between 8e6 and 12e6 reads across the whole genome), and normalized using the percentiles of the regression fetal fractions. The observed fetal fraction was determined using the median reads per bin from the X chromosome and the median reads per bin from the Y chromosome, as described above. Measured fetal fractions of the 180 maternal samples were plotted against the observed fetal fractions, with a correlation coefficient of 0.882, excluding two outliers. See FIG. 8. For the outlier marked with an asterisk (*) in FIG. 8, the fetus was likely monosomy X, with only residual chromosome Y signal, causing an incorrect fetal fraction determination using binned sequencing reads from both the X chromosome and the Y chromosome. The measured fetal fraction of about 12% is likely correct, as this fetal fraction is close to the observed fetal fraction when determined using only sequencing reads from the X chromosome. The outlier marked with a dagger (†) had a skewed GC normalization and elevated signal from chromosome 6, which could indicate a vanishing twin.

Example 3: Fetal Aneuploidy Determination

To elucidate the relationship between sensitivity and sequencing depth, mock samples at arbitrary fetal fraction and read depth were constructed by mixing empirical sequencing data in silico. Maternal samples with fetal cfDNA that are trisomic for chromosome 13 (n=5), trisomic for chromosome 18 (n=3), trisomic for chromosome 21 (n=6), or monosomic for chromosome X (n=4), each with a known fetal fraction determined using sequencing read density (reads per bin) from the Y chromosome and X chromosome (fetal fraction for those pregnancies with monosomy chromosome X was determined using only the X chromosome), or samples from non-pregnant women (n=5) were sequenced using massively parallel sequencing at a whole-genome read depth of about 100 million reads. The reads from each sample were split into ~200 slices of 500,000 reads, and 245,000 simulated maternal samples were generated by randomly blending read slices from aneuploid samples and non-pregnant samples to obtain aneuploidy samples with various read depths and fetal fractions. For instance, mixing 10 slices from a 4% fetal fraction sample with 10 slices from a non-pregnant sample would lead to a 10-million-read sample (from the 20 slices at 500,000 reads per slice) at 2% fetal fraction. Fetal fraction for the simulated samples was determined by:

$$FF_{sim} = FF_{preg}\left(\frac{n_{preg}}{n_{preg} + n_{nonpreg}}\right)$$

wherein $FF_{sim}$ is the simulated fetal fraction, $FF_{preg}$ is the fetal fraction from the pregnant maternal sample, $n_{preg}$ is the number of slices from the pregnant sample, and $n_{nonpreg}$ is the number of slices from the non-pregnant sample. Read depths of the simulated maternal samples were either 7 million reads, 9.5 million reads, 12 million reads, 14.5 million reads, 17 million reads, or 50 million reads. The simulated maternal samples were analyzed within a batch of 109 other samples, where reads for the other samples were subsampled to yield an average read depth of 9.5 million reads, 12 million reads, 14.5 million reads, or 17 million reads (since the typical average depth for a batch is 17 million reads, no subsampling was needed to achieve a batch-average depth of 17 million).

Figure 9:
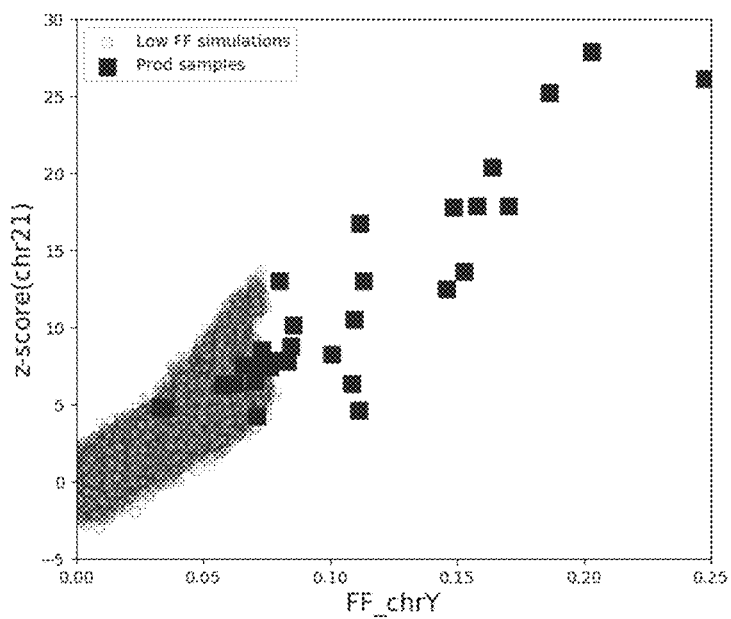
FIG. 9 presents Z-scores for chromosome 21 from known (known samples are labeled "Prod" or "Production" samples or simulated trisomy 21 samples plotted against observed fetal fraction as determined by a measurement using the Y chromosome.

To verify that the simulated reads resembled actual samples, a Z-score was determined for the simulated samples with chromosome 21 trisomy and 30 real maternal samples with chromosome 21 trisomy. The fetal fraction for the real maternal samples was determined using sequencing read density (reads per bin) from the Y chromosome. The fetal fraction of the simulated maternal samples ranged from about 0% to about 8%, whereas the fetal fraction from the real samples was as high as about 25%. The Z-scores were plotted against the measured or simulated fetal fractions. See FIG. 9. The simulated maternal samples were found to behave similar to the real maternal samples.

Figure 10A:
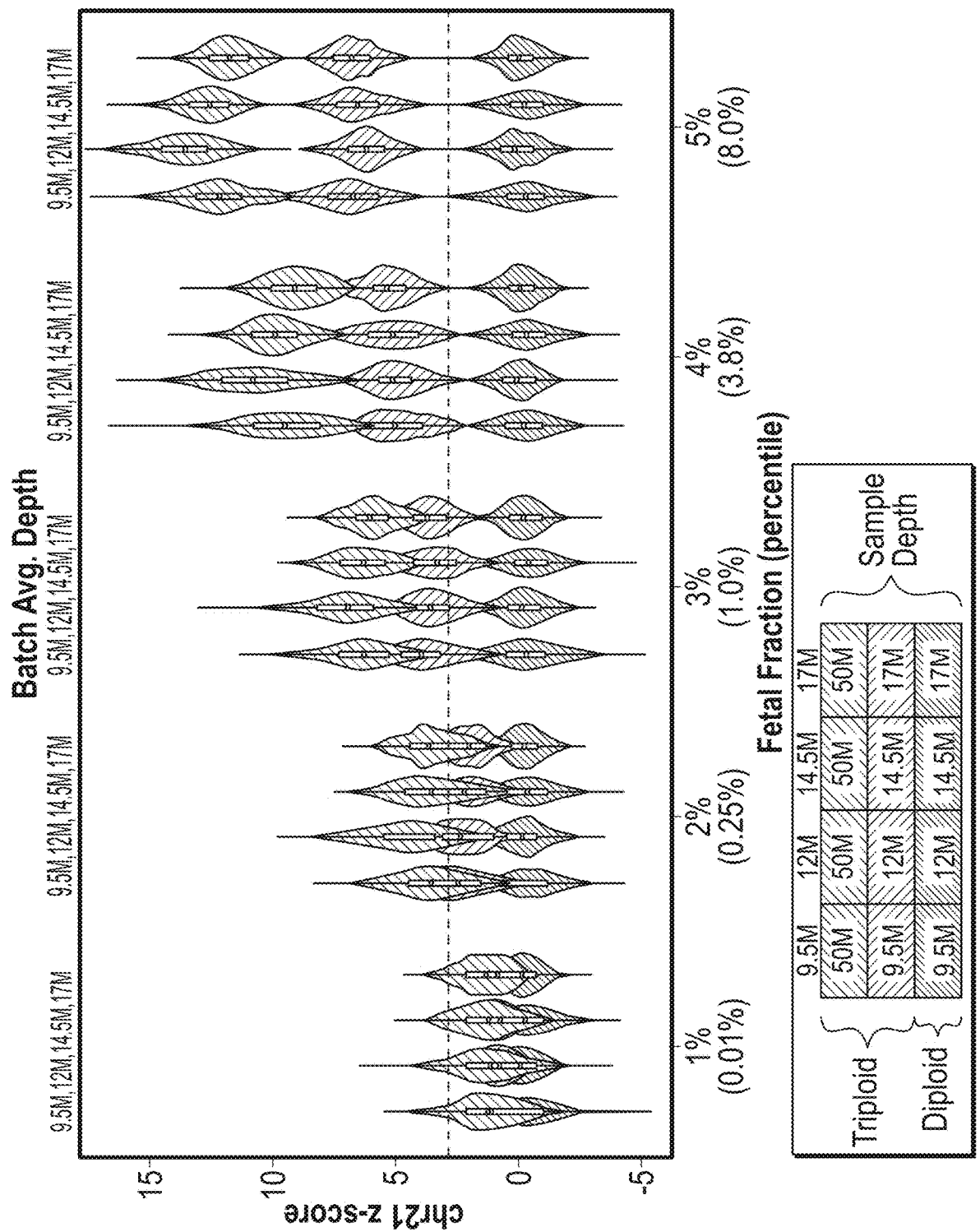
FIG. 10A shows the distribution of Z-scores (chromosome 21) observed from analyzing simulated samples at varying fetal fractions, sequencing depths (batch average and sample depth), and ploidy status.

FIG. 10A shows the distribution of Z-scores (chromosome 21) observed from analyzing a variety of simulated samples. Each simulated sample had the indicated ploidy ("Diploid" or "Triploid"), "Sample depth" (indicated by shading; see figure legend), and fetal fraction (X-axis), and was analyzed in the context of a batch of 109 other samples, where the other samples had an average depth of the indicated "Batch Average Depth". The Z-scores for simulated maternal samples with triploid or diploid chromosome 21 for each average sequencing read depth batch (average sequencing read depth of 9.5 million sequencing reads, 12 million sequencing reads, 14.5 million sequencing reads, or 17.5 million sequencing reads) at 1% (0.01 percentile), 2% (0.25 percentile), 3% (1.0 percentile), 4% (3.8 percentile), or 5% (8.0 percentile) are plotted in FIG. 10A. Also plotted are Z-scores for those simulated samples where the simulated sample alone has a read depth of 50 million sequencing reads (and the average depth for other 109 samples in the batch is indicated). The dashed line in FIG. 10A indicates a Z-score of 3, which is an exemplary predetermined threshold for calling aneuploidy. The Z-score did not increase for diploid samples at any sequencing depth or fetal fraction, as the sequencing depth of a diploid sample has a read count for the test chromosome (chromosome 21) that is close to the expected read count. Z-scores for diploid samples were taken from the chromosome 21 Z-score for samples that were triploid 13, triploid 18, or monosomy X. For triploid samples, however, the Z-score increases as a function of fetal fraction and sequencing depth, as the difference between the median number of reads per bin for the test chromosome dosage and the median number of reads per bin for the expected chromosome dosage increases as a function of the fetal fraction, and the variation—i.e., the standard deviation or interquartile range—of the chromosome dosage decreases as a function of sequencing read depth.

Figure 10B:
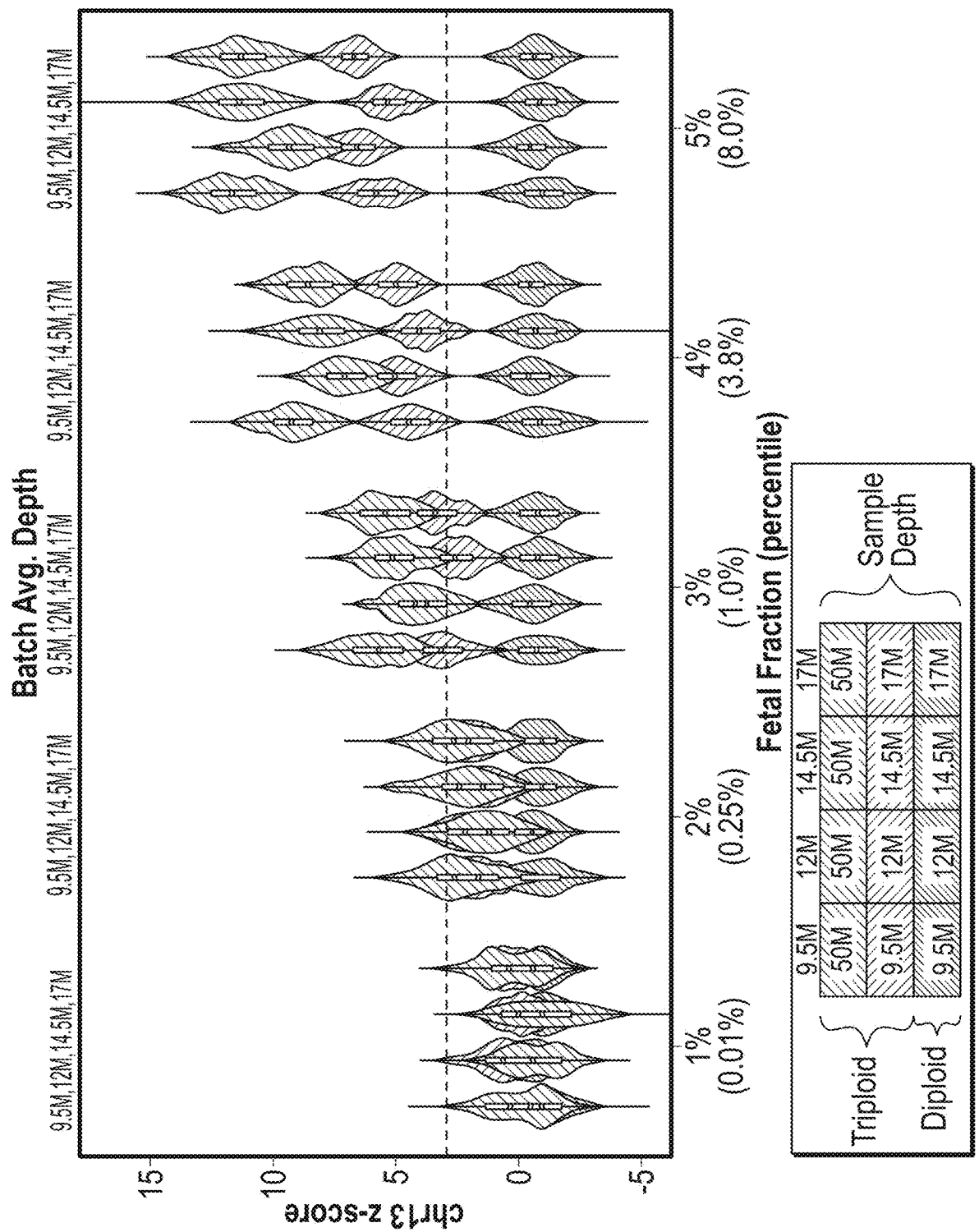
FIG. 10B shows the distribution of Z-scores (chromosome 13) observed from analyzing simulated samples at varying fetal fractions, sequencing depths (batch average and sample depth), and ploidy status.
Figure 10C:
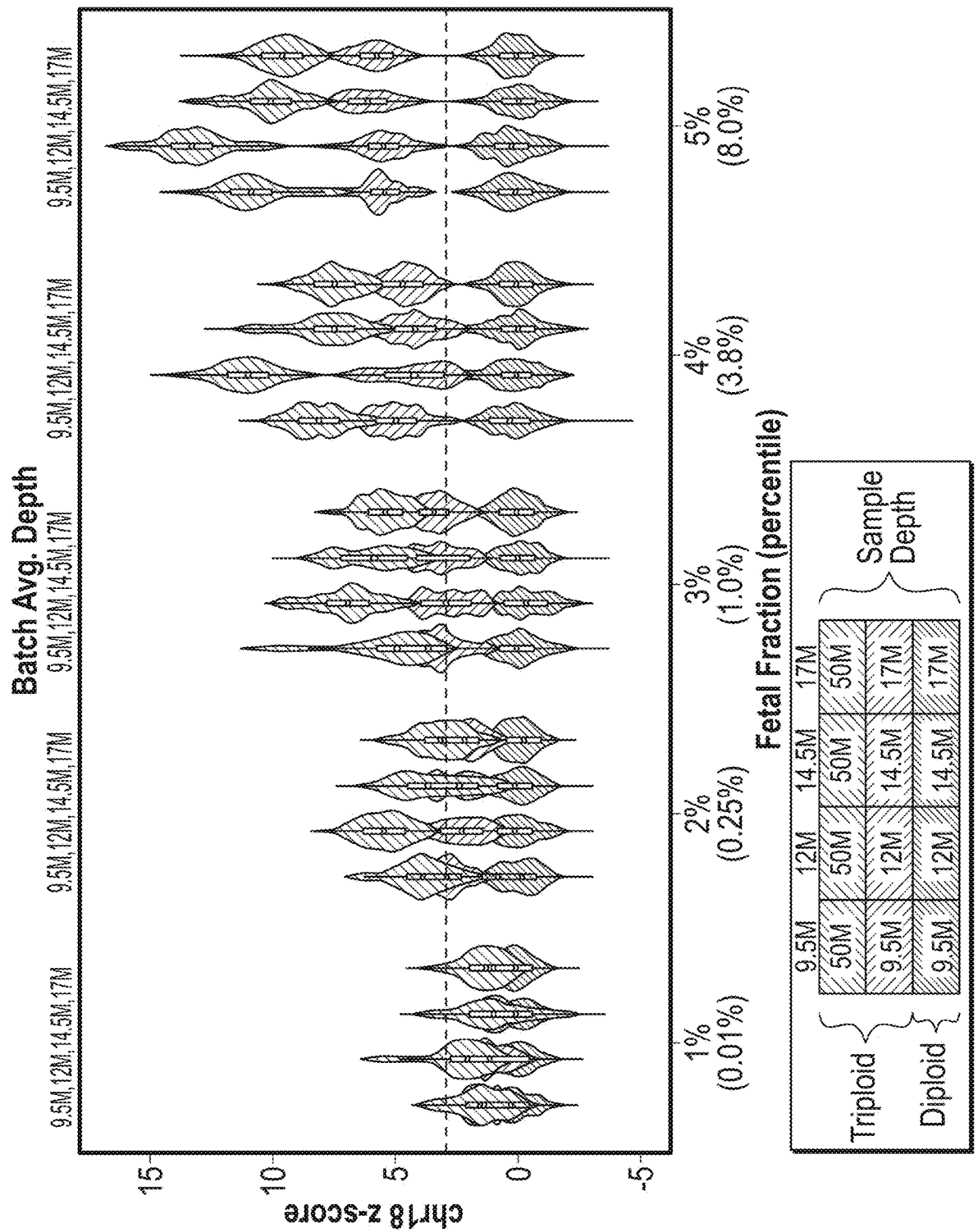
FIG. 10C shows the distribution of Z-scores (chromosome 18) observed from analyzing simulated samples at varying fetal fractions, sequencing depths (batch average and sample depth), and ploidy status.
Figure 10D:
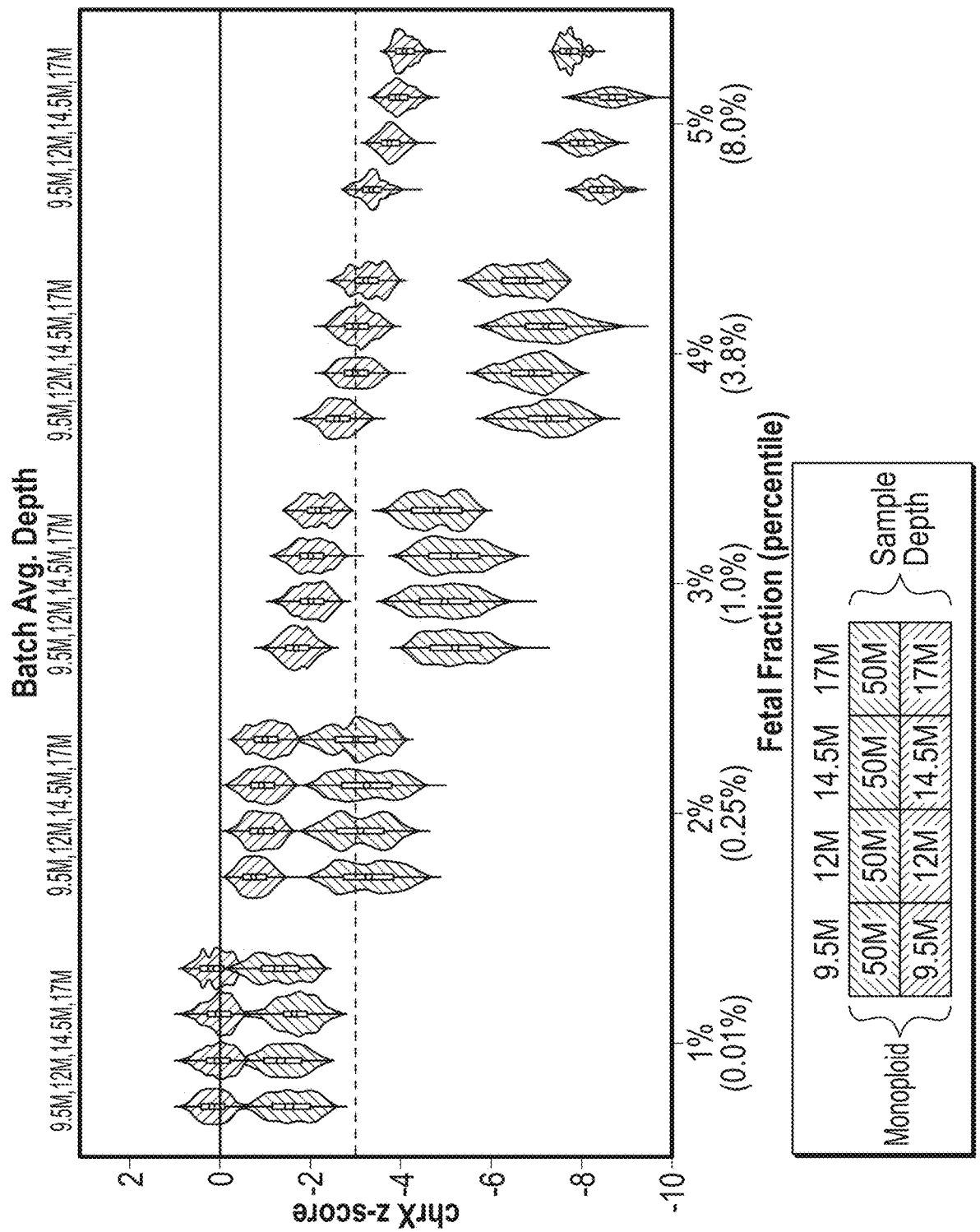
FIG. 10D shows the distribution of Z-scores (X chromosome) observed from analyzing simulated monosomy X samples at varying fetal fractions and sequencing depths (batch average and sample depth).

FIGS. 10B, 10C, and 10D illustrate plots similar to FIG. 10A, except the simulated maternal samples had fetal cfDNA trisomic for chromosome 13 (FIG. 10B), trisomic for chromosome 18 (FIG. 10C), or monosomic for chromosome X (i.e., MX and without a Y chromosome; FIG. 10D). Diploid chromosome X was omitted from FIG. 10D because all simulated non-monosomic chromosome X samples were male (XY), and thus not diploid for chromosome X.

Example 4: Sensitivity and Specificity Using Dynamic Iterative Depth Optimization The sensitivity of detecting fetal aneuploidy using a dynamic iterative depth optimization (DIDO) method was compared to the sensitivity of detecting fetal aneuploidies without dynamic iterative depth optimization as a function of measured fetal fraction. For the measurement of sensitivity to fetal aneuploidy without dynamic iterative depth optimization, samples were (1) assigned fetal fraction value based on random selection from the empirical fetal-fraction distribution, (2) assigned a Z-score by randomly selecting from the aneuploid distribution for 17 million reads for the modeled aneuploidy of interest (FIG. 10A-D), and (3) assigned a call of aneuploidy if Z>3 and euploid if Z<3. Since all samples were modeled as aneuploidy, euploid calls were false negatives, and sensitivity therefore was determined as:

$$\text{Sensitivity} = 1 - \frac{\text{number of false calls}}{\text{number of total calls}}$$

For the measurement of sensitivity to fetal aneuploidy with dynamic iterative depth optimization, samples were (1) assigned fetal fraction value based on random selection from the empirical fetal-fraction distribution, (2) assigned a Z-score by randomly selecting from the aneuploid distribution for 17 million reads for the modeled aneuploidy of interest (FIG. 10A-D), and (3) called aneuploid if the Z-score is greater than 3; called euploid if both Z-score is less than 3 and the value of likelihood of aneuploidy less than 0.2; reflexed back to step (2) but with 50 million read depth if both the Z-score is less than 3 and value of likelihood of aneuploidy is greater than 0.2. Again, since all samples were modeled as aneuploidy, euploid calls were false negatives.

Detection of fetal aneuploidy with dynamic iterative depth optimization is performed with high sensitivity and high specificity for maternal samples with a fetal fraction at least as low as 2% (~0.25 percentile). Table 2 indicates the sensitivity for trisomy in chromosomes 13 (Patau syndrome), 18 (Edwards syndrome), or 21 (Down syndrome), or monosomy in chromosome X (Turner syndrome) across all fetal fractions using methods for detecting fetal aneuploidy without dynamic iterative depth optimization ("Without DIDO"), with dynamic iterative depth optimization ("DIDO"), and with dynamic iterative depth optimization and fetal fraction for male pregnancies based on the Y chromosome ("DIDO plus Y").

TABLE 2

Analytical Sensitivity of Fetal Aneuploidy Detection

| Test Chromosome | Without DIDO | DIDO | DIDO plus Y |
|---|---|---|---|
| Trisomy 21 (T21) | 0.95 | 0.97 | 0.98 |
| Trisomy 13 (T13) | 0.96 | 0.98 | 0.99 |
| Trisomy 18 (T18) | 0.97 | 0.99 | 0.99 |
| Monosomy X (MX) | 0.92 | 0.97 | N/A* |

*DIDO plus Y is not relevant for MX due to the absence of the Y chromosome.

Even more significant gains in sensitivity for fetal aneuploid detection can be seen when considering maternal samples with the fetal fraction between 2% and 5% (0.25 percentile and 8 percentile). See Table 3.

TABLE 3

Analytical Sensitivity of Fetal Aneuploidy Detection
(Fetal Fraction 2%-5%)

| Test Chromosome | Without DIDO | DIDO | DIDO plus Y |
|---|---|---|---|
| Trisomy 21 (T21) | 0.62 | 0.76 | 0.84 |
| Trisomy 13 (T13) | 0.67 | 0.80 | 0.88 |
| Trisomy 18 (T18) | 0.74 | 0.88 | 0.94 |
| Monosomy X (MX) | 0.46 | 0.85 | N/A* |

*DIDO plus Y is not relevant for MX due to the absence of the Y chromosome.

The dynamic iterative depth optimization method performs not only with high sensitivity, but also with high specificity, including for maternal samples with low fetal fraction. This is shown in Table 4.

TABLE 4

Analytical Sensitivity and Analytical Specificity of
Fetal Aneuploidy Detection with DIDO

| | Fetal Fraction >4% | | Fetal Fraction 2%-4% | |
|---|---|---|---|---|
| Test Chromosome | Analytical sensitivity | Analytical specificity | Analytical sensitivity | Analytical specificity |
| Trisomy 21 (T21) | >0.99 | >0.998 | 0.818 | >0.998 |
| Trisomy 13 (T13) | >0.99 | >0.998 | 0.905 | >0.998 |
| Trisomy 18 (T18) | >0.99 | >0.998 | 0.886 | >0.95 |
| Monosomy X (MX) | 0.989 | >0.998 | 0.83 | >0.95 |

High sensitivity and specificity detection of fetal aneuploidy at low fetal fractions is particularly beneficial for maternal samples obtained from pregnant women with high body mass index (BMI). Pregnant women with high BMI tend to have a lower fetal fraction for a similar gestational age. For example, a study of about 5000 maternal samples revealed that, for pregnant women with a BMI above 30, 11.1% have a fetal fraction between 2%-4%, whereas for pregnant women with a BMI below 30, only 2.6% have a fetal fraction between 2%-4%. See FIG. 11. Fetal detection using a dynamic iterative depth optimization (DIDO) method provides better sensitivity than sequential screenings (first and second trimester) coupled with nuchal translucency (see Baer et al., Obstetrics and Gynecology, vol. 126(4), pp. 753-759 (2015) and Table 5) for women with a BMI above 30. Thus, the ability to detect chromosomal aneuploidy at low fetal fraction with high specificity and high sensitivity is of particular benefit to women with high BMI.

TABLE 5

DIDO and Sequential Screen and Nuchal Translucency for
High BMI (>30)

| | DIDO | | Sequential Screen and Nuchal Translucency | |
|---|---|---|---|---|
| Test Chromosome | Analytical sensitivity | Analytical specificity | Sensitivity | Specificity |
| Trisomy 21 (T21) | 0.971 | 0.998 | 0.804 | >0.99 |
| Trisomy 13 (T13) | 0.981 | 0.998 | 0.932 | 0.996 |
| Trisomy 18 (T18) | 0.978 | 0.993 | 0.929 | 0.960 |
| Monosomy X (MX) | 0.971 | 0.982 | 0.801 | >0.99 |

Example 5: Microdeletion Determination

Maternal samples with microdeletions can be simulated similar to as described in Example 3, except a novel and arbitrary microdeletion region on the X chromosome of arbitrary size (2 million, 6 million, or 14 million nucleotides) can be introduced into the sequenced genome from maternal samples.

Read depths of the simulated maternal samples can be either 7 million reads, 9.5 million reads, 12 million reads, 14.5 million reads, 17 million reads, or 50 million reads. The simulated maternal samples can be analyzed within a batch of other samples, where reads for the other samples are subsampled to yield an average read depth of 9.5 million reads, 12 million reads, 14.5 million reads, or 17 million reads (since the typical average depth for a batch is 17 million reads, no subsampling is needed to achieve a batch-average depth of 17 million).

A Z-score can be determined for the simulated samples with a microdeletion and compared to a Z-score determined for real maternal samples without a microdeletion. The fetal fraction for the real maternal samples can be determined using sequencing read density (reads per bin) from the Y chromosome. The fetal fraction of the simulated maternal samples can range from about 0% to about 25%. The Z-scores can be plotted against the measured or simulated fetal fractions.

Example 6: Fetal Fraction Determination Using a Ridge Regression Model

Cell-free DNA of 16,434 maternal samples taken from women with male pregnancies (i.e., male-fetus maternal samples) was sequenced by massively parallel sequencing. For each maternal sample, the sequencing reads from each chromosome were aligned using a reference genome, binned in a plurality of bins, and the number of sequencing reads in each bin were counted. The bins were each 20 kilobases in length, giving approximately 155,000 bins across the genome. The counted reads were normalized to account for GC correction, bin mappability, and median scaling. For median scaling, the count in each bin in any given sample was divided by the median value across all bins in that sample, thus making the bin counts centered at a log 2 value of 0.

The measured fetal fraction, $FF_o$, for each male-fetus maternal sample was determined by independently calculating the fetal fraction based on the median normalized reads per bin from the X chromosome and the median normalized reads per bin from the Y chromosome. Fetal fraction was also determined based on chromosome 21 ($FF_{chr21}$) for those 129 samples with chromosome 21 trisomy (Z-score>5.0).

The fetal fraction based on the number of reads per bin from the X chromosome and the fetal fraction based on the number of reads per bin from the Y chromosome were inconsistent. To account for this inconsistency, a linear fit was used to model the general relationship between $FF_X$ and $FF_Y$ across all samples, and the slope and intercept from this fit scaled $FF_X$ to yield a fetal fraction inferred from the X chromosome, $FF_{IX}$. The recorded observed fetal fraction was then calculated as:

$$FF_o = \frac{FF_Y + FF_{IX}}{2}$$

A ridge regression model was trained using the male-fetus maternal samples (i.e., the training maternal samples) by regressing a $\log_2$ normalized bin-count vector representing the bin count for each bin (across all autosomal chromosomes in the genome) onto the observed fetal fraction $FF_O$ for each training maternal sample. The regression coefficient vector and the intercept were determined by minimizing the square error with $L_2$ norm regularization with a ridge parameter $\alpha=10$. A robust scalar transform was applied to the sequencing read depths such that the median was set to 0 and the interquartile range was set to 1 for each bin j across all training maternal samples.

Figure 12A:
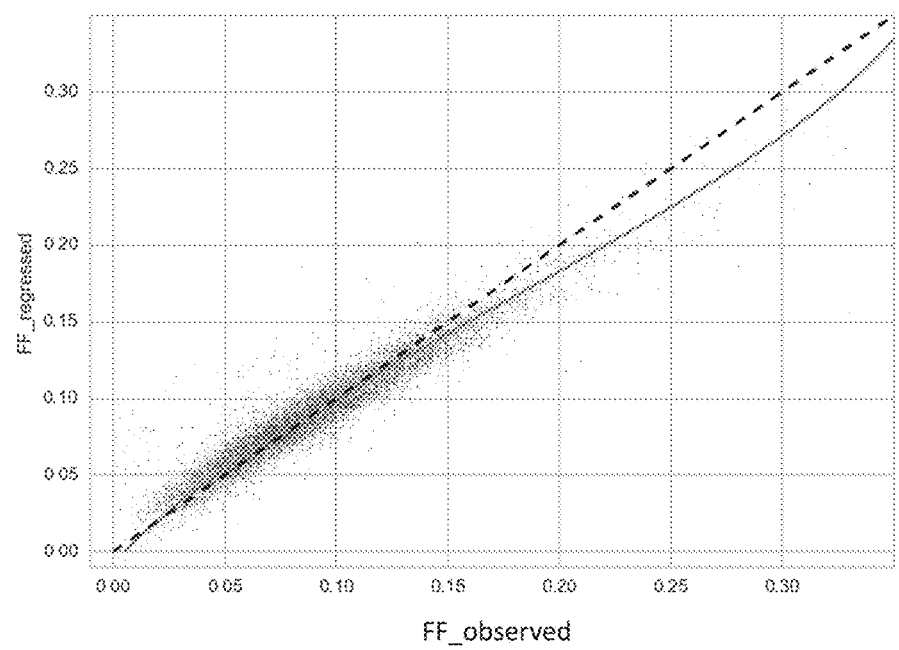
FIG. 12A shows a plot of regressed fetal fractions ($FF_{regressed}$) against observed fetal fraction ($FF_O$) for male pregnancies using a ridge regression model trained using the male pregnancies. A third-order polynomial was used to fit the data, and a corrected fetal fraction ($FF_{corrected}$) was determined.
Figure 12B:
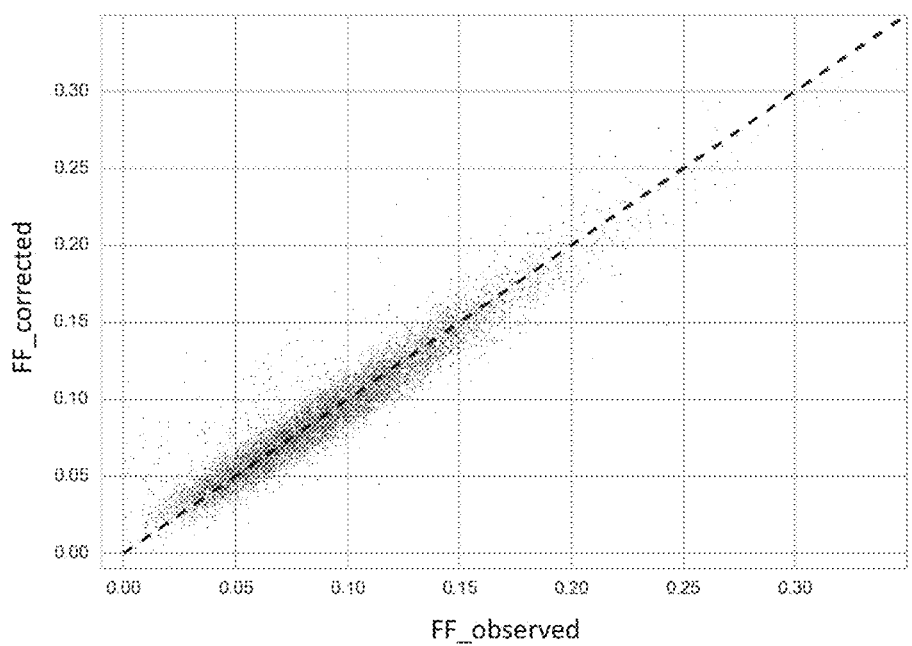
FIG. 12B shows a plot of the corrected fetal fraction against the observed fetal fraction.

The trained ridge regression model was used to determine the regressed fetal fraction of the training maternal samples. FIG. 12A shows a plot of the regressed fetal fraction ($FF_{regressed}$) against the observed fetal fraction ($FF_O$). A third-order polynomial was used to fit the data, and a corrected fetal fraction ($FF_{corrected}$) was determined. FIG. 12B shows a plot of the corrected fetal fraction against the observed fetal fraction.

Figure 13A:
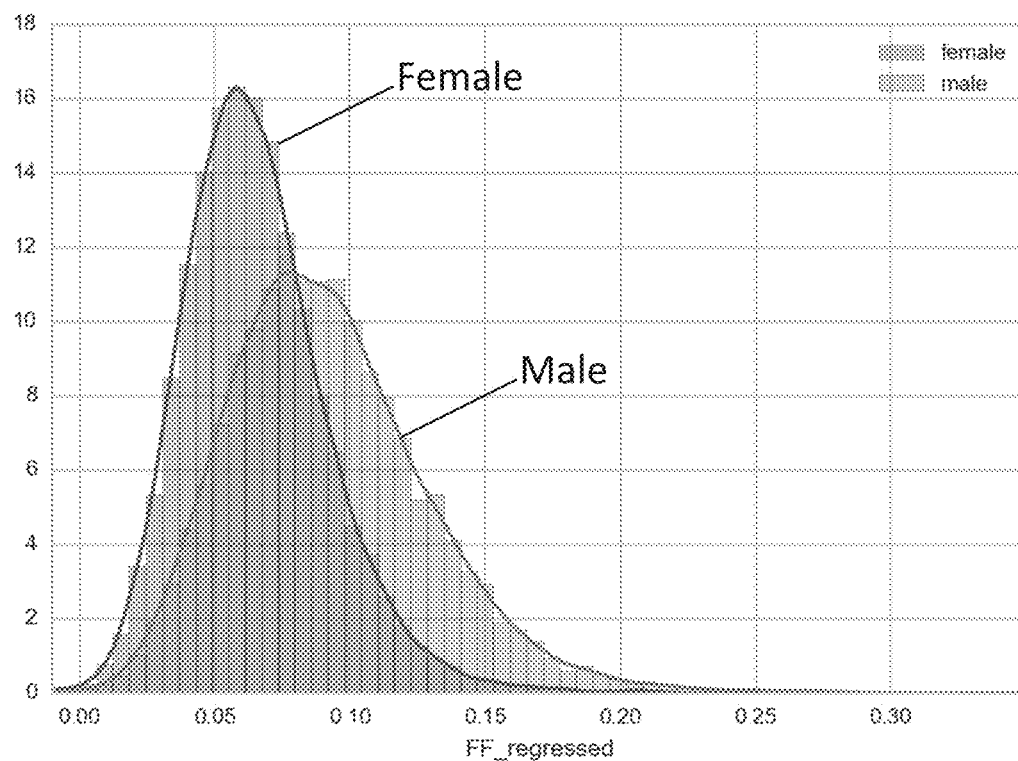
FIG. 13A shows a distribution for male pregnancy and female pregnancy corrected fetal fraction (corrected using a third-order polynomial).
Figure 13B:
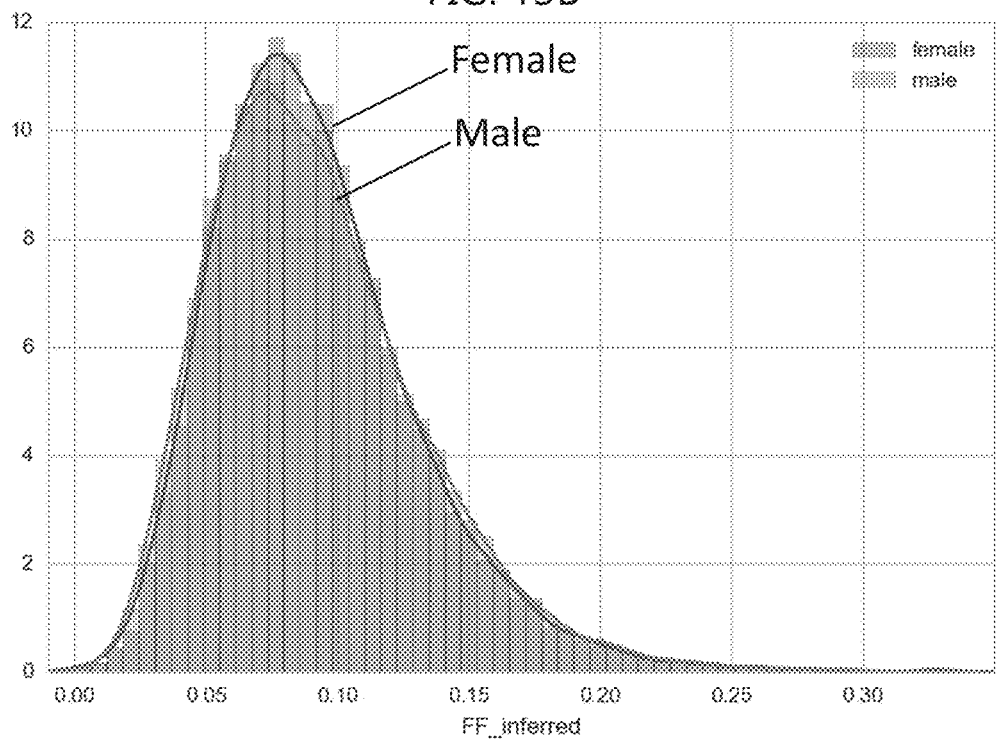
FIG. 13B shows the distribution for male pregnancy and female pregnancy inferred fetal fraction after the fetal fraction was adjusted using a scalar factor that accounts for differences between the male and female pregnancies.

The fetal fraction for the 16,434 male-fetus maternal samples and 15,064 female-fetus maternal samples was determined using the trained ridge regression model. For each maternal sample, sequencing reads from chromosome X (or chromosome X and chromosome Y for male-fetus maternal samples) were aligned using a reference genome, binned in a plurality of bins, and the number of sequencing reads in each bin were counted and normalized using the same methods as for the maternal samples used to train the ridge regression model. Additionally, an observed fetal fraction was calculated using the same methods as for the training maternal samples used to train the ridge regression model (that is, by using the sequencing reads from the X chromosome and the Y chromosome). Regressed fetal fractions for both male pregnancies and female pregnancies were corrected using a third-order polynomial to obtain corrected fetal fractions. A systematic under-prediction in the average corrected fetal fraction was observed. To correct for this under-prediction, the corrected fetal fractions for the female pregnancies were multiplied by a scalar (1.4569), determined by dividing the median corrected fetal fraction for male pregnancies by the median corrected fetal fraction for female pregnancies, thereby yielding an inferred fetal fraction. FIG. 13A shows the distribution for male pregnancy and female pregnancy corrected fetal fraction, and FIG. 13B shows the distribution for male pregnancy and female pregnancy inferred fetal fraction.

The accuracy of the trained regression model was evaluated by comparing the inferred fetal fraction to the observed fetal fraction for male pregnancies. Evaluation statistics are shown in Table 6:

TABLE 6

Comparison of $FF_O$ and $FF_{inferred}$ for Male Pregancies

| Criteria | $FF_O$ vs. $FF_{inferred}$ |
| --- | --- |
| $R^2$ score | 0.91578 |
| median absolute error | 0.00677 |
| correlation | 0.95697 |
| Interquartile range | 0.01004 |

Accuracy of the trained regression model was also evaluated by comparing the inferred fetal fraction from both male and female pregnancies to the fetal fraction determined based on chromosome 21 trisomy (129 male pregnancies and 124 female pregnancies). The observed fetal fraction for the male pregnancies was also compared to the fetal fraction determined based on chromosome 21 trisomy. These results are shown in Table 7:

TABLE 6

Correlation of $FF_O$ or $FF_{inferred}$ to $FF_{chr21}$

| | Male | Female |
| --- | --- | --- |
| $FF_{inferred}$ | 0.93298 | 0.90476 |
| $FF_O$ | 0.95430 | N/A |

The measured fetal fraction (either $FF_O$ or $FF_{inferred}$) can be reported as a fraction or a percentile. Reporting as a percentile can allow for comparing fetal fractions measured using different methods. These percentiles are shown in Table 7:

TABLE 7

| Percentile | $FF_O$ (XY) | $FF_{inferred}$ (XY) | $FF_{inferred}$ (XX) |
| --- | --- | --- | --- |
| min | 0.000490 | 0.0 | 0.0 |
| 1% | 0.016270 | 0.023100 | 0.024120 |
| 5% | 0.033130 | 0.036650 | 0.038820 |
| 50% | 0.086460 | 0.086250 | 0.086250 |
| 95% | 0.169510 | 0.167930 | 0.166020 |
| 99% | 0.224570 | 0.221450 | 0.224650 |
| Max | 0.344980 | 0.326570 | 0.508200 |

Example 7: Fetal Fraction Determination and Sensitivity for High-BMI Patients

Figure 14:
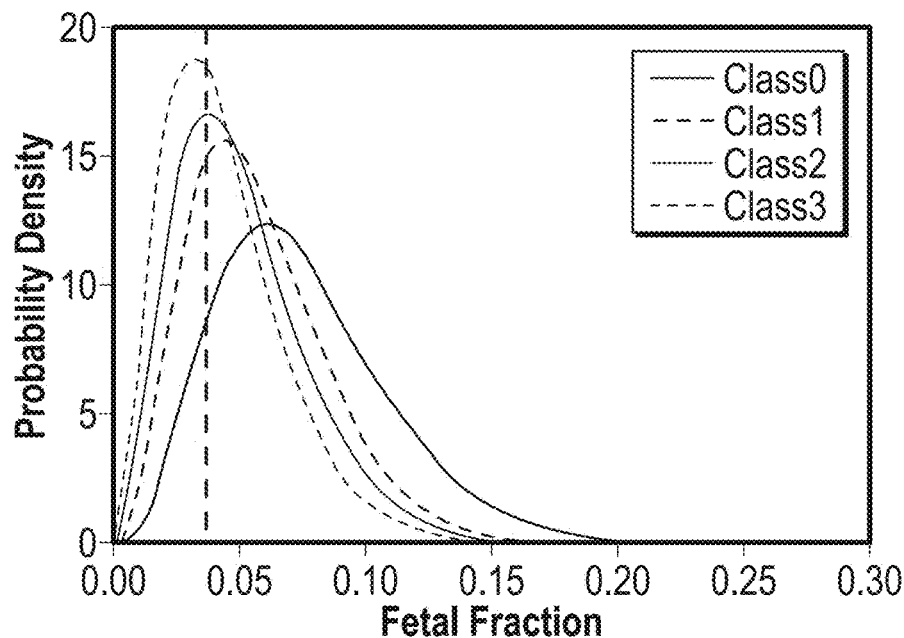
FIG. 14 shows probability densities of percent fetal fraction for various classes of BMI (Class 0: BMI<18.5; Class 1: 18.5<BMI<25.0; Class 2: 25.0<BMI<30.0; Class 3: BMI>30.0). Higher BMI correlates with lower percent fetal fraction, with Class 3 having the lowest median percent fetal and Class 0 having the highest median percent fetal fraction.

A retrospective fetal-fraction analysis from 51,737 anonymized samples was coupled with calculated sensitivity of the noninvasive prenatal screen described herein for patients with a BMI<18.5 (Class 0), 18.5<BMI<25.0 (Class 1), 25.0<BMI<30.0 (Class 2), and BMI>30.0 (Class 3). Fetal fraction probability densities for each of these BMI classes were constructed for a maximum likelihood beta-distribution fit of fetal fraction from the 51,737 samples, stratified by BMI class. The probability densities are shown in FIG. 14. The vertical line in FIG. 14 indicates 4% fetal fraction. The estimated analytical sensitivity for the detection of chromosome 21 aneuploidy stratified by BMI class was calculated by scaling the sensitivity at each fetal fraction level by the probability of observing samples with that fetal fraction, and then integrating over all fetal fraction levels. The estimated analytical sensitivities are shown in Table 8.

TABLE 8

Analytical Sensitivity for Chromosome 21 Aneuploidy

| BMI Class | Analytical Sensitivity |
| --- | --- |
| Class 0 (BMI < 18.5) | 99.79% |
| Class 1 (18.5 < BMI < 25.0) | 98.78% |
| Class 2 (25.0 < BMI < 30.0) | 97.62% |
| Class 3 (30.0 < BMI) | 95.41% |

Figure 15:
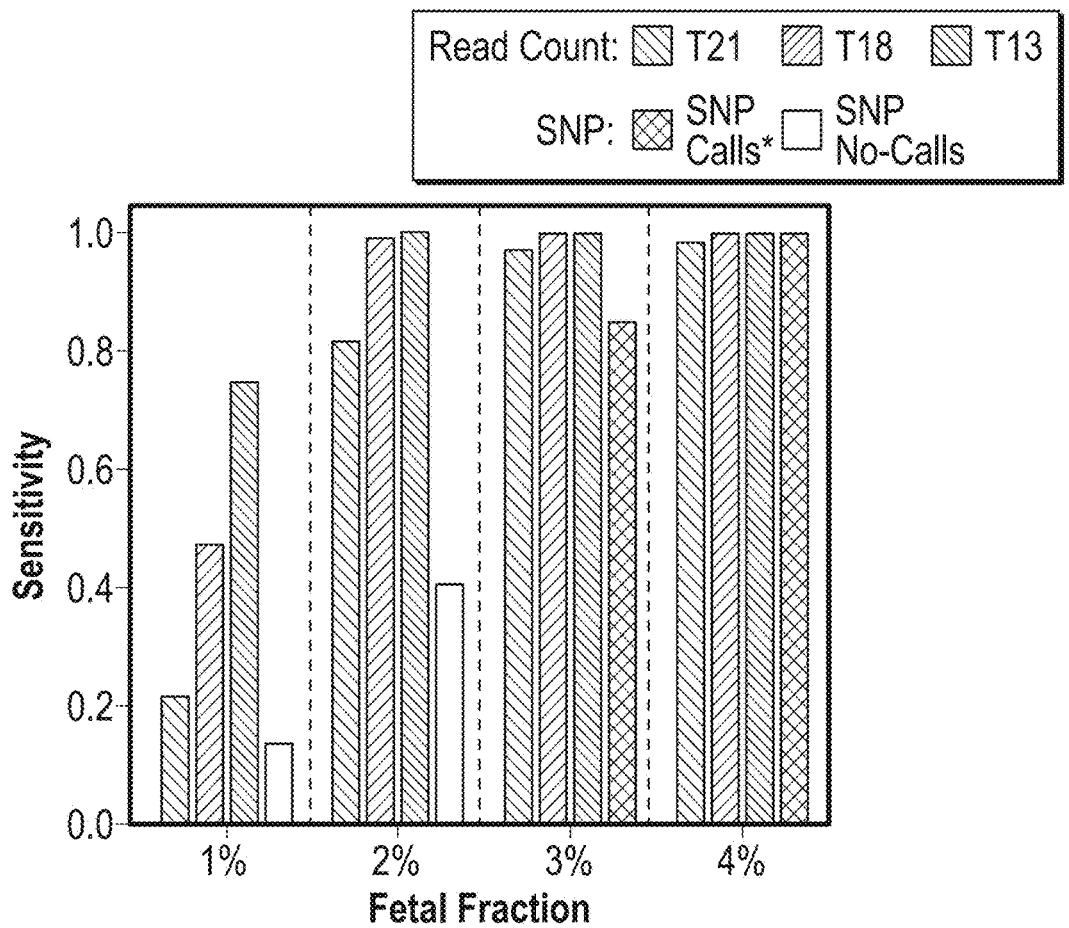
FIG. 15 shows sensitivity as a function of fetal fraction for the approach described herein (for chromosome 21, 18, or 13 trisomies) or the SNP-based approach. No calls are made for the SNP-based approach for a fetal fraction less than 3%.

Example 8: Fetal Fraction Determination Based on a Sequencing Read Count Compared to Single-Nucleotide Polymorphism (SNP) Fetal Fraction Determination Noninvasive prenatal screening can also be performed using a single-nucleotide polymorphism (SNP) approach, which measures the relative proportion of maternal and fetal genotypes among cfDNA fragments, and tests whether the observed patterns on specific chromosomes are more consistent with disomic or aneuploid fetal expectations. See Zimmermann et al., *Noninvasive prenatal aneuploidy testing* of chromosomes 13, 18, 21, X, and Y, using targeted sequencing of polymorphic loci, Prenat. Diagn., vol. 32, no. 13, pp. 1233-1241 (December 2012). Low fetal fraction is associated with high maternal body-mass index and certain fetal aneuploidies. The sensitivity from the noninvasive prenatal screen described herein and a SNP-based prenatal screen was determined using computational simulations. The simulation achieves a recreation of experimentally observed distributions from sequencing data of the two different techniques, and then applies in silico the expected impact of trisomy identification for chromosomes 13, 18, and 21 at varying fetal fractions. This simulated data was analyzed using standard practices to attempt to detect fetal aneuploidy. The fraction of those simulated aneuploidies which are detected is an estimate for the assay sensitivity. For the SNP-based method, sensitivity is equivalent between all trisomies due to the design of the assay. Additionally, fetal fractions below 3% are reported as "no calls" owing to the reduced sensitivity below 3%. In contrast, the noninvasive prenatal screen maintained >80% sensitivity for all trisomies above 1% fetal fraction. These results are shown in FIG. 15.

What is claimed is:

1. A computer implemented method comprising:
sequencing a maternal sample of a woman carrying a fetus at a first sequencing depth of 6 million sequencing reads or more to obtain at least six million genetic sequence reads, and aggregating the sequence reads into bins that are each at least one kilobase each in length, the maternal sample comprising fetal cell-free DNA and maternal cell-free DNA;
generating, by a computer processor, a bin count vector for the sequence reads, the bin count vector comprising, for each bin, a count of sequence reads;
determining a fetal fraction in the maternal sample, wherein determining the fetal fraction in the maternal sample comprises inputting, by the computer processor, the bin vector into a machine learning model trained using bin count vectors and known fetal fractions corresponding to a plurality of training maternal samples;
measuring a dosage of a genomic region of the fetus, wherein measuring the dosage comprises determining, by the computer processor, an average number of sequencing reads per bin and a variation of the number of sequencing reads per bin in the genomic region;
determining, by the computer processor, based on the measured dosage, an expected dosage, and the fetal fraction, a value of likelihood of a chromosomal abnormality in a genomic region of the fetus and a first value of statistical significance;
identifying, by the computer processor, a no-call status, wherein identifying the no-call status comprises determining that (i) an absolute value of the first value of statistical significance is below a first threshold and (ii) the value of likelihood is above a second threshold;
re-sequencing, responsive to identifying the no-call status, the maternal sample at a second sequencing depth that is higher than the first sequencing depth;
determining, based at least on the re-sequencing, a second value of statistical significance;
identifying, by the computer processor, an abnormal status, wherein identifying the abnormal status comprises determining that an absolute value of the second value of statistical significance is above the first threshold; and providing, by the computer processor, a report indicative of the abnormal status to at least one of the woman, a healthcare provider, or an institution.

2. The method of claim 1, wherein measuring the dosage of the genomic region further comprises performing an assay to generate a plurality of quantifiable products, wherein a number of quantifiable products in the plurality of quantifiable products indicates the measured chromosome dosage of the genomic region.

3. The method of claim 2, wherein the quantifiable products are sequencing reads or PCR products.

4. The method of claim 1, further comprising:
computing, by the computer processor, a scalar factor that accounts for differences between fetal fractions in female pregnancies and fetal fractions in male pregnancies.

5. The method of claim 1, wherein the plurality of training maternal samples comprises at least 100 training maternal samples.

6. The method of claim 1, wherein the machine learning model is a regression model.

7. The method of claim 1, wherein the machine learning model is a random-forest model.

8. The method of claim 1, further comprising training the machine learning model, wherein training the machine learning model comprises applying a supervised machine learning technique to the bin count vectors and the known fetal fractions corresponding to the plurality of training maternal samples.

9. The method of claim 1, wherein the genomic region corresponds to a first chromosome in the maternal sample, and wherein the expected chromosome dosage is determined by measuring a second average number of reads per bin and a second variation of the number of reads per bin for at least one chromosome other than the first chromosome in the maternal sample.

10. The method of claim 1, wherein the genomic region corresponds to a first chromosome corresponding to the maternal sample, wherein the measured dosage is a first measured dosage, and wherein the expected dosage for the first chromosome is determined by measuring a second dosage of at least one chromosome other than the first chromosome from the maternal sample.

11. The method of claim 1, wherein the genomic region corresponds to a first chromosome corresponding to the maternal sample, wherein the measured dosage is a first measured dosage, and wherein the expected dosage for the first chromosome is determined by measuring a second dosage for each chromosome of a plurality of chromosomes other than the first chromosome from the maternal sample, and determining, based on the second dosages, an average dosage for the plurality of chromosomes.

12. The method claim 1, wherein the genomic region corresponds to a first chromosome corresponding to the maternal sample, wherein the machine learning model is a first machine learning model, wherein the measured dosage is a first measured dosage, and wherein the method further comprises determining the expected dosage for the first chromosome, wherein determining the expected dosage comprises:
i. generating a dosage distribution vector comprising a second measured dosage of at least one chromosome other than the first chromosome for each maternal sample in the plurality of training maternal samples;
ii. training a second machine-learning model by regressing the dosage distribution vector onto the first measured dosage for each maternal sample in the plurality of training maternal samples; and iii. applying the second trained machine-learning model to a dosage distribution vector comprising the second measured dosage to obtain the expected dosage for the first chromosome in the maternal sample.

\* \* \* \* \*